US009518252B2

(12) United States Patent
Grallert et al.

(10) Patent No.: US 9,518,252 B2
(45) Date of Patent: Dec. 13, 2016

(54) ***LISTERIA* BACTERIOPHAGE P825 AND USES THEREOF**

(75) Inventors: Holger Grallert, Weilheim (DE); Julia Lorenz, Regensburg (DE); Anna Scherzinger, Bernried (DE)

(73) Assignee: DSM IP ASSETS B.V., Heerlen (NL)

( * ) Notice: Subject to any disclaimer, the term of this patent is extended or adjusted under 35 U.S.C. 154(b) by 97 days.

(21) Appl. No.: 14/119,811

(22) PCT Filed: May 29, 2012

(86) PCT No.: PCT/EP2012/002270
§ 371 (c)(1),
(2), (4) Date: Sep. 30, 2014

(87) PCT Pub. No.: WO2012/159774
PCT Pub. Date: Nov. 29, 2012

(65) Prior Publication Data

US 2015/0037284 A1 Feb. 5, 2015

(30) Foreign Application Priority Data

May 26, 2011 (EP) .................................... 11004348

(51) Int. Cl.

| | |
|---|---|
| ***C12N 7/00*** | (2006.01) |
| ***A01N 63/00*** | (2006.01) |
| ***A61K 35/76*** | (2015.01) |
| ***C07K 14/005*** | (2006.01) |
| ***C07K 16/40*** | (2006.01) |
| ***C12N 9/36*** | (2006.01) |
| ***C12Q 1/18*** | (2006.01) |
| ***G01N 33/569*** | (2006.01) |

(52) U.S. Cl.
CPC ................. *C12N 7/00* (2013.01); *A01N 63/00* (2013.01); *A61K 35/76* (2013.01); *C07K 14/005* (2013.01); *C07K 16/40* (2013.01); *C12N 9/2462* (2013.01); *C12Q 1/18* (2013.01); *G01N 33/56911* (2013.01); *C12N 2795/00021* (2013.01); *C12N 2795/00022* (2013.01); *C12N 2795/00031* (2013.01); *C12N 2795/00032* (2013.01); *C12N 2795/00051* (2013.01); *G01N 2333/32* (2013.01)

(58) Field of Classification Search
None
See application file for complete search history.

(56) References Cited

U.S. PATENT DOCUMENTS

| | | | | |
|---|---|---|---|---|
| 6,322,783 B1 * | 11/2001 | Takahashi | ............. | A23L 3/3571 424/543 |
| 2004/0029250 A1 * | 2/2004 | Sulakvelidze | ......... | A01N 63/00 435/235.1 |
| 2004/0223954 A1 * | 11/2004 | Bruessow | ................ | A23K 1/17 424/93.6 |
| 2009/0246336 A1 * | 10/2009 | Burnett | ................. | A23L 3/3571 426/326 |

FOREIGN PATENT DOCUMENTS

| | | |
|---|---|---|
| WO | 2010/020657 | 2/2010 |

OTHER PUBLICATIONS

Loessner et al., Applied and Environmental Microbiology, Jun. 1990, 56(6):1912-1918.*

International Search Report for PCT/EP2012/002270 Mailed September 26, 2012.

Van Der Mee-Marquet et al., "Evaluation of Seven Experimental Phages for Inclusion in the International Phage Set for the Epidemiological Typing of Listeria Monocytogens," Applied and Environmental Microbiology, vol. 63, No. 9, pp. 3374-3377, (1997).

Carlton et al., "Bacteriophage P100 for Control of Listeria Monocytogenes in Foods: Genome Sequence, Bioinformatic Analyses, Oral Toxicity Study, and Application," Regulatory Toxicology and Pharmacology,vol. 43, No. 3, pp. 301-312, (Dec. 1, 2005).

Klumpp et al., "The Terminally Redundant, Nonpermuted Genome of Listeria Bacteriophage A511: A Model for the SPO1-Like Myoviruses of Gram-Positive Bacteria," Journal of Bacteriology, vol. 190, No. 17, pp. 5753-5765, (Sep. 2008).

Gaeng et al., "Gene Cloning and Expression and Secretion of Listeria Monocytogenes Bacteriophage-Lytic Enzymes in Lactococcus Lactis," Applied and Environmental Microbiology, vol. 66, No. 7, pp. 2951-2958, (Jul. 1, 2000).

Borysowski et al., "Bacteriophage Endolysins As a Novel Class of Antibacterial Agents," Experimental Biology and Medicine, vol. 231, No. 4, pp. 366-377, (Apr. 1, 2006).

Guenther et al., "Virulent Bacteriophage for Efficient Biocontrol of Listeria Monocytogenes in Ready-To-Eat Foods," Applied and Environmental Microbiology, vol. 75, No. 1, pp. 93-100, (Jan. 1, 2009).

Hagens et al., "Application of Bacteriophages for Detection and Control of Foodborne Pathogens," Applied Microbiology and Biotechnology, vol. 76, No. 3, pp. 513-519 (Jun. 7, 2007).

* cited by examiner

*Primary Examiner* — Nicole Kinsey White
(74) *Attorney, Agent, or Firm* — McBee Moore Woodward & Vanik IP, LLC

(57) ABSTRACT

The present invention relates to a novel *Listeria* bacteriophage designated ProCC P825. In particular, the present invention relates to the endolysin PlyP825 encoded by the novel phage ProCC P825 and uses of the novel endolysin PlyP825 for controlling *Listeria* contamination and infection.

14 Claims, 8 Drawing Sheets relative lytic activity
1.2
1
0.8
0.6
0.4
0.2
0
Ply511
PlyP40
PlyP825
protein
0 mM EDTA
1 mM EDTA
10 mM EDTA
25 mM EDTA
100 mM EDTA
250 mM EDTA

SEQUENCE LISTING

```
<160> NUMBER OF SEQ ID NOS: 7

<210> SEQ ID NO 1
<211> LENGTH: 945
<212> TYPE: DNA
<213> ORGANISM: Bacteriophage ProCC P825

<400> SEQUENCE: 1

atggcattaa cagaagcatg gcttcttgaa aaagccaata gacgtttaaa cgaaaaaggg      60

atgcttaaag aagtttcaga taaaacccgt gcagtaatta aagagatggc taaacaaggt     120

atttacatca atgttgcaca aggcttccgt tctattgcag aacagaatga attatatgca     180

caaggcagaa caaagcccgg caatgtggta acaaatgcaa agggaggtca atcaaatcat     240

aactacggtg ttgctgtaga cttatgccaa tacacgcaag atggtaaaga tgtaatctgg     300

gcggtagatg ctaagtttaa aaagattgta gctgccatga agaaacaagg attcaaatgg     360

ggtggagatt ggaaatcttt taaagacaac cctcattttg agttatatga ttgggtagga     420

ggagaacgtc ctaactccag cactcccgct aaaccatcca aaccatctac acctgcgaag     480

ccttctggtg aacttggtct cgtagattac atgaacagca agaaaatgga ttcctctttt     540

gctaatcgta aagtacttgc tggaaaaatat ggcatcaaga attatacagg aaccacttca     600

cagaatacac aactattagc taagattaaa gcaggtgcac caaaacacgc tactccaaaa     660

cctccggcta aaccagctac ttctgggatg tacgtatact tccctgctgg taaaggtact     720

tggagtgtgt atccattaaa taaagcacct gtaaaagcta atgcaatcgg agcaattaac     780

ccttcgaagt ttggtggact gacttacaaa gtcgaaaaga attacggaga taatgttcta     840

ggaattaaga ctggttcctt tggacatgtc aaagtatatt gccacccatc aactggtgta     900

aaaattagca acaacggagc aggaaatttt ccgaatgttc agaat                     945


<210> SEQ ID NO 2
<211> LENGTH: 315
<212> TYPE: PRT
<213> ORGANISM: Bacteriophage ProCC P825

<400> SEQUENCE: 2

Met Ala Leu Thr Glu Ala Trp Leu Leu Glu Lys Ala Asn Arg Arg Leu
1               5                   10                  15

Asn Glu Lys Gly Met Leu Lys Glu Val Ser Asp Lys Thr Arg Ala Val
            20                  25                  30

Ile Lys Glu Met Ala Lys Gln Gly Ile Tyr Ile Asn Val Ala Gln Gly
        35                  40                  45

Phe Arg Ser Ile Ala Glu Gln Asn Glu Leu Tyr Ala Gln Gly Arg Thr
    50                  55                  60

Lys Pro Gly Asn Val Val Thr Asn Ala Lys Gly Gly Gln Ser Asn His
65                  70                  75                  80

Asn Tyr Gly Val Ala Val Asp Leu Cys Gln Tyr Thr Gln Asp Gly Lys
                85                  90                  95

Asp Val Ile Trp Ala Val Asp Ala Lys Phe Lys Lys Ile Val Ala Ala
            100                 105                 110

Met Lys Lys Gln Gly Phe Lys Trp Gly Gly Asp Trp Lys Ser Phe Lys
```

```
        115                 120                 125

Asp Asn Pro His Phe Glu Leu Tyr Asp Trp Val Gly Gly Glu Arg Pro
    130                 135                 140

Asn Ser Ser Thr Pro Ala Lys Pro Ser Lys Pro Ser Thr Pro Ala Lys
145                 150                 155                 160

Pro Ser Gly Glu Leu Gly Leu Val Asp Tyr Met Asn Ser Lys Lys Met
                165                 170                 175

Asp Ser Ser Phe Ala Asn Arg Lys Val Leu Ala Gly Lys Tyr Gly Ile
            180                 185                 190

Lys Asn Tyr Thr Gly Thr Thr Ser Gln Asn Thr Gln Leu Leu Ala Lys
        195                 200                 205

Ile Lys Ala Gly Ala Pro Lys His Ala Thr Pro Lys Pro Pro Ala Lys
    210                 215                 220

Pro Ala Thr Ser Gly Met Tyr Val Tyr Phe Pro Ala Gly Lys Gly Thr
225                 230                 235                 240

Trp Ser Val Tyr Pro Leu Asn Lys Ala Pro Val Lys Ala Asn Ala Ile
                245                 250                 255

Gly Ala Ile Asn Pro Ser Lys Phe Gly Gly Leu Thr Tyr Lys Val Glu
            260                 265                 270

Lys Asn Tyr Gly Asp Asn Val Leu Gly Ile Lys Thr Gly Ser Phe Gly
        275                 280                 285

His Val Lys Val Tyr Cys His Pro Ser Thr Gly Val Lys Ile Ser Asn
    290                 295                 300

Asn Gly Ala Gly Asn Phe Pro Asn Val Gln Asn
305                 310                 315


<210> SEQ ID NO 3
<211> LENGTH: 426
<212> TYPE: DNA
<213> ORGANISM: Bacteriophage ProCC P825

<400> SEQUENCE: 3

atggcattaa cagaagcatg gcttcttgaa aaagccaata gacgtttaaa cgaaaaaggg      60

atgcttaaag aagtttcaga taaaacccgt gcagtaatta aagagatggc taaacaaggt     120

atttacatca atgttgcaca aggcttccgt tctattgcag aacagaatga attatatgca     180

caaggcagaa caaagcccgg caatgtggta acaaatgcaa agggaggtca atcaaatcat     240

aactacggtg ttgctgtaga cttatgccaa tacacgcaag atggtaaaga tgtaatctgg     300

gcggtagatg ctaagtttaa aaagattgta gctgccatga agaaacaagg attcaaatgg     360

ggtggagatt ggaaatcttt taaagacaac cctcattttg agttatatga ttgggtagga     420

ggagaa                                                                426


<210> SEQ ID NO 4
<211> LENGTH: 142
<212> TYPE: PRT
<213> ORGANISM: Bacteriophage ProCC P825

<400> SEQUENCE: 4

Met Ala Leu Thr Glu Ala Trp Leu Leu Glu Lys Ala Asn Arg Arg Leu
1               5                   10                  15

Asn Glu Lys Gly Met Leu Lys Glu Val Ser Asp Lys Thr Arg Ala Val
            20                  25                  30

Ile Lys Glu Met Ala Lys Gln Gly Ile Tyr Ile Asn Val Ala Gln Gly
        35                  40                  45
```

```
Phe Arg Ser Ile Ala Glu Gln Asn Glu Leu Tyr Ala Gln Gly Arg Thr
    50                  55                  60

Lys Pro Gly Asn Val Val Thr Asn Ala Lys Gly Gly Gln Ser Asn His
65                  70                  75                  80

Asn Tyr Gly Val Ala Val Asp Leu Cys Gln Tyr Thr Gln Asp Gly Lys
                85                  90                  95

Asp Val Ile Trp Ala Val Asp Ala Lys Phe Lys Lys Ile Val Ala Ala
            100                 105                 110

Met Lys Lys Gln Gly Phe Lys Trp Gly Gly Asp Trp Lys Ser Phe Lys
        115                 120                 125

Asp Asn Pro His Phe Glu Leu Tyr Asp Trp Val Gly Gly Glu
    130                 135                 140


<210> SEQ ID NO 5
<211> LENGTH: 459
<212> TYPE: DNA
<213> ORGANISM: Bacteriophage ProCC P825

<400> SEQUENCE: 5

ggtgaacttg gtctcgtaga ttacatgaac agcaagaaaa tggattcctc ttttgctaat      60

cgtaaagtac ttgctggaaa atatggcatc aagaattata caggaaccac ttcacagaat     120

acacaactat tagctaagat taaagcaggt gcaccaaaac acgctactcc aaaacctccg     180

gctaaaccag ctacttctgg gatgtacgta tacttccctg ctggtaaagg tacttggagt     240

gtgtatccat taaataaagc acctgtaaaa gctaatgcaa tcggagcaat taacccttcg     300

aagtttggtg gactgactta caaagtcgaa aagaattacg gagataatgt tctaggaatt     360

aagactggtt cctttggaca tgtcaaagta tattgccacc catcaactgg tgtaaaaatt     420

agcaacaacg gagcaggaaa ttttccgaat gttcagaat                            459


<210> SEQ ID NO 6
<211> LENGTH: 153
<212> TYPE: PRT
<213> ORGANISM: Bacteriophage ProCC P825

<400> SEQUENCE: 6

Gly Glu Leu Gly Leu Val Asp Tyr Met Asn Ser Lys Lys Met Asp Ser
1               5                   10                  15

Ser Phe Ala Asn Arg Lys Val Leu Ala Gly Lys Tyr Gly Ile Lys Asn
            20                  25                  30

Tyr Thr Gly Thr Thr Ser Gln Asn Thr Gln Leu Leu Ala Lys Ile Lys
        35                  40                  45

Ala Gly Ala Pro Lys His Ala Thr Pro Lys Pro Pro Ala Lys Pro Ala
    50                  55                  60

Thr Ser Gly Met Tyr Val Tyr Phe Pro Ala Gly Lys Gly Thr Trp Ser
65                  70                  75                  80

Val Tyr Pro Leu Asn Lys Ala Pro Val Lys Ala Asn Ala Ile Gly Ala
                85                  90                  95

Ile Asn Pro Ser Lys Phe Gly Gly Leu Thr Tyr Lys Val Glu Lys Asn
            100                 105                 110

Tyr Gly Asp Asn Val Leu Gly Ile Lys Thr Gly Ser Phe Gly His Val
        115                 120                 125

Lys Val Tyr Cys His Pro Ser Thr Gly Val Lys Ile Ser Asn Asn Gly
    130                 135                 140

Ala Gly Asn Phe Pro Asn Val Gln Asn
145                 150
```

<210> SEQ ID NO 7
<211> LENGTH: 66849
<212> TYPE: DNA
<213> ORGANISM: Bacteriophage ProCC P825

<400> SEQUENCE: 7
tattaaattc tcatacagtg tagtcgtgtg tgttcgagtg aagcactgtt aaagaggtag 60
gttctaaaca tatcttaact tgttatacat atactataac agtattaaat accttatata 120
attatatggc tataacacgt cacaacatgc cacacatgtt atctcatata aacccgcttt 180
aacacgccaa taatggttcc taaccattcc ccaataagta ccccacatag tcccccaaat 240
agcccccata ttcattcgct attatcctcc acaaataccc cggcttatct gccctagatc 300
gtggtggatt acctgtaata tatccccctc atattccccc tatattagta ctgttattat 360
actactatcc aacatatcac ctatataagt acccggatat tacccgtaat tatacacgtt 420
gtgacacgtc cccacacgca cccttatatt taaggggtta aactgtgcgg aaattctagt 480
gcgattatac aacacttaac ctacacttat ccacctttcc aaagttaaat gcgttagaat 540
cactccattt cactattcta tatttaagac atattctcta tctttagaat attcagactt 600
ctatatccat aaaaagagcc cccagttaag ggagcttatt tctggttatc taatttgttc 660
cattcccgct cacattcagc caagaaggct tttatgcctt catttgtttg tggcaggtta 720
tcaccttgca ttttaacatc ttccatttta tcctttacaa acttgccttt accttccata 780
aactctgcga acccgttttc tatctcttca ttattcattg ttggaaccac accccattat 840
ccatgccatc atatccccac gcattacttc cagttgtgtc aattactaag acgtcttttt 900
catatacaat aacagctttg tctttgtaga tatttacgtc cacaggtttt tcatttggaa 960
agccgtactc ttttacaatc tgtttttcct tcatttcctg cgttacttta ctttcagata 1020
ctgcactcgc attttcaact tgattaaaca ttaccaccaa tgttactaca ctcaatacta 1080
ccaacgctac aaataccatc atcaattttt tcatcttctc tattcctcct aatttttatt 1140
tcgtgttcct tactactctt atataataac ataggtagtg ttacaaaaca agcccatttg 1200
tgttacagaa ttattacatg tgtaaaggga gccgaaagct ccccgctgtt attctttagg 1260
ctcaaagtgt gctaaacaaa tagctccaat tccaaagcag acgaatatca cgcctaacaa 1320
tatcatgact ttgttattac tgtcaccagt cttagctaga attttatggc tatcactcgc 1380
ttttacttcc tgtataactt ttttaggttg tggggacgtt tctacggctt ttacttttgg 1440
tttaacgggt tcttgtacag ttaaagcttt ctgaggagcc tcactatttt cagatacaac 1500
ttctttttgt ggttcttctt tcacaacttc tttttctggt tccggttttt gctgtggctc 1560
ttctttaact ggtgcaacaa tttcgtccca cgttaaaacc attacgaacg tatcacaatc 1620
ttttagcact gaaatagtgc cagtaaattc agttccccca aatggagctg tccaatcatc 1680
tttagaagtc catttttgac catcctctgc cacgtaagtc catgtaccag atttttcatc 1740
taaggtcatt tttacattaa cttctttcat cgtttctgga ttccattcat aatctgtaag 1800
tacttcttcg ccatccttta tttctgtttt agtgtcatcc aatattttac atccagtaac 1860
ttctttatcc caaattactt ctacttgctg tccgtcgata tagtaaatat cgttatcatt 1920
cgataactgt tttccatctg tagtgattaa cgttccttct tttgcgtgca cttccggaat 1980
tttttcatct gcatttactt gtgcccctcc aaaaatcaat actccaaaaa ctagactact 2040
cacgattaat ttacttactg aattcttctt catgtttttg ccctcttttc ctttattttc 2100

-continued

```
acttgacaac tatatcacac attgttaaac ttgtcaacaa cctgccagaa cttctatacg   2160
gttttggata agctcattac tttctgtgtg taattcgtat gtacttatta agtctaccca   2220
aaatggatac ttaagtttac cttcttcttg catttcgtcc aaaattgtgt tatactgttt   2280
tactgcatct tgaatattgt tagctgtaaa gcttttgtat tctgtcatgc tgttatcctt   2340
ttgacaaatc accgaccatg tggacggcac ttctttcaca tctatatcga aaatagcacc   2400
gtccacaaca tctcgcaaca tgaatttagt cttaaccaca atagcttacc tcgaaaagtg   2460
cataccaact tgaaggacgt gcttggaaat atttagtagc attaattgca tccattaaat   2520
agattgcgtc gtcagaatcc atatctacgt gaaaagtgaa accagagaac aagtctgtgt   2580
caatctcatc cgtattaaat tcgtagtgct cgaaaatatc cgttaactct tctaagataa   2640
gttcttgtgc aatttcttgc atatcttccg ctaattcttg ttcatcttct tcatatccat   2700
tccacccatt tttaaacagt tcgataaatg tttctttgat tgtgctatta gtagatgcgt   2760
gaactggata gtcttcgcta tcaccaaatc ttatatacag actaccttct ccactttcta   2820
aacgtgtagc ataatccttt gcattaatac tcatttctaa gcttctaagt tcattcattt   2880
ttaacgtcct cctcttaatt tatataccaa gtatatcacg ctctttgtta caattcaata   2940
cctacaatat tacaaatgtg ttacagtaag tgctgaaata tctgctcttg tttgtgtgtc   3000
aagtataaac tgttttgtca atttttggaa tttacttaca agtccatttt gtcgcataaa   3060
ttctttgatg tggcgaactg gcgtatttgt caaatgttgt acgtttgctg taatataaaa   3120
ttctccatca actaaagcgg ctacaggcgt tttatagctg taaagaactt tcgtgctgta   3180
ggctgttcca tctctgtaga tattcttctc cgccacttct gctttattgt gataactcgt   3240
tacattctcg aaaataggtt ctaatgcttt aatagtagtt tcttccgttt taaacaattt   3300
gaccactcct atatttttat tctggttact ttctgaattg gtttgttaag atagaatgct   3360
actgcttccg cttgtttgtc cgtgtaagtt tgcatgaaac ttgtaacgtc catgctaaac   3420
aagttcttga ccgctcttct taattccaga caatcaacca ccacgaactt acttttaccg   3480
attgaaagag attgaataac gttctgcatt aaattgtagc acctcctctt tttccaagta   3540
ggtctaattc agtgaaagca atttccctca atttgtcccg cgtaatagtg ttgtagtacg   3600
ttgtgaaatc ttggtaagta cattttgcga atgcttcaat tagtccgcct cgttttgccc   3660
ctacattttg cacgcaccaa gcttggcggt ctgaaactaa catgctaaca tattttacga   3720
gctctttctt tgacaatctc caaacttgtg cagatacaaa ttctttcacc gctaattttt   3780
ctacttcgat agttttactc attttactcc tcctccttta atattggatt actccggatt   3840
ttcttgtgtg gcgttttatc tctctttgta gtacgctgtc cgcaaaacgg aatcttgcta   3900
caattccatg cgtgcttgct gtgttgcttt taagttcgta aattgttcca tcttccattg   3960
tgatgaattg ataaactaag ctacctccat agatactagg tcttgactgt aagtaatatg   4020
actcattttg atttaccata tctggattaa tgaaaccatt ctttaagtgc ttttcttgta   4080
ttttgtttgc catttctaac acactcctca tttaatttgt gttgttcttt actactcttt   4140
aactataaca cgtccgtttc agtttgtcta ctattttaat gttacaattg tgttacaaac   4200
ttatttggtt cttttactat aaacttttgc caatctattt tggctttcga aatactctct   4260
tactttaaat acgcttgctg acctattttt ttcacttcca taaccaagca ttgccaaaaa   4320
ttcctctgtt gataaaccta ttccctcgta agttgctttg tcctttttga attccgcaat   4380
cgtaagttct attaaatccg ctaaagctgt taactccatt tctgaaatat cttcaccaca   4440
tgaaccaatt tcagttactg caaaaagtgc atcgggtgca acaaatgccc ttccttctct   4500
```

```
aatttcttgt cttgtcgctt gtcttaattt catttgaatc aattcctttc tacatttgat   4560
ataagattac taacaacatc ataacagata atgtgataag tgtcaagctt ggaatagctt   4620
ttaatagaag ttgtttcata ttatcgtttc ctttccgttt tcaattactt taattccgag   4680
cgttttgttt tctatagtag aaagtggttt ttgtatatct ccattttcct ccatcatcgc   4740
ccggtgtatc acgtgtaacg cttgttttaa ttccatttta gtttgtgtgt cgcatgtgct   4800
tttgtctact acattatata gagcgttcga agctctgttt aatagaatgt aattacttgt   4860
tgctgtcatt ttaaccagct ccttttaatt gataagctaa tcttagcacg ctttttttctg   4920
tttgtctagc ttttttgtgt tacaagtttg ttacagaagt acgtaaattg gatgacaaga   4980
gtttgattaa agttgacttt gacctttatt gatgtacctg aaatcgacgt ctttttaggt   5040
gtctgcggta gctttttgct gctgatttcc cgggcgcctg cgttcagtcc taaaaaattc   5100
cccggggata tacaaaattt cccccaaaaa atttccaccc aatttatggg tgagaataaa   5160
aaatccaccc aattatttga gtttgacgaa cggaatttga atcgaaacaa ttaagtagtc   5220
gaagcagaaa acgtaactca aaataataat gaatggatgg atttaatatc cagttcaaat   5280
ggaactgatt tttgtaactg tttttccaat acatttgact gttaatttac agaacgctgg   5340
gaaagtgttc atcattttta gcagaaattt gtattcaagt tttggctaat gtttgcgaca   5400
acgtttcctt aacttgtaaa ttaattttac cacagattgt tgcatttgtc aaatattgcg   5460
gaaaacgtgt tgaaacaagt gataccaatg gttttgagtt tccccagaat aaattttaaa   5520
aataatttca aaaaaaatat ttaaatctac agaataaatt ttaaaaatga tttccaaaat   5580
gacccccact tgtgttttga attgaacttt gtagaatata ttttcaaaat aaataccaaa   5640
tataactaaa atgtgatata ataaaaagat aaaggtggtg ataaaatgtt agatgatttt   5700
gtagaatttc ttccaaacta ttttgttaat aaggaaggga aagttctaag taaaatttct   5760
ggaaaaatta aggagttaaa aggttctaaa aatccacaaa aatatcaaca atttgggttt   5820
aaagttgatg gaaaacatgt tggaatacaa ctacaccgta tactagcaat ggcattcatt   5880
ccaattccag aagaattaaa aaatgctaag aattgcgtag accatataga cggtaatcca   5940
gaaaacaact ctttagaaaa tttaaggtgg actaactacc aagaaaactt agcaaaagca   6000
ggtagagaag gacaacgtcc tatgttattc acccatgaag aggcacgtta catgcgtaaa   6060
gaatattggg aagagggtat gtccatagag gatgtagcta aagagtttgg tggtggaact   6120
gataaacgtg tttacaatgg tgtacaaagt attattaaat acaaatcaat gcaatatgta   6180
gcagacgaat agccagagga ttaatcccgc tggcttttct ttttatcttc ttcttctatt   6240
tcaaaaattc ttttaaaagt atctactaag gcattaataa attcatcagt attcattgac   6300
tgattataaa cattaaccat aacagtattt gtaaaatatt tttctaaaac atcttcagaa   6360
actgcgtggc ttatagctcc gtctacagtg tcatcccaat caacctcgta agcaatcatt   6420
cctgtcattc cctgtgtaac accaataata gttcccttag aattgttata acgatgctgt   6480
acacgttcaa acttttcaaa cttactcatg atacgttatc ctcctagaaa tcatttgaaa   6540
aagttactcc acaatattca ttcttcccat aatgtataaa ggtacaggca ctttcatctt   6600
ctctcacact tattccaacc ttcaccactt ccccatctat gggagattta aatgttattt   6660
ttaaggcaac tttatgatgt gtattatggt taatccaagc ctttaccttg aatattcctc   6720
ttcgcatctt tactacggct gtattaggat aattttggga atgtttgtga aaatttcctg   6780
tgaatggatt aaacatttca aatatatcag ctctggatgt aggtaataac atatatctta   6840
```

```
cattttgttt agataataac tctctacctc ttctgtcaat tgctgaaaag ctttcttctc   6900
cgtgtgtaag taactccaat actaattttt ctgcaatttt ctttccttct ttacatcttt   6960
ctttcctcaa ctgcttagtg tgtttattct tttctttaat caatattttt cttgctctgg   7020
aaaatttttc cataattgct ttcacctcac ctctttattt acctattaaa ctaactataa   7080
tagctaaaat aataagaaat aatattacta acataacaaa tacaatgata gcaacccaga   7140
taattattgg aataaacact gtccaccaga caatattaat aataccagtt aattgaagta   7200
ttaataatac taggaaagca attacgcata ctgcacttaa tctcatactt attcactctc   7260
ctattagttt aatatcccac gggctcatcc aaacagttcc aaaactattg ttatcaaatt   7320
taactttata aattagtatg ccttccataa gtgtccagtc gataattgtt cctttttcat   7380
aattattggt ttcctccact cggcttccat ttgcataggg atgttctgct gacatattgc   7440
tgaatacctc ctctttattg ttaacccaat ctaaaatatc ttccaaagta ttaatactaa   7500
tcaacccccc cccatctcta tttaagtata acacaagcca ctgaaatatt caatggctaa   7560
gtgcttttat agtttatttt gttttactgg ataaaaacca agttcattct ccgcattcaa   7620
ttgattaaac cgctcctcag aaatctgcac atatgaagta tcttttgtag ttaagaatct   7680
attaagttta ctaagtctaa cctctttttc ttctccaccg tctacttcta atgaagtata   7740
tactgctttt ccctctgccc cattagtagg aataaaattt ataaataagc gtagtagact   7800
tccttgttta attccgtcaa aatctttaga agtagttggc ttagcatcat tatattcaca   7860
taatagatac gcatatactc ctgaactatt actcatataa atcataccct tctgccattg   7920
cacgaataac ttcctcagta actacaccag aaacacgtgc cacttcttct gactcttcat   7980
tatagagcac aattgtagga acagatttga ttccctctgc gattaagaca gcttcgtctt   8040
cctccacagt agcaatatta taatggaatc ctgtagcatc tagttgtggt tgtactaact   8100
tacatacacc acagttttct aatttttat aaaatacaat ataacctttt gccattaatt   8160
tttccccatt tctttttcta ataattccat taatatttta atggttaaat ctgttaattc   8220
tttatcatta ttttgtaaat catctaagga agcctttcct ttgaagtagt ttctgatatt   8280
catattaata acctgttcct gttcttccat aaatacttct ttgaattcta tattaatcct   8340
actcaatgta tccatttcat tttcattttc cacaaaaacg gaataccaat aaataccgtc   8400
attatctaag tggtattttt ctaattcttt tggagaaaaa gctataccta tttcattatt   8460
aaattctttt ccatagtcac gtagtttgtg gaaatcttta aatctccaaa ttaaacgtgc   8520
tcccttttg tttaaagtaa gaatttctct ttcttcatca tatctaagta gtacaaaata   8580
gtgcttactt tcatccaaat ctgcaaactt agtcatctaa tcccctcggt ttctttgtgt   8640
atttactagc aggctcatat gggttattct cttttgtaat agtcattcct aagtatttac   8700
ctctagttgg tttgtatgtt cctcctttat ctattaccca tgttcttaga gaagttttag   8760
gaactcccca caaatctgca actgcatcat gtgttttctt tgcttttaaa tctctataat   8820
aatttgaaag agtgtaatta gcaagagaag tacatgataa ttttctatca taacctttac   8880
ctatttcttc cagctctgct agctctttac caagctccat aacctcttta caccattcaa   8940
actcttcctg ccacacgtca ttataatcat taatctctgg atgttggtct aaaatgtcat   9000
ggagggcaat tcttaattct ttagctcttt ccctattttt cattatctaa caatcccttt   9060
ccaaaaacaa taccaactct attcttctct aacatagtat atacgtctga tggcacaaca   9120
taatcatatt ttatgatatt cataactaat tctttatctt ccagtttgtt tgtaatatct   9180
tcctccaaca tacttgtata cttagaaagt cctctacgtg ccttaccttt cttttccctg   9240
```

```
tcttctcttt gcttaacacg acaagacacg tactcatgta ttaactcaga ttcttcattt   9300
gtcaacatgt aagcaatctc ttcatccata ttaaacttca ctcccgcttc tttactcgta   9360
gtctttgtgg gaatttctac cccattcagc acagcttcta taaatagtct agctgttttc   9420
tgttctgtct tgtaacgaat gcggggaatg tttgctttta ttgttgcaat gttatttaaa   9480
atctttttca aaatatctga atcactactc atatcttacc tccttaactt tatattaaaa   9540
ttataccaca ctatttttaa tatgtcaaca aaaaagagag cataagctct ccttaatctg   9600
ctgttacatt tctagtggtt tcagcgttgt ttacattgtt gttaatagtt gcaattacag   9660
atttcttcat gtcaatagcc cactgaatag cttctaatac ttctgacttt tctttcttct   9720
tagataaacg tttgtaagaa gcttccaata ctttaatgtc ctttactaac ccctcgataa   9780
agtcaatctg gttttgtgtt tcctcattaa tttctttcac ggttctttct cccatctata   9840
attaattttt taacccattt aatttggttt tctgctaatt cttgttttgt tttggctaac   9900
tgttcctcag cttcaaagaa tttttcttc atttatcct ctagtcgtgt aatttcctct   9960
aaagcttctt cacaatcctt tgccagtttt tctgggtaat ctaaatcgta gcaaacttta  10020
acaatgacta cctgctcact tactcttttt aaaaactcca cataatctgg taataaatga  10080
ccatatttat ctttgttgca atatattacc tttgcaaaac tatcatattt ataaggagcc  10140
tttcttaatt cttcgtctac tccgtatcta atttctttct cttcttctat cattttagtt  10200
attttcgtta cttctcgttt tgcttttctc caaataatct tagtcttaaa ggtatctcca  10260
aaaaccattc catctaaata tctttcttta actagcaata accatattaa taaataactc  10320
acagccattg aaaacaaaat aacacagatt tttaatcctt cataggtggt gtattttccg  10380
tcattgtctg ttgttaccag tgtccataat gttgtaaaaa tgaaaaatcc tgctaatgtt  10440
attaatgtca aaaattctat tttaatgata cgattaatat atcttttaag gtctttacca  10500
aaacgcttga aaggaagaca ggcaccagta tagccctcca atatagtttg tatagcgtaa  10560
tcatataaca tcctatctat cttcttattc atcataaaac ctccctcgta atatatttat  10620
tataccacga gaaaggcgta ctgtcaaacg attaattaat aatttttgta tcaaattccc  10680
agtcatagac gttctcacgt aatgttagta atctacctct tacagtatta attgccatat  10740
tagaagccac gtgagaatca tttccggact gtgttacagg aataataaca acatcttctc  10800
ggaatgtact catgttcggt gtcttaaatc ttaccaaaac atggaattct gtcctaacca  10860
attttctcaa cttccatttc ttgaatattg attaacagtt taccactcgc aaaaggctgt  10920
aaacgtctgc gtaagctctc ttggaatatt aagaattccc ctaaattcat ttcttctaca  10980
ggactaagag aactaaattc aaaatccatt gaaaacctac ctccatcaat cccattctta  11040
caaatacgaa gataatctac tactacatta gcgttgtatg tttccatagt ttatttgtcc  11100
ccttccaata aattttttaa tagttgcata atatctccgg ataaatcttc ctcctcatcc  11160
tcttcttcaa tcgttactcc atttatttct tctgaccact ggctatggat ttcttttgca  11220
atattatccc catatttatc cccatattct gctttaaaat ctttatcagc caccaaaatg  11280
ttcataattc cctgtacaag tccttccaca gtagctcctg caaccattaa aaatgtcttg  11340
tcggtatctt tcatattttc tggttctggg aaatgttgca tggctaaatc cactaatcgt  11400
tcgccgaaag agtttctata agctagtaca aattccatta attcgtttga tttaatattt  11460
ctactatttg ctacggaagc catgtctttt aatctttcag ttatttcatc aaatgctgtg  11520
gaagtatctt cttcctcttg actttttgac aaatgacctt ctttcacttg aaactcctca  11580
```

```
tgtacgtttc ctttgtagat aatattagta tcactatctt ttaataatcc ttgtgaatta  11640
tcaattaaat cgtctaggtc tgtctcgtaa ttttccgcgt cttcttgaat atattcattt  11700
aacttatccc aatctttatc tactgatttc ttattaaaat tatctaacgg attaaattta  11760
gtcatttatt tctcctccaa aattaagttt aaattgctct gttgctagtg cggaatttac  11820
tctagctaat acggcacttc tggctaagct ggttgcttcc tcgtctgcgt cttttgtgat  11880
agcagataag gcgtgctcca aaaggataat cgctgcataa atctctgctg cggtatctcc  11940
acttgctgag aagctagaaa tccccagcat tccctctaaa tcgatttcca catcaatact  12000
tccactaaaa ctactttctt ccatttaatt ctcctccttc tgtaagaaaa atttatcata  12060
aatttcttca tctgtcaagt cttttattga ataataatta aggacgtgtt ggaagttttc  12120
ctctggcata gcaatttcta cagcttctct tgtttcagaa ttactttcaa gagtacgtcc  12180
atatccccat ccaaaactac tagctgccgg tattctacta atctgtaatt ctagtaaagt  12240
aaataacagt cttcgatacg tacctacgtt agttaaagga aaataaagcc gagaggtgtt  12300
aaaactatct tcaaaatctt taatagtgaa agctactaca gaagcaatat catctgactc  12360
ggatgctttt cctactacaa tgcgtaatct gtatttatat gacaatgcca caattatttt  12420
aaacactttc aacatataat catttaaaga ctgtgcggaa atgtccgcta atgcgttaat  12480
ccctacataa atactaatgg caggaacctc tttcatccct ctacggcgga attgtcgtgg  12540
atgtccaata agagaacgtg gaactgatag agaagagcct gtaacgctcc actccataga  12600
acctttctca agaatttgct ggaacctagt tagctctctt tggatggaag cttgttcact  12660
ctcttcgatg tagttagagt ggaaccgttc cttgtaggta ctggcaccta ttcctccatc  12720
tctccaatcg tcatcctctt ccatattctt gctgtaatta aaatcacttt gtttcttttg  12780
taaatcttta aaaatatttt cgtagtcatt tcctacatat ttagttaata aaatactatc  12840
ccaattgccc tcttttgtta ttggattaac tatctctcta tggctgaaat tattttcaac  12900
aacatctagc acaaactttc ctttctcttc tgccatcctt acacctctta aactttattt  12960
tttattgtct tgagaagtca cccaatctct aaaattgttc cacacttcat ttcctgctaa  13020
agaactagcg tgtttacttt ccaatccttt tcgaatagaa gacacatcag cccacgctag  13080
tgctttaaac agaacatttt caaatacgaa gccttctcca aagccttcta gttttttgta  13140
ctggctcata gcacggtaag agataacgtg gttaatcatg ttggcttcga ttacttcacg  13200
gcaacggtga ataaactgga ttaaatcatt atcacggtta gagataatca attctaattt  13260
cttgtcataa tcaacatgaa taggaacaaa acggtcaagt gtcgcagcat caatcttgtt  13320
acgacctgtg tagttcatgt ctcccccttt accaagcgtg ttacctgcca caattacttt  13380
aaagtcttca tgtgcatata ctgtttcgtc tccgccgtct gcactagaag ggaaggtcat  13440
aaaattgttt gcaagaacag tattaattac gataagggct tctggtgaac tggcatcgat  13500
ttcatcaata aataataacc caccattctt catcgcttta tacaagtttg ttgcttggta  13560
tttacccgtt ccatcacgga atccaataag ctgtgtgaac tcgtctgtaa ccttctgcat  13620
tggatagaag tctaaaccaa gtttagtaga tacgttttgt gcaatagttg ttttacctgt  13680
gcctgcttga ccatgtaacc agcagtgcaa acctgcctgt gtcatagcag agatacgtcc  13740
tgtttcacaa tgttcatcta ctcctgcact atatgcttct gtgctgacat agtaggtgtc  13800
atagttttgc tcacgtaaga agtttaaagc aggtgattcg aattctactt tttctaaagc  13860
atcctccaaa atatcgaaag ccttttcttt aacagtgctt tctaattctc caaacatgtt  13920
gctttttagt tcctcgaatt gctcctcaaa tgtttttact ttagaatttt cagtcatatt  13980
```

```
tttaatctcc tcttcctctt aattagtatc agtattttta tcttcatatt taggacttag  14040
aatccttact gttgtggagc gtaaacgtct gttatttaat tccaaacgta gtagcgaatc  14100
tgaaagttct tctaaggctt gtgcccgttt ttcttgtggc aatgttccat cttcaatttc  14160
ttttaaatgg actaaagctc gttttgcttg atttaggtgt gtgaaatttt tattggttaa  14220
ttcatttact gttgtgtaca cgtgaactaa atcagaatca cttggtcttt ctggcatatt  14280
ctcacctcct gtattactac tataccacaa aataaaaacc ctgtcaacaa taaagtgaca  14340
aggtttaaaa attatattga ttccgcacta tcccaatcaa tttcttctgg gttaattgga  14400
gcgttagggt ctggtgcatc tggtataata aagaatacat aagcaccatc tgggtttcta  14460
aattccactg acaatacctg tgaaccttca tcctctaact ggttggtagc atatgttaaa  14520
cgttttgcta attcgtcccc atcgccatcc aaataaataa ctccacgtgt atatccttta  14580
ttactcatag aatatgtgcg tcgccagttg ctttccatcc acatacaagt ggttaggcga  14640
ttggctatct ttctttttca ttacaaaaat ctgtcgtttg tactctgcaa tttctgcatt  14700
taatttctct tcattatttg cagaggcttc tagttcatcc aatagacttt tgttctcttt  14760
ctctaaatct tccacaagca tcttgtagta ctgttttgag ggcattagcc caccttcttt  14820
ctagtaccaa ccgtgaatga tatggaactc tttagctttc tcccaagttc catagcgttg  14880
tgccacatag gcatctgctg cacgttcttg gttagcaggc gaatagtcac ctttcaagtt  14940
ccattcttct agttggtatc ttccaatata tttaccagtt gcggaacggc aattataatc  15000
tcctcgtgac tccacatagg cgatatattc cttagcagat agtccattct gcgttccttc  15060
tggaataatt ccttttcctg tacttgattg tgatgtctcc tgcttggctg gctcttgaga  15120
tttctcttgg ttaggagaag cttgttcttg ctgttcttgt tgagcttttt cctcagcttg  15180
ttttgcttcc aaagcctgct gtgcttcttc tgcttcacgt tgctttttaa gagctaattt  15240
acgagctgct tccgcttttg ctttaagttc tttttgatgt ttttcgtaaa tttgttttgc  15300
ctgttccaac gatttttctt gcttagttgg tacagatgcg aacaatttgt caatattgtc  15360
tgatgcttca ttctgcttct taagctcatt caagtgctta ggcagatttt ccacagcagt  15420
taacgcactc ttctcttgga ctggttcttg cactggcttc actggggcag ttgttaaact  15480
aactgccata gctaatgtta gtagcattta tttcctccat ttgattcgtg tatttagtca  15540
caatttgtgc ctatgactat gatacagatt atagcacgtt ttgttgcatc tgtcaactat  15600
taatttaaat taagtcgttc gtctattctt aatcgcagta cttgaccacg tgttttgtat  15660
ggtctatcca ttgaaattgt tttgggaata cgccgttctc cattattatc tacttctaaa  15720
ataaagttag aaagtaacat atacagacgg tttggcaaac tgacggattc aaattcctca  15780
tagaaatctt cgcagattcc ttcaactatt ttagaacgaa gcagtgcttg ttgtaaaaca  15840
atttcttctt cttcaggaac aggcataatc aagcgaggat tattttcctc gtgtgcttct  15900
agttcttcga gaacatccca ataaaagttt tctaaacgac ttgcatagtg tctctgtcgt  15960
gtctttttac taagttgtcc atagcgtttt ttctccgtct ctgagttcat ttttaaactt  16020
ctcacttcct cgtagtattt ctttaattcg tataacttgc ctgtagatag ttacccggtg  16080
ggctcctaat atatccgcaa tttctgatat tgtataatca taaacaaaat aaagaatagc  16140
taccttttgt aatttttctg gcatattaac tgtcttaaac gcatcttcca aaatgtttaa  16200
caactgattt tgaacacttc cgtggataga ggtgctatcc ttttcatggt ctgaaagtaa  16260
tttcaaaaca ttattattca ttattactaa ctttttaggg aagtaatctg attcatttgt  16320
```

```
ctctaggaaa ctcatctttt ttccaactct caagtaaatc cagtatttgg tcgtatactt  16380
ccgtgtaaga acgtccgtta tttgtaataa cagcatctat tggaatgtct tttccatcaa  16440
atactacatc taattcatta tttatttcta ggtcttcacc taaatgttct gcacgtttta  16500
aggctacatc atcatcacaa acaacttgaa taattaacat gccacctcgt atacagaaat  16560
ctaattcgtt ctcttgtctt acgtcatcta tgacaacacc tacagagccg acgggcattt  16620
gggctgataa cttcttaacc caaacgtcct cgtcaatctc tctcatggct tgtccgtact  16680
ttatgtattc atctcgtggc ttcggtgacc gtggaatatc tgggaatgtt ctatggaatt  16740
catctttcat tgctttgcca aatcccatgt ggtgattacc agtatagctt gcaataaact  16800
ctgcaatagt tgacttacct gttcgtgatt ttcctataat tgcaatactt ggatatttca  16860
tattattcag tccttgtaga caatgaacgt agttcttcaa tatcctttaa gaacgttaac  16920
gctacggcaa tagcatctgt ttcatcgtct gagtattcta gcggattgtc catatgtatc  16980
cagcgaggta aggcatccgc tacttgttgc ttagaggaat ttccgttccc tgtcactgct  17040
ttcttaactg cttttggcat gtagacattc attttctttt ctccgttgcg gaactcatag  17100
tacaaatggt ctagcacccc ataaaattta tagagaatct tagttgctct gtttccgtgt  17160
acaaacccac cctcacgaac aataatatcc ggttggaatt cttcccaaat agctaacatg  17220
gctttctcaa atacatctaa tcttctgcca atatcccaag ttgagtgggt aatgatgata  17280
cgtgtttcaa ttagattaca gttaccgtaa gcatcacgct ctacaatagc tactccagtt  17340
ttaacacttg ataaatcaat tcctacaata atcatttagc tctctccctt atttctttaa  17400
tccatctata agcttcctta caaccactct gcatccattt aggcatagta gatacttggc  17460
tgttatataa atcaatggaa gcttttaact gttcatttgt taataacaaa gctgtatgaa  17520
gtttaaatgg agagaacgtc catgctgtta catcaaatac tggtagttct tttgcattag  17580
ccaatctaac ggcttctgct aaatgtgctt ccacatcgtc tttcatttct tgagttacat  17640
gaattccaaa acatctcata ggtggtgttt taataagctc ttgttcatcc atgttccaag  17700
attgtttact tgcgttctgg tacataatta tgtagtaatc taaatcgtgc ataagtgagt  17760
atgatgtaac ctgcttaacg tgtttagggt ctggctctct catggagtat aaggacgttt  17820
tagctgctgt tccttgttta gactttactt ccagtccaac acgaatcttt cgccctgtgg  17880
acgttgtgta caccatgaca ccatctactg agccactaat agagaaatct tgtccattat  17940
gactaaaata tgctacatct gtggagaaat cttcaaagaa cggaaactgt tttccatcaa  18000
tttctttgcg gtcaaaacca aatttaggtt tctctccaac aatactttca taatgttttt  18060
cttgtagtaa taaattcttt tgaaccatat ccccaattac ggttccaata tcttgccact  18120
gaccgtgatg ccacatcttc actgctttat cataaggtgc ttttgtcaat ctcataacgt  18180
gattccataa gctatctcct gttgagcttg ctctaaatgt tggaatgcct tgtgctggtt  18240
gaggtacttt aaacgtaggt gaagttgcat aggcataaga actatatatg taatggtcta  18300
ctgctttatc ttcacgtccg ccagctcccc agaaattctt gaactgttgc tcaagttctt  18360
gtgccatctt ttcagcacgc tgttgttcat tagacactta ttttttccct cccaaatccc  18420
atttttcgct aacgacaata cctgcatagt aaacaattgc tgttaatgag ctggtaggtg  18480
acataggttc cgcaacttca aaggtaaagc cgtgcacgga agggcgtttt ttgttaatta  18540
cttttgaaat acttctgcga gggatgccag ttacttcatg tgctttcgta acactttcaa  18600
accaagcaat tgcttctcca tccttaaaca tttctatagg acgttttcct cgaattgctg  18660
tggcatcttt gttatgtctg taatattctt tcatgttgtg tgagctatca caccactgta  18720
```

```
gattaagtaa attattattt gttttgtcgt ggtctatatg attaagtata gcatagttta  18780
ccggattatg caatagtgtt tcaccaataa ttctgtgaac aaatactctt tttcctttaa  18840
tagatacttg catgtatcct tcaatattag cagtctgttc caagggaact aatttagtgt  18900
tgttttgaaa gtcctgttcc tctttaaaga ttgttccatt actgctggct acgtatccag  18960
ttaggacttc gccattaagt actgccgttt taataatatc tgttaccatt ttattactcc  19020
tcatatgtac gtcaaaagga gagaaagctc tctccatatt gactttattt gtcgaaccat  19080
tcttcgactg aaactaaacc atcttctttg acaatgttat catattttcc atacttctca  19140
caccaacgtt taccaattgc catatcagtt ttagctggaa cagagaactt aactgtttca  19200
atcataacgg aacgaatcat ttctacttct tctctagtaa tatcctctgg aacgtagaac  19260
aataattcat catgtacctg tgaagatatt tcaaactttc gaccgggtgt tgataatttt  19320
ttcattagtt tagattgtgc tatcataact tcttttgtct gagtagctgc tccaccttgt  19380
actttggcat tagtaatttg gcgaatctgt ccacggaatt cccagtcaaa agcacgtgtt  19440
gttttcttac tcatttctct gtcgaaatct ttaccaatgg ctttagggaa tcgtctacgt  19500
cttcctcgcc aatcttcaat gtagccccgc tgtgttactt cacgagcgtt attatctatc  19560
caattcttaa cggaagggaa cttagcatag aagttatcca tgattgattc tgcttcttta  19620
aaatctactc caagactatt ggctaaagct ttaggagaca tgccataaag gatagcaagt  19680
acaaccgttt taatacgttt acgatacact gtgccatctc cacatttatc aagtggtacg  19740
tcaaatgttt ctgatgcaac ctcactatat aagtcacgtc cttctctgta gaaggctaat  19800
agtttagggt cttgcgaata atgtgctagt agtctgggct cttgttgtag ttccttagac  19860
ctactagacc tttcgagctc gttacactct tcccagtttt cactaggact ggactaactc  19920
ttgccgccat gtggttagcg accgtggtgt ttccaccccc acttgggggc gtacttcctc  19980
tcggaatagt ctctacactc gggtttatta ctttaatatt tccaaatgaa tcctgcataa  20040
ctggtagtta aacctcttgc cgccctactt atttggttat tatctaaacc agtcatatta  20100
gaggcatcag taggtgactt aaattcacca atcagttctc cttccttagt atactgaaac  20160
acttttctaa ctttaactct tcctttatgt gttcccctat tgacagcatt tatttggttg  20220
tttttgttgt ctacccattc caaattttct acacggttat cacttctatc tccattaatg  20280
tgatttactt gaggcaagtt atttggatta ggaatgtaag tttctgcaat tatacggtgt  20340
actctgtaca attttctagg aatatctctt tgtaatctaa ctctaacata accgtcgaac  20400
aatggtgaca acgtgctctt aacccattca ttagtcttac ttaggtagta gacatttccg  20460
tctgtatctg ccttgtaaaa cttgcttggt aatccgtctg caactatatt tttcacatgt  20520
tttcctcctc tcttattatt tttttgttac cacatattaa ccctagcacg ggattggcat  20580
aggctacgcc cttagctttc cccgttttag ccacgttttt attcagccaa cattaactga  20640
aatcggcaga tagtattaac tgccctttttg gtgcaataaa catcttacga gcttctggcg  20700
ggatattctg gaagtttggt tccttagagc tatatcgacc agtctttgtt ccattctgtt  20760
taaactgtgc atgaatacgt ccatctggtg atactttgtc actagctttc ttaacaaatc  20820
cgtctagcag tttggatact ttgcgatatt ctatgagaat cttgatagct gggtgacggt  20880
tttctagttg ttctaatact tctttgccag tgcttcgttt atttctttct ttgaagctaa  20940
cgtaatcacc taatttaaac ttatcatata ttacttctcc aagttgttgt ggagaattgt  21000
agttgatact tccaaaccag ccatctagtt catctttaag acgtgctgat tcttgttcaa  21060
```

```
ggaaggcttt ctggctttct acttccatca agtcaagttg gaaaccaaca cgttccatgt  21120
catttgtaac actgataaca ggctgttcca cttcctcata taacgtttta actccagcga  21180
aggttggctt actcatgtaa ttcattaaga atttaaatag tctaagtgtt aaatgagtat  21240
cctttgctgc atatacggaa gcatattgga taggaacata tctaaagtct ttcgcatctt  21300
tgaatagtgt gtcaaacgta tctgattcag ctccaagata tttaggtgcc aaatctttca  21360
gacgatagct tactaagttt tcatccatca agtgcataat aacagcagtg tcatggatgc  21420
gacctttaat ttctatgttg tttgaataca ggatgtctcg gtcaaaacta gcattatgga  21480
aaactaggtc tgtatcttct cttccaacta attcagctaa ggcactcatt gcggagatgt  21540
ttccatcatc atgatagtta gtgccatcca tgtgcagaag tggtacataa tagtgtttgt  21600
ctgccttgtc caaagatact gagtatccaa ctgtttcgtc tctataaaca tctaatccag  21660
ttgtttccgt atctatcgcc attagagttt ctttacccgc cagctttaac atctctaaca  21720
tttcagcgga ggttgtaata gtatagtaat tatctggctt agtccttaga agttcttcta  21780
gtttttcttg tcgttgttct gcttccacct tcgtatataa tcgtaaggct tctgctttgg  21840
taaacttctt aggtttcttt cctacttgag gctctcggaa taattttcct tcatccatcc  21900
gttgtttaac aatacgtaac ttctctttag ctgattcaga attcttcatt tctgcaatag  21960
ctttccaagc atcttccaaa ggttctatct cgtaggtttc tttgatgcgt tcttttacct  22020
cagctacttc ctttggaatt cgtgctgtag gtgccttaat cttatctaaa ttcaaggctt  22080
ttaaaacagt gttttcaaac ttaccttggg attttaccac atcgcatatc cccctttctta  22140
tatttgtcta tgaatttttg aagtcctttc gtagttgtgt ttaaactttt ggcgacttct  22200
tccacagaac atcccgcact gatacttaat aaggcattcc aaatatcatt aggaaattct  22260
tcgtcatctt caatatcgta cgggtatgta tccagcatat ctcgtaatgt ttcttcaagt  22320
agatgttctg gcgttctttc tttatatgta ctaagtattc tataattggt tgtgtgcttt  22380
atcaaatcac gtatatcttc tgtttttaaa tctggaaact tcttaatcgt ctcttccatt  22440
tccgtgtata aattagctct caaagtagtt acttcggctt ccgttatgtg gaagccttgt  22500
ctagcctgtt cagtaactac gagtatgagg gcataaatct gttccatttt taccatgtac  22560
tctcacctat ttcattaagt attcttttcc attttgcatc tgtttcaaga cttcggaagc  22620
tagggaatcc atcataggca tttaaataat cattaaaatc ttttatttca tctggaaaca  22680
ctaccataaa tctatcaatc atgtaccctt cgaaactttt gtacatcgct ttattaaatt  22740
ctcttccctt tttatcattg tctcctgcaa agaataggcg tttaattcct agtgataaaa  22800
tagaatcacg ctgtacctta gttaatcggg aagttcccac ggctactgca cagtatccga  22860
tagcacgaac ggacatagca tcaatttcac tttccacaat tattaatgta gaaggcttct  22920
gctgtagtgc ttgtggcaat ccaaataaat tattctttgt aattcctact tctttgtgta  22980
acgtttcaaa tccctttttta tccgtataac gtatcttaca agcaatcaaa tcattctttc  23040
ggtcatacca tggaatatag actttgcggt cttcttcgct agttccatac atctcttgga  23100
tttctttagt aatcccacgt gattccaaat aggggctaaa tacttgtgat gggattgtta  23160
gaggcgtgac ttccttgctc caaagttttc cctgtagttt aggaacgcca cttttgagtc  23220
cgtaagtttc aactagataa tctgctactt catcataact tatatctcgc agtcgtgaaa  23280
gtaatgaaat tatgtttcct gtttcaccac taccactgtc tccccaagtt cctcctccat  23340
ctgaccctgt gaagtttaca aggttaacaa agaatgacgg gtgagaatct gctctaaaag  23400
gtgagttgca tattaacttg tcttctgacc atctagcgtt tgtccattcg tgctcttgta  23460
```

```
gttctgacac gatgtcaaca ttgattctat ttccacgtat ctttattaac gtcactgtaa  23520
acactccttt tctctatata ttataacata aacaaagtgt gaagtcaagt taaccgcaca  23580
ctttattttt attagatgaa taaatctttg tttgcggatg gttctatttc gtgaatcaat  23640
ccataactag gtagccatac tccggttagt tcaacgttct ctccgccagt acgcccttta  23700
acaatctcta caatgaagtt cttatccatg gaatcgaatg caataactac agcacagtct  23760
tccaaaagag aagatgtttt cttcacttgg tcacgagttg gggcaagaag ttcccgctcg  23820
tctttggata ttttaagttc ttctgcttgg gtgattaagt gcataacgat gttgtgcttc  23880
gcagcaatct tacgaacacg tttagaagtt tctgctgcgg ctcctccagc tgttcttgat  23940
gagttatttt catattccaa aagatagaaa gcatcaatta gaactacatc tgcattagtg  24000
tttacaatgt cgtcttctag ttggtcacaa ttccaactat caaaacctgg ctcgttggct  24060
gaacgtacaa taatacgtcc cataactttg ctcataatat ctgccatagc ttctgcgaaa  24120
tcttcttcat ctggaataga tagtttacca ttcattaaag ccttaacact atatcctgct  24180
aagtattctt caataccaag cttaacacta ttcttcttat acatcgctgt gataatagaa  24240
taagcacgtg tgaagtattc atacttagac atttccagat tatagataag aactgtggca  24300
ccttcgatag ctgatttaat agcttcttga agtgttatta aagatttacc acgtcccgaa  24360
cgtccaaacc atagaataca gttaccagaa ttatatccgc caacctcttt attaatcgta  24420
gggaaagatg aatcccaagt tttacgtcca acacctgttt ggatattgcg gtactcttct  24480
tggaaccaat caaagtcatt aataatatct gctcccacgt ttgcaggcat ggcattatta  24540
ttttgcattt gtttagcacg gtcattaaca aattcccaga agtcatctac tgagttatag  24600
ctatcgaaac tcgttagaac ctcatcatta ataaagttta ctgtttctac ggctaaatta  24660
tagttctttg tttcacgtgc catatattcg aacgttgcat caatagcagg catatagcca  24720
aactctggat acttagtcac aacggtttct gcatcagggc atttaccata tctatcatga  24780
tattgtttaa tgaatagata agtttctttt tctgtttgag ttagaaaatc tttttctttg  24840
attccaaatt cagctaaggg acggatgttg tcatcctcaa tgatacggct taggaattgt  24900
gttccataat aaatagccat ctagttcact cccttacgtt tggatttacc cttgaactcc  24960
actacgaatg tgttatgacg aattctatcc cacaaacgtg tgtctaagga cattgccatc  25020
ttttgcattt ctaagttgga tgtataaata gtgatacgtc tgctggttac tcgtgagttt  25080
attaaatcgt gaatgtcccc acgcaatcct tctgttacag aacgtactcc aatatcatct  25140
atcacaagaa tctttgcttc ttttgctttg tttaatcggc gataaaattc tgtggaagct  25200
tccgaagcca tctctgtact gcttgaagcc atccggttaa actgattgta aagtgcttgt  25260
aattcgttca tgtctacata atatgcgaag tttctagtta gtttctttcc gtgtttatta  25320
gcgtaatacc aaccatcaaa tacaagctga ttaagtaagg cacatgcaga agttgtttta  25380
cctgttccgg ttgcatcact atagaagtac atgtttttaa tggagtttgc ggggtcgttc  25440
atgtctgttc catcaaacaa tctctcaata gatgggacat agttagggaa aatagttccg  25500
tataattctt tttgtcccgc tttcgctggt gaattatcca acataatatt ggaaaactca  25560
ataggaatat tagcattacc atatgaacct cctactccac taccatataa atcaatgtaa  25620
aggagtttgg ctctattaat aacatcctct aaatccattc cgttcttttc agacaatcgt  25680
ctgcaaaatt cttcgtattc caaaccttct ccccctcggt attaaaagaa atcactgtaa  25740
tcaattttgt ctttatctac gtcaatagta gactccacat cttctcccat gaactgagca  25800
```

```
attgtagcac gttcaatctc ttctcgtaaa ctacaataaa taaacatgaa attaataggg  25860
gttgttcttc ctttaaactg ccaagcttca aaactattat caataacctg tttaacgaat  25920
tcttttgtat gctgttctcc gtatcttttt attagagaat tctgttgagg gtatgaactt  25980
acatgatgtt cttttccaaa taatgccata ttcttacttg ctatataaga attgaagctg  26040
ctaccattcc actcacttac tggaatactt tcccaatctt tataatcaat tttcttttta  26100
gccattaata tctcctccta aatattttct ttcgttacta agcatatctt atcactactt  26160
ttaattattg tcaaacataa atttccaaca ataattgtgg tggcttttta atttaccatg  26220
taaacatctg cttacgccac tggggttgaa tcctcccaat ctttttgctt caccaatact  26280
tttaaatatt aatatacttc cgtcacttaa agaagtgcct attattgctt tacttctttt  26340
atctatactt ctttgcagtc ctgttccatg gttcatgttt tctttatttg ttacccattc  26400
aagattacta acattattat catccttaat ttcgtttata tggtttactt gtggtttatc  26460
ctcttcattt ggtataaatg ctaaagaaac tattcggtga acctttactc tcttagtttc  26520
tccacacgaa gaaagttgaa ctgttaaata tccatattta tccttcgtag gaactagaaa  26580
tctatttcta ttatggctaa atatccttcc atctgaataa accgtgtaat taggaaaacc  26640
ttctacttgt tttttgttaa tcatccaaaa cttcctctct attatatatc tttaatagat  26700
aaaaagaaaa gagataaaga actttccggc aaagccggtc gccaaaggcg aaactctttt  26760
aatctcttga ccttaatctc ttaaagaact tatgttagta attaaaagat taaatcactt  26820
tactcggcaa cgcaagcaca aatactaaag ttcataccta agacctattt ttagtattag  26880
tgtttcgtta cggatatatt catgctataa tatgtatata agttagccac aaggttagct  26940
tagtgaaaag acatcatcac ctttcgttta tgtttatttc acacacctcc ttcttaatta  27000
ttttgtggtg gttgctaata tatcaactgc cacattatgg acagactagg ttcatagcct  27060
atgaagtccg ccaaatagta tgttgtgata ctagctttcg atactttata tatgtggagt  27120
ggagtttgtt gttagagggt tgtccgctcg ctactatgac aaacacataa ccgtaatata  27180
gaggacgtgg cagatgagat tgtcatgttg ccagacaagg gcttagtact tgctcgtcgg  27240
tctcggtggg agacgtattc ccatcctaat ctcacatcct gtccgcataa tggaagtaaa  27300
actggtctgt ggcatttggc tgtatgttaa cagcttatac ttgtgacgga aaaggtaagt  27360
tcacctcatg aagtagttaa tgggttgggt aagaaacgta ggtcttattc cttaaaagtc  27420
ctgtaaaaca aattaattag ttcataaaag taaaatcctt tccgagtatg taatatccag  27480
tccattctaa ttctgtacgc agtctatgga tacctcagcc cacgggtagt agcaagttaa  27540
atgagggaac aaaagacaag acgaagacgt tcgtcaccgt agaagtccta ctggttttat  27600
aactacgggc tattattttt gatacaagcc ttggacatcg cttactggcg taattaacca  27660
tgtaaattat attcatgatt tttccttctg gtaccgttgg aaagacaggt aataaacaga  27720
tgtccaaggc gtatatgaga aataatagga ggtaggaaaa tgacatcaaa ctatagtatc  27780
ttaacaaact tcgggtgtca ttggacatgc ccttactata ttgttaacga taagattagc  27840
catcgttacg aggatttcaa gggggaaaat aaatgaatga taatttaaaa aacataatct  27900
gttttttgtc tgaaaagatt atgaaattag aagaagaaaa taatgcttta aaaaaagaaa  27960
accaagcaat ttctgtttat agcgaataca caattgaaga gttacaggaa aagcttgata  28020
atgcttccca aggaaatgat tatgagctgg aagaagttaa gcgagtacag cgtgaagtag  28080
aatcgagcta ctcagtaaaa cttgcggagc tagaaacact tgttgaaaac aaatcagaac  28140
gtattaaaga attgtcaaag gcttgttcag atgttcatga ggagtattta gaatctgcaa  28200
```

```
aagaaaatgc ggagaaagat accaaaattg cagaattaga gaaaaagatt tcagagggtt  28260
tcgtagatag tgattacaac aaaacactag tagaagatta tgaagctgct gaaaaaatgt  28320
taacagaagt tactcttgaa aacttagaac tacagaaaaa gttagatgcc aagtttggta  28380
aagtagaata gcatatttcc ctgtctggtt gcagactgca agcccgacct aagcttccac  28440
aacctgctct tttggaagag taagtgtcga ctaaaacagt tgcatgataa gtgaagcgat  28500
attaggctcg tttgtataaa acattaaaga ggtggaatgt aacgggttct cagccctcta  28560
aaaataaatc ttatatattg tgtctgcaaa ccggtatata aaataaaaag tcctgtatag  28620
gcaaaggaga actacatatg gtaaaattag gtagcgaagc aaaagaagca ttatttgcgg  28680
aaaagaaagt aacaaaacga gtaactaagt tcttgaagca ggatgagggt attgtattac  28740
aatttgcagg ctttgaagaa ggctatgcac aagcaatgca acatcagtat tacggagtgt  28800
ggaaaggttc tagtgaatgt actggaaatg acttatacga taaagcagtt gaaatgattt  28860
atcaagaagc aaaagaagca ccaactggtt ccgatgaaga aaaacgtcta aaagacttag  28920
catatgcaat caaagctaaa ccagtgttct tgtttggttt ctgggaagta gctacaggtg  28980
aagaacttat tttaccagtg tcttctaaga aacaagctct agctctttac aaagcgttag  29040
aaaaacatga gaagaaattt ggtaagaaag cttttgaaat cgaacgtatt caaggtggat  29100
atttagtatc tccacttgac cttgacgaat tagacttaaa caacaaacaa gtagaagact  29160
ttgaggcaca tgtaaaagat ggtttcaatg ttgaattata cgatgaggct ctttggaaag  29220
ataacgaaga agcacaacta gaaaaacttg cacaagctgg aattgacatt gataaattaa  29280
tcggaagtgg acatggtaaa actgctacac cagcaccagc tggaacagaa ccattaccat  29340
tctaaggggg aactatcatg caagaaaaca atttatcttt agtagtactt aaattacatg  29400
atgatattga agacttagaa acttgtattc taggattgac tggtcttata gacgatgata  29460
agcttcaaga acttcttgaa ttgcttgctc cagtctatga agcagaaatc tttattagag  29520
gatacgcagc caaggattta gataaccatg ccaaataaag atgaaatggt ttataaagaa  29580
gatggaacta ttgatgtttc gagagagttt ctaaacaaca tgttagtact aagtacgtta  29640
gttaaattat ctacgctatt agatggaaca atgaagatgg ttgatgatgc catcaaagaa  29700
gaaactctat ctgaaacagt ttatgattat actactaaca ctatagaatc ctctttaaaa  29760
gctattaaag ctctactact catgacggaa ggtcttgata atatggacat tccagtcgga  29820
ggagagagta gtgatataga tgttttgtct attgttctag cactcgatgc ggtgatagaa  29880
gaagcagaca gagtgattga agggaataaa cttgtctaac actccacaag gcgtagatat  29940
tggggatatg gttagatata tgggatgtgg cggttgttct ggtcattata ctcatctaca  30000
aacatatgaa gtggttaaat taagccccca tctgccacgc tacttcttta tagtagatga  30060
tagaggtaat gaacatcttg taaagctagg cgtatacttt aaaattgcat aataaaatcc  30120
ctcaccatac ttgacggtgg gggatttttt tgttatacta ttttaagaaa ccttgtagca  30180
tagcagaagt tgttgtctca gcttggaaaa tcgctggata agttccagac acaagttgaa  30240
caccagaaat aagacctaca gctgtattgt ctgtagtagt tcccgaatgt gaaaacataa  30300
cacgcatatc cgtatcattc acatcgaact catcatcaac ggaactatcc cacgtgaaag  30360
catatctagt ccactcgctt gtaatgggaa caacttgtgc aagaatatca gcacccgggt  30420
ctgggttggc actttgttta cctctttgag ttctaaagat aacacggatg tccatttctg  30480
cggatgttga tacgttactt gttttagccc agaaggaaac tgtcaaagca gaagcattct  30540
```

```
ttaagcttgt gtcatacaat gttgggcttg ctccagcagg taagaagttt actttagcac  30600
gtaaatgtaa agattgatac caagcgttat tccacttagg acaaacagct aaactatacc  30660
cagatggaaa tggtgtttca attgaaagtc ttgcattaga ctgtgtccct gtcgagctgt  30720
accagttgaa tgggtttgta cgttgtggat ttggaagccc tgcttcattc gatgctgcaa  30780
agtctgtgca gattggaata gagtctaatc catcgttgtt ttggatgact tgaatttctt  30840
tactggaaat aatagggtca gctaggaagt tagaagctgt ctgtgctaat tgtactaaac  30900
cttcatcaac gatacggaag gaaccgccgt taatctctat tccagagtta tctagtgtta  30960
agttgctgtt acgtactgta acgtgttccg actgaataag aatatcatta gcagattgtg  31020
acataataga acctaagtta gtaccagtca aagctgggtc gccgtatttc catgaaccct  31080
ctggcggtac ataggattgg ttgacatcgg ctgcatatgt gcttacaaga actcctgtag  31140
tacttccgtc atccacacta tcttttaata atgaaggtgc aggactaacg ctttttaaag  31200
atgacttaag aagggcagga ggagcagaag acggtgctat gattgcttcg tcagctggaa  31260
ttaaccccgc atcgagggta acatttgtat cttgaaacat tgttccagtg aaatcatatc  31320
cacccatcat tcctgtaggg aaataataag taatagttac agaaagaatc tctgtggctt  31380
ttaacttact aaaatctaca agaaatcctc ttctaaccca cgctgtaacg ggtctttga   31440
atgtcaaacc atcactgtat gtaactgttt tagatacacc tgtagactgc atataagtta  31500
cagttactgt agttgtaacc tctccacctg tgacagaacc tctttcatac cagctataaa  31560
gcattttatg tccaaataat ctgttaggag agcggacttc ttgagtcatt gtatctaatc  31620
caattaaagg agatgtccat ccaagtgaac agtagttttg aatttcccct aatccttccg  31680
cttgtggaaa taccacagtt gaagctgttt gaggaaattc ccactctaga tattcagaac  31740
gaaaatctgc atttaacata atatttgcag aactagcatt atttaaactg tcattaagag  31800
aaaataattc tcctttaatt gcttcgatag caggaacatc ttgtacattt attggaataa  31860
atttaccgaa cgtaatttga ttattttctg gatttgtact agactttcta agttctatta  31920
cagtagcttc taaaccaagt ggaggattaa atgtattatc tttcacccac actgtgtccc  31980
cgttgtgaac gtcttctcct tggaatccaa gtgcttctaa atcaagcacg ttaactgtgt  32040
aggaaacatc aggttggcta cgtttcttta attcttcaat accttcaacc acaagacctg  32100
cttgtgtcac gccagaagta gaagaaacat aaagaccaaa agtattctta ccttccacac  32160
cccactctct tagagcagat ttagatacaa tataattatc tgttttagct ttggtgaagt  32220
tcttgtcatc tatgttagca gtgtatccaa ttagattagt tcttactcca ttaccatttt  32280
tctgtgatac tggaattatg gctgtacata ggttagtata atctaccact ctctctacac  32340
taactaaatc tctatcatat ataaagtatt taccttcatg tattggttta actgaataaa  32400
tattaacaac acgcttagta attttggtac cgtctgaaac acatgtaaaa ctatatacca  32460
catcgtattg ttcttgtaat tgaagcaaag cagctaaggc agtttgtgtt tctgtagact  32520
caaaaccacc tgctcccgct ttaatacctg aataatcttt gtatgtccac aacgtgttag  32580
atagtacagc tttaatacaa tcttggaaag tgttgccacg gtatggatta gaaaaagagg  32640
agttaagctc cgtcacttga attccttcac agtaaacaac tgccactgga ttagctctat  32700
cagagttttc atctacttta ataatagtaa ataaaagttc ttcttcgtcc tcgtcaacaa  32760
atgacaggcg gtttagacct gtcaaatatt gattaacaga agttcccagt ggagttgtaa  32820
atacgaatga tacctcacca gtttcagaat tgttcacata ttcgtcatcc cagtaaggaa  32880
caccgtctgg ggattgattt gtaagatggg cgacaatgtg cccggttctg tcgtaaatgg  32940
```

```
ttaacatggt ttcactcctt aaaatactct attatgatat tgaacagtca tatctacatt  33000
tgctggtgtt actactagat tattatatcc gggtattagt gggaagaagt cactagttgg  33060
gtcaagcaag gcaggtttca attgtccgtt aagatatatt tgaccacttt gcatatctat  33120
atctactacg tcatccttaa ctagatgaag tggtggcgtg gatgtgtctg gtgggtcaag  33180
aacttcccat acacgtatat tagcaatctt ggcagagtta cattggtttt tcttccattt  33240
tgagcgtgca ataacaatac caatttctgt tgcctttgta ttcatggagc tgtctggtgg  33300
aaggttaatc caaggagacc accaagtaga acgaagggca gatgttccgt agaagtagcc  33360
atctttaact tcatattgtt tagcattacg gaactcacca gctccccaac ggaatttacc  33420
attacgtctc tgtatcatta tcttaccata aaaatccgtc cagtcattac ttactcgtct  33480
taatagtcca tcaggtacag aaccatcatc aatacgacaa acaccttgac cttttagtag  33540
agaggagtac tctaagttaa cactgatgaa accttgtcca tccgcaccaa tcatagagat  33600
acaaatgtag ttagaagcat tcttatcacc tattttatga tgtaaatgaa gcacagcttc  33660
catatcaaag tttagtaagg catgtggcat agctgcttta ttcgctgctc cgtaataggc  33720
agcaatgtcg tcattagcag gtttaggcgg atagttagaa ggtttcatat aaaacgtgtc  33780
actagctcgt gagaaagttc ctccatattt aaatccttgc gaacctaaac cattaaaacc  33840
ggaagaccag tttgtccaac gtgtctcgtt tgcactcatg tagctttgga aaaccatagg  33900
gtgtaaattc acaggtggct ttggcttagc atccccgga ggagttccta cagttacatc  33960
cccattagcc cctactaaat ttaaatgagt tgaatcttct ttcatcgtga tagataccaa  34020
aggatgtgtg ggagcatttc cgctaacaag aatactagaa ggtttagtgt ctgcatttgt  34080
gaatctcctc tctattaatt ctccttctgc ggagttttga acacaaataa atgttaatgt  34140
ccctgcccct acgtgtaggg cttcttctat tgaagtggag ccatctaatc taaccttcca  34200
cacataatct gggtcatcag aaaaccttaa taacatatct tcgtctggat gatttaaata  34260
ggtagctaat tgtcttacac gtccccgaag taattcaggt ttatcagcta taataaatat  34320
atccatagaa atgtatctta cgtctgctga ttgtttatag aaataatttg ttgcccctct  34380
tccggtttgt tgataatttg aaacaatagg tggtagagca tcgtagttaa ctttttgtac  34440
ccctacatac caaggttgct taaccccatt taatgaaaat gttcttgggt ttgcatcttc  34500
tttaggagaa tagtcgaagt aaaggaacac gttacttttg cctgttactg ttgttgtatc  34560
ataagccaga acacttacac gaatacttcc atcaggatat acatattgtc ccgcatcaga  34620
gctagtttgt acacttgtgt taagaggagg tcttgatagt acaaggttgt tattttggct  34680
taccgaacta tttaaaacaa tatcacagtt agaagtatct gtaaccaacc cgcttggtaa  34740
cacagagata cgagttaatc ttgtttgtag tttagcacgt ttttcatctt ctgtaaaaac  34800
atctccaaag aaatcaggga aattctgttc caccgtgtgt actgcatcaa aacttattag  34860
aacttgatgt acttcactat ctgctgaatc tggagtaagc gttacaggaa gagcactaac  34920
tgttgtccat gatgtgtttt ctaaatcaag agtaacgctt ccaaaatctg tagtattttt  34980
atataaagta gtattagagg cttccacaaa atactctgcg aaagccggat tacctgtata  35040
tcctgccatg ttttaaaccc ctttgtatcg gttatttgta ttagttttat ttgtttgagc  35100
tcggctcata acatcagaag tggctcttgc aaattctcta ccattgatgt ataatggaac  35160
agtaatcaca ggagtagctg gattatttcc gtcatcgagt tcacgagcga tacttctagc  35220
aaatggtcgc atgtatgtag cattagctaa aggaagaacc atttcacgac cagcttctgc  35280
```

```
ataggttact ccgccacgtg caaatttctg attagtggtg ttagctaccg atttttgacc  35340
agtggaaaca ccaagaggca atccactagg agtcatacca ccatgagctc gggaaatcca  35400
attatctcca aagtacttat tctgattctt tttctgtaca gctgctttac caataccgcc  35460
accgggagtg ttaactactc cttgtactat attaacagaa gctgtgaatt gagctttgtc  35520
ccatttactt ttaaacgcat tcatcttatt ctctgcatct gatgtttccg cagaaacaat  35580
gatagtaggt ttagaatctt tagctccttg ttctagcttt tggattttat ccattacttc  35640
attatacata atatctgctt gacgaatagt ttcatctgct tgttgagttg catctgcaat  35700
aagttgtgcc ttggttctcc ctgtggcagc tatctgttca tcactcatac cattaattgc  35760
agctattgtt tgagctgctt gttccatagc tgcatttacc gttttattac gttggtcttc  35820
agcgtttgca attatcttat ctttggactc tttagaaata gtttggcgag aattttcaaa  35880
gtactcaatt tgtgctaaca gctggtcatt ggtaccttgt tctgcttgta aaagtaaggt  35940
atttttcttt gttcaataga ctgatactta gctaatgcag catttcttat tccaatatct  36000
ttagattgta aatcatttac taaagctaat tgttgttcgt tatatttcat cattaaagct  36060
tgtttttctt gattggaatc tttgactgtt tttatagcaa agtacttatc ctcatccgtc  36120
atattcttgt tcttctcaaa gaaggtagct aagatgtttt gttgtgaaga aagaccttct  36180
tgttgtgcgg ttagtgcact ggtgttcgca tcttttattg tctgtacttt tgatgcagag  36240
aattctttta acttatttcc ttccatagtg agggtagcta cagcaatctg cgatacagct  36300
tcatatgcag atttagaagt ttgtttatat gcttccatat ttccagaagt tataaattta  36360
actttattag aataagctaa aacagaacct aaaccagctt tagttgtatt ggataaggag  36420
ttccaagctt ttccttctac tccatactga gcagctaaat cttttgaacc ttgtatcatt  36480
ttagcatatg ttgttcgttg ctgttcggca cgagttaggt catcattcat agggctattc  36540
atctttttag tgccctcttc tttaccatat agctctatag ccttttcatc aaaaactttt  36600
ttatctttat agatactttc agcagatact aggtctccct tttctccttt atctttggtg  36660
cttttttttca ggtcttcgtt ctgtctttta gcttcttttg cacctttgtt aaactcactg  36720
aaagcatctg ttactttgtt aagtcctttt gtaaggacat caagaccccc tttaaccatc  36780
ccgtctattg attcacctac ggcaattttt aaagattccc agctagcttt cattctgtta  36840
atagagccct cagtagtggc acgcatcttc ttagcaactg agtctgattt accagcggag  36900
ttctcaattt tcttcgtcat gtcctcgaaa gcatccccac cagcgttcag tagttgtagt  36960
acagaaggca tggcagtaac gccaaacatt tgtgtaacca tcttagagcg ttcaacactg  37020
gacattccag ccatctcttt atttaaatcg ttgatgatag taccaatact tttaaattta  37080
ccagaagcat ctgtggcaga gaaaccaata gatttcatag cttctgcacc attcttagta  37140
gggtttacca aagagataaa catcttacgt agacctgttc ctgctgttga agcggaaata  37200
cctcggtcac gtagtaaacc agcagcggca gctacttcac taattgaaat acctagttgt  37260
tgagcgggtg cccctgcata tttaaataca taactcatat ctttcatacc tgctgcggta  37320
gcatcggaag ccatagcaag cttatctgcc acaccgccag cttcactagc ttccatatgc  37380
cacgttttaa gtgctgcgga aacggtatcg gttgtaatag ataaatcttc ttgagaagca  37440
tctgctgcat ttagtagagc aggtagaatt ttaatagagt ctgctactgt ataaccacgt  37500
ttagctaagt cagtaaatga ttcaccgata gactcagcac tgtgaccagt cttcttggac  37560
atgtcaaggg ttactgcgga aagttgttcg aatgttttct tattaccatt agagataacg  37620
ttagcatctg ttattacttg gttgaacttt gcgtatgctt ttacagagct gtttacaaat  37680
```

```
ttacctacac catacacagc agcaccagca ctggctgccg cgatgggtac gcctagtagt  37740
gatttagaaa gagagttaac attttgacca aaactttgca tcttggtttt acctcttcca  37800
ccgaagttgt taactcgtct attaacttca tccattcctt tattcattcc gccaaaggat  37860
gtttttgttg aagcccctgc tgcgacggct gccatattaa acttctctaa agaccttgca  37920
gctgcattca tcttacgagt aaatccagca gtatcagccg ttactactac acgaatatct  37980
gccattaact ttcaccgtcc atttcctttt ctttattacc aaacttagcc atagcttctt  38040
cccacatagc cttggcatcc tcattgcttt caggaataat aactccatta gctgtttcgc  38100
ctttttcttg ctctccattt gtaatcttaa cacccacaaa cttttctgcg gttggcatct  38160
tgttagtgtt tttcttggag atgtgtggtg acatttcata tagcattaat tccgcttccc  38220
ataaatcctt tttaactttt gctttttgta tagcagaata ttcagcaaaa gtaaggtcat  38280
ccaagcatct tgggtctatt cccatctctg ctaatgttac taccatgtta cgaacatcaa  38340
ggaagttctt ataaagcttt tcagtagggt cttcttcatt atctgtattt acttttaaag  38400
gtttaaacgg aacaacatct actacttgtg cgaatgagtc tgaatatgct tttgcaagtg  38460
ttcctgccca ttcttctatg taatctcgtt cttttgattc taagaattct aaagcccttt  38520
tttgaaaatc agcaaaaggg atatttctaa actcttcttg gtttataaac atagaccaac  38580
aaagtaatcc ttcatcgtct aattctaatt ctttccaatg tgctaatcct tctgcgtagg  38640
gtttctctgt tactgcttca atatatttag cagaacgtat agtaaaagat agttcatata  38700
gtttatcttc aaataaaatt agtctcatag ggcacctcat aaaataaagg gaagaaagac  38760
tgttcgtcaa tctcccctaa tctttagtat ttagctagat ggaatatcaa actgttcaac  38820
cgtagaccac actaaagtag aaccttcggc tgtcatcatt tgattagcag catctatagc  38880
tttttcaaca tcatctgcac ctgtacccac ataagtgtta cgagaagcag ctacagaaac  38940
atcaagtttc ttgccagcta aatctcctgt tccacctgta tcatggaaga taacatcttt  39000
taacaagtca aacgaattaa cttctgtgta ataaatacga tttcccggtg tttctccgtc  39060
aataccataa cgtaccatat aagagtccgc gtctgtcaca gcatcccaag ctaacttaac  39120
tccatctgtt gtaggtggag cagaggaagt taggttagca ggtgctgcta gcggtacatt  39180
agggtgtagg tactacaatt gtaactgttt gagaaacagt atttaatgca gtagctgtaa  39240
atttaactcc aaatgagcca gtcttaagtg gtgtcacttt gtaagcttct gttccagaaa  39300
tcttctctac tttcaagtct gtagcagtag taccacttac atactcaaat tgagttcctt  39360
gtggagcatt agttggttga atcgaagtta cgatttggaa aggtgtgtta actgcaatat  39420
ttgaaggaag agcacttgta gtcaaagtag ttgggttgac aattggtggc tctgtgtagt  39480
ataattctcc acgaccagta agtgttcctt cgaaagttgc aatgtcatca taagggaagt  39540
ctgagttgaa ggtagttaga atggctgtac catattccac accaccatca gggtaactta  39600
cttctacgct tacacattct ttgtttgtga aggctgcacg taaacgtttt tgaccttcat  39660
ctgtacctac taacagtcca tctaaatcaa tagaccaagt acgtacgccg tactctgaac  39720
taccccatcc gaaatcctct ttggagcttg catcaattgt atcagcttca cggttaatag  39780
taccaccacg ttgatagcct actgcaatca ttgccccagc gttgttaggg tcatctactt  39840
tgatgatgat ttctacgcca cggttaaagt tacttgcaca ttgtaccatg tattatttcc  39900
tccgtttaca ttttatttta gaactgtaaa agttacggtc acatacgctc tttgaaaatc  39960
ttgaacgcct acttgtgccc gcttaaaatc tatattagta gcaacaaatt tagctacaca  40020
```

```
atacccatca gctagttgta aagtagttcc tagacgattt atgacatcat ctgtaatctg  40080
tttaattctt aaggagccat ttttcgagtc ccaaatatcg atatggagtt ggtgtctagt  40140
tatttgtcca ctcttagaag agtcataaat taatgtctca tctccaataa caatataagg  40200
ataggtggaa tcgtgtcgcc aaccgtcaaa tacttcataa tctttattta gttcattata  40260
tatagcttcc tgtagtgcat tagaagctga tatattttca gaatatggag gaactgcatt  40320
tatatcagcc attaaaatcc tcctagaata ttactaattt tatcatcaat catgttagct  40380
atttgtggct ctataatagc ttgagcatcc tgtacgttaa agaatgcttg agaatgagat  40440
gtaccttctt caacatagga agcataagca actccatctt tagggttttt agaatcaatt  40500
ataatagata tttgagaaga accagttggt tcatacctca cactatcata catagcacct  40560
gtaagtatat taccattcgc agctatattt gacctaatct gttctacaaa caattcccca  40620
acgtcatcca ttgcctgagt tatctcattt gttactttaa taatatcccc taaaaatgtg  40680
tgacttccta ttacattaat accaaccatc tgtgccaaaa gtatcaactc ctttttcgag  40740
tttattttct ttcttgacat ctggtggatt tgtgttaaac tttggacgcg gatagcgata  40800
ctcgccaaca taactacaag tcatattttg tgataaatca tttaccaact cgtagtatct  40860
atccttccac actccatcaa taggaacaag accatcaata ggcacaccgt agtaacgtga  40920
ctctttatgt tgaaacctta catggtgttg ttgagacatg gtggcttgca taggaagttt  40980
tgtaataatt tgtgaaccac taatcgtacc acgaactgtt ccaacaactt ctaagatgta  41040
agcaccttct ccaccggtct catcaggaat ggaagttttg cgaactagtt gaaaccgata  41100
ttgtcgcttc atagcatccg caaccttcct tttccctcag tagggttatt gattccatac  41160
tgctcaagat atggaagcca gttcttatag atgtcagcaa tatagtcaaa ccttgttata  41220
tccgttgact ctaatttaag accttctgag tttagctggt tgtatcgttg agctagaatc  41280
tcatcagcaa taaaatctaa atccgcttct gggtattcag tataaggcac accaagcaca  41340
atacagataa ctttttgaat atggcttttt agaattgcta aaaccaagtc ttggtcatgc  41400
tcatcagcgg gtaaacctat aataactttt atagcttcaa tgtttatatt tgcatactct  41460
ggtggcatat actaacctcc catctgccac aaaaaagggg agaaagacga aatgtcaatc  41520
tccctctctt agtctcttat tatgattaag atactgtgac agtgtgagtg gcagtaatag  41580
aaccatcagt attggatact gttaatatat atttacctgc tggcacgtct gttccagtat  41640
agttaacttt taagccatcg ataatagctt ttatagcact agaatcagca ccatctttat  41700
ctgtaacctt aacttcaaaa gcttctgtag catctgtagg gtctactgca actgtaaagc  41760
taccagttaa tgcaccggaa gaagatttag aagacgtttt aggagaaaca gttaagctaa  41820
caatttcttt attactagaa gaacgtaaca ttgaaggact tgcagatggg acatctacag  41880
taactaggtt agaccatgca gttacttcat tgtattctgc actttctaaa gcagaagtgg  41940
catccgcgta aactccagca aattgtgcta catatacgtc aattttctta ccagcgaatg  42000
gagctaatgc tactactaca tcctcagtag ctgtaaagct attagttgta gttacaaaaa  42060
cattattatc tggcaatcca tctccattaa tgcctaaacg aacaacatac gttttagcat  42120
taaatcctcc attaccccaa tcaatagtga aagaatcaga ttctaaatct gttacattaa  42180
cattaatagg agcaggtgga tgaatactag tatcagatac cagtgtttta acgttaattg  42240
ggtttgtcca atcacttgtt ttaatactga cgtcactacc agtagttgta acttcatgac  42300
atctaactaa atactggtag ttagtattag gaagaagatt atcatctctc caatttccag  42360
cgggaacata tgtagctacc acattgccgt tacgtttaat atcatatttc ttaacggttg  42420
```

```
gcatttacta attcccctta cttagttttg acgttaattg gagcagtcca ctcagaggta  42480
gattttacta caccagagtc tacctcacgc acacgtactt ggtattggta gtttgttttt  42540
ggtaatacat cattatccac aaagtcacct gaagcatgga acgtttcgat aatgttacca  42600
tttttcttaa tatcatattt cttttctaca gccattgatt tattcctccg attcgattat  42660
aatagactta taacccagcc gaagctgggc ttagtcttta ttaggcaggt aaagtaattg  42720
taacagaaga agcagttgta gcaggagtcg caatagttgg agccgctgga acagcagtgc  42780
ctgcacctac ataaacaatt ttatcttcat cagccataaa tgtagcatag tggcggtcac  42840
cacttattaa tgtagtgtga gaaagtaaat catattcagt aagaatacgt gtatcttgtt  42900
taagagcaat accaagagca ccagctttaa tgaagaagaa ctcaccgtct tgtactttat  42960
cagaaagaac tacagtacat ccataaagag taccgatagt accattgatg atgatagaac  43020
cttgattaat gataggaaca aacttatcat cagaaacgaa caaagcataa ctgttagtgc  43080
ttactaaaag atatgtagca tcttcgtaaa gagtttcacc aaagttagct aaagctaaag  43140
gaattttgtt gattgcatct acagtaagag ccgctccagt tgaagggtct acagcttttt  43200
tagcagaacg agcaatagca attaaatcat catctacttt ttgagctaaa gccattgcga  43260
tttggtcaac aatttcatta acagggttac ctgcggaagc tagttctagt tcgtctgaga  43320
tagctacagc tttaacagct tttttaactg ttacagagat ttgagattgg ttaatagtgt  43380
caatattaga agtttgacct tctgcaacaa cttctgcttt accaattttg ttccagttag  43440
gaagagtgat tgtatcccct acagaacctt gtaattgatt gaatgttgta gctagtggtg  43500
caaagcgaat atactcgtac attttctttg caaggtatgg accgacaact tgtggtacaa  43560
acatattttg taacattgtc agtggttggt aaggtgaatt agccattaat aattgactcc  43620
tttgtcattg tatttttatc cttgaagagc agtataaagt tctggattac gttcatataa  43680
agatagttgt tcttctaagg acattttttc taacgcttct tttgtgagag agtcatcaga  43740
cacaccacta tcgttagaac caccaccagc aggagatgaa taagcacctt ttaatttagt  43800
gtcaactcgt tgttgaacca atgcgataac ctcgttctgt aaatcagata cccgttgatt  43860
aacggcttcg gtcgaatcgg caataacaaa gtcggctaac gtaggagaaa gctcacgttt  43920
agataattca cgcactgcgt gagttcgcat aacttcttgt tgagcacgtt gctccgcacg  43980
ttcatatttc aattccagtt ctcgaatgcg tttttgttca gcagtttcag acggattggc  44040
tttggctact tcctcgctaa taatagtttc gaggttattt gttttccaag tctcaatacc  44100
tttagtaact tttgaatcta taataggtgc gattaaattt ttaccgctct ctgtttgaag  44160
gtattcattt acagtgtcct tattaaagaa cgcacctcgt aaatccgctt caagctctgt  44220
attttgtttt aggtgttctt gcaattctgc aaaagataat tggtcttcga taggcatttc  44280
tttttcccct ctcaccttta gagtccaatg tcctccaaag tttagatata ttttcctgtg  44340
ttggttttac atactataaa caggtactat agtacaacga caaaaaggat gtacggggat  44400
aactggaaca ctatctttat catagattcc gtctccgtta atccctccgt tttcaagttg  44460
tctacaatgc ttacaaggtg cattcttaga taactccggg gctgtcgtat attgataata  44520
cataacactg tttgcagtac cttcgtcata gatagattgg tttactgctt ttgctgtgct  44580
agttcttatt gctctcttag cttggtactc agcttgggaa aaagctttta atgcttcttc  44640
tcttgcttct tcttcggaat atccctgaga taagctacgg tgtagtaaac gtgttatagt  44700
aataataaga gctgctataa taacatttag tttgttagaa tggtctaccg ccttgtcctc  44760
```

```
aaatgagtcc aaagtgttag ataacttttc ttcccccata ggtacagtag aagaccctat  44820
ttgttgcatt tttctgaata tttttctaat cgcttcatct tgggcaattt ttacatcgtt  44880
ttggtactta ataactatgt tctgcaacaa cctatttatc aaataaaaag cttgcatacc  44940
ttcaaaagaa ttgatataat tattattaac ttctccgttt tcatcatatg ccttggagag  45000
gtaagttaat acctcatcca aaacacgttg aaggtctact gatagctctc catccacttc  45060
ctcaatccga gacatcgcat caaacatcat gttagcatat tgagcttctt tttgtggagt  45120
aacttttgcc atctagcatt acctcgcttg tctttgtttt tcttgtgtcg ctgaatcttg  45180
aacgtttgta ccttgtgcat tagtagtaat tccttgtttg gcacgtccat tagaattatc  45240
atttgcttta acattcgaag ccgtcatagt agttgttgcg ttttccgcta tagaagtttc  45300
tgctacaaga gcaatctctt cttgtttctc aattgcaacc tgtttcattt ctttcttaac  45360
atctgtaacg aaaggaattt gatgtaacag agtttcatta gaaacaagtc cacggaactt  45420
aacagaagta tcagcaagtt ctgcaagaga agcaggtaag caacgagtaa atactggtga  45480
catgtcttta gcatctttaa gagcagatga tttaactgca attaaggtag ctattaagtt  45540
aatacgttca tgaagtccaa tctcaaactt acgttgttta gctgatgttt taatctcaag  45600
attattcaag gcatatttga tggcaacacc agaaaggtta ttagcagttt gcattccatt  45660
agtatcaggt gtgaaagatt gttccatgat ttcttttgtt aaacgattct tgatgttctc  45720
taagtgtttg tcaggggttt gcttagtaat aaacttagca tccccgcctt ccactagaac  45780
cattacacgg ttttgtttca tggagcggac gtcttcacta ttagtaccgt ccatacctgt  45840
taacataagg taagcatcat tccagtaaga gacatcattt acactatcac acacaactaa  45900
gttaagtgca tcaacaagtc caataactgt ttcgaaatcg ccaagacgtt catcgttagc  45960
taagtactca atcataggaa cttctccaaa atagtgagga gttactttct cattgtatat  46020
tagattatta gatgactctt cttctcccgt tgcattctct tctgctacag aagcatcccc  46080
gccaccaagt gaaactttga attgtagaat gcggtctgga tagtatacag taacacttct  46140
tcgcttctcg gaagagatag catccgtata atcgttatat acaacgccac acagtttgtt  46200
ctcatctaat gtagaatcat atacgataaa agcgtttgag ggagcttcat atttgaatct  46260
atggttggcg ttcttatctg tccaatgaat ctcaaaagcg tgtccataga tagatactaa  46320
tttacctaac tcagaatcaa catcagtaga attattagcg ttcataacat ctgtaacttg  46380
tttgatggtg ttgtcactcg ctttggcata tgtaattgca ttaccagtaa agtacgagtt  46440
agcagtctct acaatcagtt taggatagtt atgtacaagt ttattatttg gtttcaactt  46500
atcattgaaa gttctcttta aaatatcgtg gttaccaata tagtaatcgt gcagatattt  46560
gtagatgaac ttacgctgag aatgccgttg aattagaaga agtacgcctg caatattagg  46620
ctcttcatct gcaataaact ttctattaaa tactactgtg ttaactcgtg aaccccgcgg  46680
aacatagtcc gtaggctgag aatctgttgg aatgtttaca ccattattag ccatacgaaa  46740
ctccatttct gcaagtattt gttcgtctct ttctcctgct tttaccattt aaattcctcc  46800
attaaacatg aacttactga ttagaatcca agtgccgact taggtatagt ccgtgctcta  46860
ttacgtggga ttacttcttc caacgcataa cgcaaggcat ctaagccgtg attgtattcg  46920
tcaataggtt tgtttatata ttcgtttggg ttttgtttgt ctttctgcca agcatagttt  46980
tcaagttctt ctctaatgtg agtacatcga gggtggacaa taatttcgaa tccttgcaca  47040
aattgaatac catgtacaat tgaatcttta cctttacgag ctgctttgat tctccatata  47100
cctttacggc gaatctcttc aatagattta ggctcagaac tatctgctac tattttctct  47160
```

```
ttagcccaac ctttctcagc tatcttgcga acaatatcat cattgagcat tcgttctttt  47220
tgtttaatat tattttggta ttcatcgtaa atataaatct tcttgttgcg ttcgtctaca  47280
atacaagcaa ccatcgctgt agcatcattg gcgtaaccaa agtcaagacc aaagtaagac  47340
tttaatccag cacgtttgag ttggtctacg gttgggtcaa tgttttgcat accataaggg  47400
tcatggatat taggaatctt ccactctctc caattggtgt agacaagctc accgagagaa  47460
gcaaagtctc ccatggcata gatacggtgg taagtcggat ttgttttcat aagctcttct  47520
aaagtattaa gatacttttc tggtaagaac ttattatctt tgtaggtagt atgtagtatc  47580
cttaaatctt cgggacgttc atctgctgta gttgggtcat gaaataatct atatacccag  47640
ttaacttttg agatagggtt ataacagaga atcatctgtc cctcttttct ccgtttacct  47700
gcaagattac gcatacgtag ttgaagctgt gtataatcat ctaaggtaag ttccgttgct  47760
tcctccaaaa atatatcatc aataccagat atagatttga ttttctccgg gttatcaatt  47820
cctttaaata gaatttgaga accatttgga agaacgatac gaagttggga agtgtaaatt  47880
ctacatctat cagcaagctt gaatgttgat aaagctttag taaattctga aaatacagaa  47940
tcccgtaaag agtttgtatt ctttctaact actaacatct ttcttttttc tcgcatcaag  48000
cgaataacag aacgttgtac cgcccaaaca gatttaccag aacccgctcc accataaaaa  48060
atgatagtac ggtcattcca ttctaaacta ggtaggtaca ctttgttaaa cattcgttca  48120
tgaatattta atgaaatatg ttctacttgt ttctcctgtt tcatatgtat tctcctttat  48180
aaaagtaacc tccaccttat attatatcat aaggcagagg taatgtcaag cattaattct  48240
gaacattcgg aaaatttcct gctccgttgt tgctaatttt tacaccagtt gatgggtggc  48300
aatatacttt gacatgtcca aaggaaccag tcttaattcc tagaacatta tctccgtaat  48360
tcttttcgac tttgtaagtc agtccaccaa acttcgaagg gttaattgct ccgattgcat  48420
tagcttttac aggtgcttta tttaatggat acacactcca agtaccttta ccagcaggga  48480
agtatacgta catcccagaa gtagctggtt tagccggagg ttttggagta gcgtgttttg  48540
gtgcacctgc tttaatctta gctaatagtt gtgtattctg tgaagtggtt cctgtataat  48600
tcttgatgcc atattttcca gcaagtactt tacgattagc aaaagaggaa tccattttct  48660
tgctgttcat gtaatctacg agaccaagtt caccagaagg cttcgcaggt gtagatggtt  48720
tggatggttt agcgggagtg ctggagttag gacgttctcc tcctacccaa tcatataact  48780
caaaatgagg gttgtcttta aaagatttcc aatctccacc ccatttgaat ccttgtttct  48840
tcatggcagc tacaatcttt ttaaacttag catctaccgc ccagattaca tctttaccat  48900
cttgcgtgta ttggcataag tctacagcaa caccgtagtt atgatttgat tgacctccct  48960
ttgcatttgt taccacattg ccgggctttg ttctgccttg tgcatataat tcattctgtt  49020
ctgcaataga acggaagcct tgtgcaacat tgatgtaaat accttgttta gccatctctt  49080
taattactgc acgggtttta tctgaaactt ctttaagcat cccttttttcg tttaaacgtc  49140
tattggcttt ttcaagaagc catgcttctg ttaatgccat tatttatctc cgtcctttcg  49200
aggttcagta taatttaaag ctctttcgct gtcgctaaat ccagaagttg tagggtctac  49260
gtagttagca ataagagctg tgataaccgc aatgatagct actggcttgc ttatgaattc  49320
gcaaaaggca ttccacaata aactccaact atctaaatct gatacttgaa atccgccagc  49380
agaccacaca attgtaagaa cagctactgc ggataatagc catgttcgcc agttcttgaa  49440
tcttagtttc cagttaatat tcatcgtttg tatccctccg tgtgttttac ttctttaata  49500
```

-continued

```
tcttcttcga tatagtcaag acgtgtttca atcttatctg cacgtccttc tatcttatct  49560
actctagtat tggttttgtt aatgcggagg tgtatttgca ttcggtcttg tttgctttcc  49620
tccaattgac tagctaagtt atccatgcta ctagttagat tatcaaatct atccataaat  49680
ggcgatgcta caattctctt gaatagccaa gctagcccac taaacaatcc cgtaactagt  49740
ccaattaatg ctacccattc tgtaatctgt agtccccaaa taactgctcc tatctgcata  49800
cttgctccca cttccatctg tattaatact ctaatacttc ctctagccgt actctatttg  49860
accagtttgt agtattggca ttgttatcgt gacctactaa tcggtcattg tatagtctta  49920
ccatcttcac tattgtacgg ttaccagcat aatcctttac agtatcgttt gaatatgcta  49980
taactgaacc tacagtaact ccttcacgag cttctacatg tcgtttaggt acgtaagtgt  50040
aggtgtagtt tatgttagaa gaatcccacc tccaaacaag gataattcca ttacgcatat  50100
ttgtgatatt cttaccaaag gtaactgttt gacttgcgtt tggatatacg ttagtgttgg  50160
ctttaagaac acgtgaagac catacaacat tatctgtgta tgttttcgca tttgctgtag  50220
ctgttgttat ggcattttgt tgagcagtgt tagccttcgt tgtagcgtcc gtagaggcaa  50280
ctgattgaac gtttgcatct gctgtgtcca tttgctcctt agaagcataa gtgaaccaag  50340
gaagggttac gccggacgtg tcaacgtgca tctcatacgt cacactatct ggtacagttc  50400
ttaatactaa aatctttgtt ccagattttc ctgttgtaac atctaattga aagcttacag  50460
cggttgtggt tgttatctgt ggtgggaaac ctatagttgc tttgtcagcc aatgaagcgg  50520
gagaaacacc ttcgtatagc ttcgcatcta atgtaggtag tccgggcgat agtgctgtca  50580
atgttcctaa atcaattcta gttccgttag catttgtaaa agcgtacggt tgatagtttg  50640
taatatctgt tttaagaact acttgattgg catcaataga agcttgtagt gcctttactt  50700
ctgtatcaag tgttgctaca tttccagtca atgctgttac atcatcagaa gtattatcta  50760
gttctgtttg tacatctgca agctctgctc tgatagcatc tttgaaagct tcaatatctg  50820
atgtaaatgg tggtgtttgc atggaattat ttgttgcatt attttgaata gttagagaga  50880
agttctgggt agtaacacgt ttgttaactg ttccaacaag ttgctctaat gcaaagtatg  50940
cctctggcat gtatccaact tttgaccaca cttctttaat aaatgtgtag cggaatattc  51000
cctgtgaagc atctactatt tctaagttct gataaacaga accgtcatca cgtacatagt  51060
taatttgttc gccgtcttga taaggaagac gacattcaaa atagattgaa tagccagtta  51120
aattgatagg cagtccagtc ttggttagct taactagaat agacgttaaa tctctgtcgg  51180
caaggcgacc tataactctt tggttttcat aaggtcttgt tacgtctagt ataatgtcat  51240
attcttttac tgcatcagcc atttgtcatc ctccttagtc aatataaaat tctattggcg  51300
ttaaccaaat accttgtgtt ccgttaccat ttatccatac aacctctaag ttacctgcac  51360
tgcttacata aacctctgcc ataaagttaa caccagtggt ttgacgtgca catatccaac  51420
cattttgatt acctaccatt ggacgataac cagcaggaag tgttgcgata acacctttct  51480
tagcagcggt atccatgtga acaactccac gtaatgaaac cttattacct actttacgat  51540
atgccggagg gtttgtagca tcagttgacc atccagaatt aaatcctgtg atatttatcc  51600
agccagtatc tcgtgcatct tgcactctcc atcctcgcca cactccgcta tttagttggt  51660
tcattaccat agtctggttg gagcctactc catataaatt cccccaagta ccttgtacct  51720
caatataggt atatccccgg atggtggtag gaggaacatt agtattagga tttgttgttc  51780
cagcagtacc agaaattcgt gtcatataca taccagccgg aactttattt agctctgtgt  51840
aaatatctaa tccactgtcc gtatctagat ttactatagg aacaccgcta ttatcaaata  51900
```

gctggatgtt ctgcatggaa tccattctag tgtttaaggt agaaactgcg gttgctaatt 51960
ggttagcaac atcagacatt gtggcgttct ctttccaagg aagtacccaa ccagctgttc 52020
catttaagaa agttgaataa gagtttccaa aggaatccca tccaattacc catccggttg 52080
tagctgttgt tagatgagaa attcctctta aaggagtatt agccgttggg ttatttacag 52140
cacctgatac tgcatagaat gttcgtaaac ctattcctgc tgtttttata atatcaagaa 52200
tatcttttga agtgtctgag ccagttgtaa gtaagttggc acctgtgtca tcagtaatct 52260
tctgtttctg ccagttaact gcatcagctg ttttgattac ttggttagct gtaatcagtg 52320
cttctatctc atccatctgt gcactagcat ctgccacatc tgctttcagt tgaaccattt 52380
cagcaattac aggagcaagc ctaatttcaa tctcagcttt aagcgactca atgtcagaga 52440
tgtaatcgtc agcatttatc tttccttcaa tagcactatc tgttacaatg attttaaagt 52500
tacgagttgt gacacgtttt acaatatcac caactggtgt ttctaaagca aaataggcaa 52560
tgttaatagc ccctactttg gagaaagtct ctttaacaaa gttgtattga atgattcctt 52620
gttcggcatc tacaataatc atattgccat ttgctatccc atcatcacgg acgaagttag 52680
catactcacc tgtttgtgcg ggtaattgac actcaaatag cggggtacgt cccactaagt 52740
ttattgcttc tccgttgttg gttagcttaa ctaatacgga tgttaaatct ttgtcagcaa 52800
tgcgggatat tagtaccacg ttttcagtat ctttaactaa gtccaatgct agagtgtatt 52860
tcttgtcagc tgattttgga actggtggat tagcttggct atagatagga acaggacatc 52920
tcgcaagctc tttagttcca ttatacataa tcattgtaac cactgtggtt aatgtgattt 52980
gagatttgat agtggaaacg tcagccataa aggttgtccc attagtgaat cctgcaattg 53040
catttaagtt agtatcagtt ccgttaagta atatcttaac agtagttaat gtttcgtcta 53100
cctcgtaaac gccatgaata aaatcatccg tgccgtcaaa ggcgtaggag tttgccatga 53160
tatagttagt cattcttaat cctcgccttc ctcaatagag taatcaaagt tatcttgcca 53220
gtcgtcctca tcgtcctcgt cttcgtcatc tccaacaata tccacggtaa taactgtttc 53280
gactttgatt tcttgtttct ctttccacat gccataggat ttacctaaca tctcagcagc 53340
tttattctta tcgacaatag aaggtttctt attaaccttt tccccttttg cagttacgaa 53400
ttcttctcct tcttctcctt taacaactcg tgtataatat tccagaatat ctttttggtc 53460
tgcaattgta ctgttagcat ttgattctgt aacatagcgt aggtaagctt gattttcttc 53520
tttagccaaa agtgtatgtg cataaggtct tgtatatcca gactctctcg cagcacgaga 53580
aacattatgg tcaactagat attctctaag taaacgtttt gtcttaggtt taatcacact 53640
aaatttttct gggtcattat aaatgtttaa cgccacaaac tttcactccc tttctctctt 53700
gttctttttt ttggaggtat ttcttttttta ataaaagaca cgccagtgtc ttataaataa 53760
gtgtagcccc gtgcaaaatc tttcgataaa tctttaaact ttactcttct ttagttctat 53820
cgagtaagaa gaacctttac tctttaaaac atgtaaagat acagtttaga ccccctttt 53880
gttgcgtttt ctgggaaaat aactggtata agtgtcatat taatttattt tgaagaaaat 53940
agttgacaat tagaaaggta cgtgctaaga ttagtttata aattattagg aggagatata 54000
aaatggctga tgtagtatat gcggaatgga actggtcaga agaccaaaca aaagaagaga 54060
tggaatatgc tttagacttg attaaagaaa tggttggaaa gattaataag aaggaacaag 54120
tagaacctat tgatattccc gctttggttg aagaaagatt ccacggaaga agtgtagaga 54180
aagctaaaga tgaaacaact attacaattg attccacaag tgaatctaaa tggaatcctg 54240

```
ttttggtaga attggagaaa ttcgctaagc gggtggagga aaaggattat attgtgttgt  54300
ctgatttaac aagttggtta gaaccaatta acgaagtatt aggaacagat ttaaaatacc  54360
gcagagaggg aatgcgtatt aatcgctagg tgataatatg aaacgaattt ataaaatgtg  54420
gattgaacct tttgtcggta ttgcaatttt tatgttgcct ttatttgctt ccggaggaga  54480
agaagctact acaggatggg aagtagcttt agcgtttatt ctttcactgg gctatgggta  54540
ctttgttggt agacccatgt tgtattactt tttatttgat ggagtaaccg cagaagcaca  54600
caaaagagaa attaatagct tacgaaccta tattaatcaa tgccaagaag caatgaatgc  54660
tagtggtaaa acatgtagag acctaaccga tagagttgtg ggtttatata gctccaacaa  54720
agaactttg gatagattgg aatatctcca aaaagaagca gaaaacttac aagaagaatt  54780
gctcatgtta cgagaagaga atgcacaatt aattatacag gtaaagaaac atgaagagta  54840
ataaaccttc tttacttggg gcatgtttga cagatacagc aagtggaaaa gaatatcctt  54900
atgaatttag ggcaacacat catttaataa gagttttagt ttcctacaga actaatatag  54960
caggtaagcg ggagttttac gttagattgg aatctattaa ttattcggat ggctgggaaa  55020
taactcctta tgatgaggta tatctaggag aaactacttg gggttgagag gtgttaacga  55080
tggaaacaaa tttgccttcc ctatcttctg ctcttttgca tgacttagca tgtagtaggc  55140
aatatgattt aagatatgta gatgtagtta acgttacaat aacaatgtgc gaggacactc  55200
ctactagtaa agaatttttc agtatagaat tagaaacaaa atataaccgt aatatttgga  55260
aatttggaga aggtagatat acagtagttc ttggagaaac aacgtggaag tgaggtaatt  55320
ataaatgagc aagatttttc catccctgcc aacggcacat ttacagtatg atagctatat  55380
tggtgctcat ccttatgaga aagatgtaac acataaaata ataagaattg ctattactaa  55440
agataataga ttagcaggtg ttactgaatt tgatgtcatg atagagtctg aattaaactc  55500
tcaggcgtgg ggcaagagtt atgaactagc taatgccata catctaggag caacttattg  55560
ggaaacggag gaatgagtgt gactaaaatg tatccgatat tagataatat cgtaggaaga  55620
gattgggaag gtgactggct tcgtattgca aatatgtcaa actacgggat aaccaatata  55680
aacatatttt tggatgagga gggagattgg aatataaatt taattagtac ttctttggag  55740
gagtttgaag catgtttcca atatattgaa tctattagta ttatagattg ggaagaggtg  55800
gagtgaccgt ggttaaaatg tatccagtat tagcggatat tgtaggattt tgtagggaac  55860
taagaatgtg tggaatgcgt cttaatgacg gtcatggggt ttctaaggta agcatagagc  55920
tcagcaacgg taattggagt ttgatcgtag ttaaaaattc aggagacggt aacggaataa  55980
gttttatgag tattaatggt gtagaaatag tagcttggga aatgaaggag gaaagaggat  56040
gagtattaaa tattcccttc caaaactaag agtaggggaa agacttcaaa gtggacgtaa  56100
agcaattttt gatttccctc aacgcaataa aaagaatgtt acaagaataa gagtatggcg  56160
aaatagtaaa tcaggtaaat tgcgagcggg agttactgga gacagtggaa gagaagagtg  56220
gtgtgctttt ttagaagaag acgagactat gttatatatt ggagagttgg tgtggaatga  56280
gtaatgttaa attttcactt ccagacctgc gagtaagatg ggttgataaa atatatgtgg  56340
aaagggaata cttatttgac aaagcagata caaaggacgt tatacgaatc aaactaggaa  56400
taacctcatt gggtacattc ttcttacaga tagagccagc agatggaata ggtgattata  56460
ccagcatttc acgtgcagaa gaagaggttt tatttggaga ggtgatttgg aatgagtgtt  56520
aagttttatt taccgacctg tctagctgaa tggttagatg gacatggaat aataaggaca  56580
acccgtttta atccaattaa tactaccaat gtagttaata ttactgtaac taaaagagga  56640
```

```
aacgggaaat tgtacttgca tgttaatgga gataaaacaa cttcatatga agaggataac  56700
atggctctag gtgagcaagg ggatgttatt tattggtgaa gaactgtgtg ggaggattag  56760
atgtaatggg taaaattgaa atgtcttttc cagagcttag tgtgtctttt attgagttta  56820
caggagatag aggggttgcc ggatggaatt caccaagtac tcaccatgta aggcgtataa  56880
cagttatgtg cctagatgag cagagaggca ctgttttgat aatgactgga caagatgaag  56940
aagaagattg gcaagcaata gatgaggacg gcgacttagt tacttgggga gaaaccgttt  57000
gggaggaaga tagttgacag tctttctcct ttttggtata cttaaatagt aggaggagat  57060
tatatgaaag ggataggtta tttaatagat tgtattagta acaatttgtt gttagaactt  57120
aaagtaattg aggataataa atttgattgt tcatgtttaa ttacgtactg gaatgaagag  57180
tacggaacga ttaatacttt tagatttagt aattcagata caattttgag agcgttgttc  57240
tatgttaatt acagaaagga taaggcacag attggtcacg agtttactgc tagtaggaga  57300
ggagcgtttg taattgaaac aacctaaaca aaagtatagt tacgtgtata caagagatgg  57360
agaaaaagtt acacatatta gattatacaa aaaaccaagt agtgaggaga tattgactat  57420
gtttaaaaca gtatctggat gtagagaaag atattacgtg gatgagccta taagatatgc  57480
tttaacaatt tttatatatg attgtatagt gaaataaagg agagtgcgat atgccggata  57540
tatttgatag cgtagacaga tttgaagaag aggataagag agttttacga attgagatac  57600
gttacttggg aaataccgga gcatttaaaa gaaaattctt gtatgacaat ggaagacatt  57660
catatgcagc taatttgtgg gaagaagtgg cacaagagtt attctatgca ggaataactg  57720
atttgtacat taaagagtga ggagtaatta ttatggatag caaactttac aaccacgtta  57780
ttgcagagga tattagcaca gtatatgaag tagttattaa aagagatgtt aatggtgctt  57840
ttgttatatc ctatctttat gttattaact caatattaaa tacaatgagt ggaagagtta  57900
ctagaggtaa gttaaatcgt attaataaaa gtttgcaggt tatctctact aaaatgtgtg  57960
ctttacaaaa ggaagagaaa tatataaggg aatgataaaa acaaatggca aaggtttttg  58020
atactaacaa aaggtaccgt ataacttatg agagggaaga agtagtaact attaagattt  58080
tagagaaagg aatatttcgt ttagaaaaga tttatcaagg taactggggt ggcggtattg  58140
ctgtagcatc ttgtgaggaa tttttaaatg atttaaccgt aactgataaa gaggaggatt  58200
taaagataga atgaaaaact atagagtata aagaatagaa tccaaagatg cgaagccatt  58260
tatattaggt ctacattatg cacaacgtat gccaagtatt tcctacgctt acgggatatt  58320
ccttggagaa gagttgctgg gaatttgtac cattggaaaa cccgccagta atcctttatg  58380
tgttggagta tgtggcaaag agtattcgca caaggttttt gaattgaata gattgtgtat  58440
gaaggataaa ctaggtaaga atgttttgag cttctttgtg agtaaagtgc ttaaagactt  58500
gaagaaagaa aacctcatct taatttctta tgcagatact ggtatgaacc attctggata  58560
tatctaccaa gctaccaact ggatgtacac gggattaact gctggaagga cagataaata  58620
tacgccagag aataaacact ctcgacacta cacgaacgag tttaaccact tgcgaaaagt  58680
aaggacggct aagcatcgtt atatctatgt ggcgggagat aaacgttttg taaaagaggt  58740
taaaggaaag attaggatat taagaacaac catatcctaa agatactaat agtgattatg  58800
agttaggaac tcgccagaaa acaaagatac ttaacacaga ggataatacg gtgttttatc  58860
agtaatttat ctgtcctagt tgacattgtt ttaactttgt ggtaagctct tattataaag  58920
aaggaggaga taaatatgaa taagtatgaa agatatgttg taggttggta tgatgaagat  58980
```

ggtgactggc actactgttc gagccgtaca ggtgttttaa aggaaaccgt aactgaagct 59040
aacaattgcc gaaaagtgaa acagagacat cctttataca aatataaaag tttggagatt 59100
ggtacaatgt actttgaggg tgctttaaat gaagaacttg ttaaaccaat tattgcagaa 59160
gagaaagagt atgcgattcg ccgtcacgag ttaagagatg aattcgaaac aattgctaag 59220
gaaagaggat taaataattt tgggactgag tttaataaag cttttgacga atggatagca 59280
actaaggagg attaaaatgg actgctataa taaatacaga gtttgcgtat tttatggaga 59340
aagagattac gaatttttct acattgaagc atacgacgaa ttttatgcta agttagatgc 59400
tatggatatg tatgctaatt tttcacgaga gttatactac gatgaagtgc ttccagtttt 59460
ctctgttgaa atcgaacaag tagaggagtt ttaaaaatga gaatagtatc agcaattatc 59520
agcacgccaa aaatgtatat ctatgattta catcagatag ataatcacac aggattagaa 59580
gttattatga ttgaagaacg gggcaatgga gttattatta cgtttaatga cggctctgct 59640
cgcaagttca gaagtgattg ttatagtttg ttttatgagg gagctgtagg cttttgagtt 59700
ggcttacaag aaggaaaaaa gatgctagag taggagagaa ttatgttcct aaaacagtgc 59760
caatgaataa tataaagaat ggagaagcta aaatgccaga acctattaaa gaggtaaaaa 59820
tagaattacg gtataaaatt ggggaagaga tttactattt aaacccagaa actaaggaac 59880
gagagttagc caaagttttg ggatttggag tagaagaaga tagtaaaatt cagtattacc 59940
atatctctac tttggatgaa cctcagaagg agcttaaggt atatttaaaa gacattggaa 60000
aagtatattt aaaagttgaa cacatcacta ctttggtgtt tgtatacttt gctggaaaag 60060
aaattaagta cattcccgga gagaactgtg aggatgttgt agtaggaact gataaagaga 60120
atgtttatgt ttcttttaag gatggaaaga ctagatgtta tcataaggta ccatttatgc 60180
aagaacacgc agagaaaaga tacaagcact ttacaaaaaa tactcccgaa ttttatttat 60240
acccacattc tgggtaccgt gaagcagaca tatactataa ctactatgac gaggaaaaag 60300
tgggattata tgaaggaagt ggatattaaa tggaaccacc agatttagaa agcctaacct 60360
tgtgggtgat ttacgaccgt gttagtgaca cgttccacaa aggcgggaat caatacttct 60420
gctctagtcg ccagaagaaa gccattaaga cgtatggaac acttcaatct gctacagctt 60480
tgttaaaaca gatagaaggt ggagggattc acccagtaga tttagtgtta gtggaattag 60540
agtgtgagat tatggatttt atcgaagtag aataaactaa aaggagaatg attagatgaa 60600
aaaatcaatg atagctttag caattggggc agtattatta cttggaggat gtacttcttt 60660
tgatgattgg agtaaagatt gggaaagtga caccaaagga ttagaaagaa caatcactat 60720
ctacagcaag actggcgaag ttcttaaaca gtatgaagga gaaaacgttc gtactaaata 60780
ctcagatggc gggactcaag ttgttcttaa cattgatgga aagcgtgtcc aagtagttaa 60840
tgcagatgtt gttattacag aaaaaggtgc agagaaatac gaaaccaaat aatgtttgac 60900
aactaaataa atgcgtgtta taattagtta taccaattaa gaggagtgag cgattatggc 60960
aaaggctaga gatattctgg atgctacgaa gtggacagag attagagatt tccgaagata 61020
ttccataaac agggatggtg aggttgctaa taatattaca ggtcatttgc ttaaagtatc 61080
gtttgctcct cgtttgggtt atacggttaa actagtggat gacgtggcta acttgcagag 61140
agtggttaag ctggcggatt tactggctag aacgtttgtt cctagtgtat taggtgctac 61200
acaagtagta tttatagacg gcgataaaaa gaatttggat ttaaataatt tggaatacag 61260
attgtgaggt ttaatcatga agtattgtgt ttgcgtatgg gaagccactt ttaacttctc 61320
cataagttta ggactatttg ccacgaaaga acttgcagaa gaagctgtta aaagagattt 61380

```
agaagattat acagaaagag aattagataa ctaccaagtt tttgttagag gagtgtctgg  61440
attttatgtg taacttaaaa ccagctatac cagatatgta tgtttctgct gtaaaggatt  61500
tatatatgga taattatttt aatgagagtt ccacagccat cactaaaata attataggat  61560
attctgaata ctgtaaaagc acatgtatag gagtaacaag tggggactat aaacatgtaa  61620
agctgtttgg ggaagatggt attactctac acataggaga ggtggtttgg aactagttat  61680
gcactatctt tccaaacaga aaggggaata atcactacta tgtatatttt aatacagcta  61740
gtagattggc aaaaggatga tgaagttgtt gctggaaaag tattaaaagt aggaggttgc  61800
tcctttcaag gagttaagat attgttaagt aaacacatga aagatatggc tagtttgcat  61860
gacagagcct cctacaggta tgctactgca cttatggata gatgtatgaa tttagatagc  61920
atatcccgca cattaagaac acacacagag tggcgagtaa aatttaaagt agtttttaga  61980
gaggaatggt atgaataatg gaaaaattag atactatgga acaaattact aagttacaga  62040
agaaagcaat tgaggtggcg aaagagttat atggtgatat taaagaaaca gactttacgg  62100
taattcagcc atatgcagat ggacacggaa ttttgtttag tgttagtgat gacgaccaag  62160
gagaacgcac tatgagtgtt aacgttgtag acacgttgac agtgcttcct gctattgatg  62220
ggactttaga tgcttacgag gaagaaacag aatgatgata gtgtggataa tcttaattat  62280
tagtatcaca ttctttttaa cagcacgcaa actagaagac gatgtggcaa ttgtttggat  62340
acttgttata tatttagcaa tatcttttct tttagtaaat ttgacaaaca cgtaagtaag  62400
tggtatactt gtaatataga aggagggaaa cacatgtatg aatattgttg caaagaagta  62460
aatgaacgta agcgtgatac caacttaatg tatccagaca agggattatc ctatttagat  62520
gaggaggatt gtttggcaat tttcttagga gattttggag atgacatacc ccatacatta  62580
tatgtgctag ttaagcactg tccatggtgt ggaagaaatt tggaagagga tgttatgtgt  62640
gagtactgta atagagacca caatttaaga caaacaaaag aactacatgg atataacgag  62700
gtaaaaatag atggagacaa cgatttacag gtaacttatg aattaggtgg tgcagaggaa  62760
gaccttttgc tagaaataag ttattgccct tggtgtggta gtaagttgga aggtagtgaa  62820
ttaaaatggc taaattccaa gtaggtgatg aagtatatgc ttcctatgta gatgaaatag  62880
gaacagttat tagaatcgta tgggaattat cagaaggcaa ctcaggtttt aatgcttatg  62940
aagtacaatt taacgaccag tcaagagttg tagccgaact agctttacaa ccatcaacca  63000
agcaatagta cgtattaaat taaatggagg aatattgatg gaattttata atggtcaaaa  63060
gatagagttc atttcttgta ataaaaaaca agtaggggaa atagtagaag ttcatcctga  63120
aagcgggata ttgagcatta gagatagtga tggaatagag ctaggtgtaa gaatcaacaa  63180
tgtagttgaa tataaagaac cagaattacc tgtagttccg aagtgtgtgg cgggttggtt  63240
tgaaaagaat aagaataatt tagataatga aatttggcga tatattcgca actttgatga  63300
gcagaacaca gatagtaatt tttacatgtt catgaatgat gcgacaagta atcctattga  63360
gatattggtg gaaatgaaga atggatataa gattgaagct acacctgcta cgtatgtgtc  63420
tacgtgtgga gaagatacag aagtaaagta tgtaatttta agagataaag aaacaactaa  63480
ggtagatggt acgtattacg ttaggatggg cacacccgta gctaaatcat ttgaatatgc  63540
tcttacacca gataaggaat gtgctattat tggagataag gtaaacatga ccgcaattgc  63600
atgtttctta gcttcccaaa atactagcca cacgtttgac gttgtgccat atgaggaaga  63660
gatttaatga agcacaaggt aggagataaa gtagaactaa tttggtacga ggtaataaga  63720
```

gaagtaatta ttgtagagga acttccaaaa ggggaatatg tagtagaatt tgtgcacgat 63780
ggggaaagag agacaatcca tgaagcaggt atgatggaaa cgggaacgat tacaaagtta 63840
gcaagtgaag agctagttaa acttcccact tatatggaag attggttaga gtttggagat 63900
aggcagggat atgatttagt cgatttgttt aattactata atagtaacat gtccaaagag 63960
gtagaagagt ggatagtaaa tagtgaaacg aaccagtata aatttgctat ggcttggtta 64020
tgtggatatg ttgtggagga ggaattagca aatggataaa tcacgtataa ccgtattgct 64080
aaaatcgggt aatagatgtc agattactca tccagatgtg gtggaggaag tttgggaaga 64140
gttttcttta gaaaaggtaa aacaaggagt tactttacaa gatagacact ccaaaacaat 64200
tatcccgtat gagtctatcg attgtatcta tattgaagaa ttggaggcgg aagaatgaac 64260
gataaaaaga cagattataa agtatataaa ataacataca agcaacgttt tatgggggaa 64320
gttattgttg actcatatga aagaacggta aaagatgata acgaattacg gtctgcaatt 64380
aacgctttat atgacgaccc acatgtgttt tcagttagta gtgaagaggt ggcggaataa 64440
atgggagtga gtattgattt atacagttat gattatgaag cacttgtgga aggcattcaa 64500
agctatacaa aagcggaaaa tacggaagtt ataagaaaaa tacttctaat aggcggaaat 64560
gtcgtaggtg ataaatatat cattttaaac aatgaactct gggaagataa cagttcatat 64620
tacaacgttc cgaacgcttt agagcgtttg tataaagttg atgatgtctt tggaaaaatc 64680
ttctgtactt ttgatgatag gttcggtaga gagacgctaa ttaatggttg tgatacccca 64740
gaagaaatat tagaagaggt gatggaatga cgacatttaa accgagaaac atcctaagtt 64800
ggcgcagtgg attgccttac gataatacga gattttcaat aggtagacct ccagcaggcg 64860
gacaacatag tgatgaatgg tataacggag aaatgaatgt aaatgtaatc agcattgaat 64920
atatactgcc taatccaatc acggaaagca caggaaacta tattatcaag ttggaagatg 64980
ataggagaat tgttatctcc gaagaaattc cgtcttttat tgaggaggtg gcggaataaa 65040
cgtagtggat attaacgtat cagagttgat gaaggagtta cagaaaatcc cgccagatag 65100
ttcaattttt atagaggaat attgttacgt ttctgatacg gctagggtaa agtatagtga 65160
aaaatatggt gaggtacgtt tgtgtactaa tgaataggag gaaataacat ggctaaagaa 65220
ccaagagacg tgtggatagt ttattatgaa gtacttggcg gggtggaata ttacttagct 65280
agctccaaca tagacaagct tatttttaga ccaagtacac tagaaggaaa tgctttagaa 65340
ttccctacac aagattccgc agagggaatg gctaaggtgg ctaatgcgtt ggatactaac 65400
caagaccatt ggtggaagat taagaaagtg gataacactc aagtgtatgt gatgtttgca 65460
ccagttatta ctcacttgat acaggtggca gtaaataccg acacgccaag agatttagca 65520
gatttacagg tgtgtgaggc tttctttagt gagtttcacg aattagaacc tgttacccta 65580
gccaagagat ttacaagaga agaatttgaa gaacttaaaa caagatacac aggtattatg 65640
gctattccag tagatgacgt tatgaatact ttagaaagat tctataacac ttcctcttat 65700
aataaactta agaagggtaa agcagttatg gaagtgttcc gggagtataa agcaagtggg 65760
aactaatatg ttcgtagtgt ggttcgcaat tattagctac ttttttggaa gtattactac 65820
catatttact ggtgtgtgca aagtaagaag tggtgaagaa gtggttggtg gcgttataga 65880
catattggct ggtctcctat ttgctggaat gagttggtta tttatagtta tatttctata 65940
gataaggaag gagttgttta atttgttggt agtgctagga attgtgttct ttctttctat 66000
actgtcaatt gctggtttcg gactggttat ttatagttgg agaagtgaaa tagtcgtagc 66060
tctttttgga ttatttttag ggatgattac tttatttagt gtttttgtat tgttgtttaa 66120

-continued

```
tacttaagga ggtgaaaaac acaatgacag atatagtagt gcagatttta acttatatat  66180

tgatagtggg ctttagcttc ttcgggataa ctaaccttat tgagggtatt aaaaataaag  66240

ggaaaagacc cgcttattct aggttcctag atattactac tggtgtggga ttgttagcac  66300

tagtttggct ttggtttacc caaggtggag tatcttaatg aaaattcccg catagtttaa  66360

ccagagagtg ccagttaggt actctttttg gcgtgttgtg gaatagttgt ggctagtgtg  66420

gacgtgttgt ggcgtgttgt gacaaggtgg cggtttactt ggtacccccca gtcgtaaccc  66480

atacagtgaa aataggaaac gtgaaattgt aatagtctgc ggagaattat cagaattttt  66540

tgaacacccc tacgtctccg aattttccga ctcttctaac tactcagtct actcgctcgc  66600

tttcgctcgc tcctcgttag ctcgacacgt attgcacact tgctttattt atattacatg  66660

tattagcatg tgagtgcgtg tgtgcacgtg tactacagta actacacata gatatacatg  66720

ctacaggtac tatttaatat aagggctaat aaaacgctta cattcgatta gctaattata  66780

cttcctataa catacattat gttaacttgt tagatgagta taaaataata gataattata  66840

tttagataa                                                          66849
```

*LISTERIA* BACTERIOPHAGE P825 AND USES THEREOF

CROSS REFERENCE TO RELATED APPLICATIONS

This application is a §371 National Stage Application of PCT/EP2012/002270, filed May 29, 2012, which claims priority to European Application No. 11004348.6, filed May 26, 2011.

BACKGROUND OF THE INVENTION

Field of the Invention

The present invention relates to a novel *Listeria* bacteriophage designated ProCC P825. In particular, the present invention relates to the endolysin PlyP825 encoded by the novel phage ProCC P825 and uses of the novel endolysin PlyP825 for controlling *Listeria* contamination and infection.

Description of Related Art

The gram-positive bacterium *Listeria monocytogenes* is a bacterial pathogen which is known as the causative organism in several outbreaks of food-borne disease. Listeriosis is a life-threatening infection of humans worldwide which is caused by *Listeria monocytogenes* and which is characterized by a variety of symptoms and conditions, including diarrhea, abortion and encephalitis. In industrialized countries, high mortality is associated with listeriosis following *Listeria monocytogenes* food contamination. In humans, the prevalence of listeriosis has risen significantly since the 1980s, resulting in intensified surveillance of *Listeria monocytogenes* in food industry. This contributed to a decrease of human listeriosis cases in the last two decades (McLauchlin 1987, Oevermann et al. 2008). However, its prevalence has again increased in the last few years (Gillespie et al. 2006, Goulet et al. 2008, Gillespie et al. 2009).

The species *Listeria monocytogenes* encompasses numerous strains and the genetic diversity amongst them is high (Doumith et al. 2004). Various strains have been implicated in both human and animal disease, and current surveillance schemes for foods are based on the assumption that all *Listeria monocytogenes* isolates are potentially pathogenic, resulting in costly recalls in food industry (Oevermann et al. 2010).

While listeriosis is greatly aided by early administration of antibiotics with rapid bactericidal activity against *Listeria monocytogenes*, research to improve food safety is directed to exploring novel technologies such as the use of bacteriophage for specific killing of bacteria.

Bacteriophages are viruses that infect bacteria. They are obligate intracellular parasites and lack their own metabolism. Phages are the natural enemies of bacteria. They are host-specific in that they infect specific bacterial species or even specific strains (Hagens and Loessner 2007). There are a few exceptions like *Listeria* bacteriophage A511, which can infect and kill bacteria within an entire genus. The extreme specificity of phages renders them ideal candidates for applications designed to increase food safety. Phages can be used for biocontrol of bacteria without interfering with the natural microflora.

Endolysins from *Listeria* bacteriophages are promising tools for detection and control of *Listeria* contamination and infection. These proteins have a modular organization, which is characterized by an N-terminal localized enzymatically active domain (EAD), which contributes lytic activity, and a C-terminal localized cell wall binding domain (CBD), which targets the lysin to its substrate.

It is an object of the present invention to provide a novel *Listeria* bacteriophage and novel endolysins against *Listeria*, which exhibit improved properties over known *Listeria* bacteriophages and known endolysins against *Listeria*.

SUMMARY

The present invention provides a novel *Listeria* bacteriophage designated ProCC P825, which has been deposited at DSMZ, Braunschweig, Germany, under international deposit number DSM 23783 in accordance with the Budapest treaty for deposit of cell cultures. In the present invention, the novel bacteriophage "ProCC P825" is simply named "P825". Therefore, whenever reference is made herein to "P825", the novel bacteriophage "ProCC P825" as deposited at DSMZ, Braunschweig, Germany, under deposit number DSM 23783 is meant.

The present invention provides the novel *Listeria* bacteriophage designated ProCC P825 and a novel endolysin designated PlyP825, which is encoded by the novel *Listeria* bacteriophage P825. The novel endolysin designated PlyP825 is encoded by the nucleic acid sequence shown in SEQ ID NO: 1, which comprises 945 nucleotides. The corresponding amino acid sequence of PlyP825 is set forth in SEQ ID NO: 2 and comprises 315 amino acid residues accordingly. The novel endolysin PlyP825 is particularly useful in the control of *Listeria* contamination and infection.

Aspects of the invention are:

1. A bacteriophage capable of lysing *Listeria* serovars 1/2, 3, 4, 5, and 6.

2. The bacteriophage of item 1, wherein the bacteriophage has a genome (i) comprising the DNA sequence of SEQ ID NO: 7; (ii) having at least 90% or 95% sequence identity with the DNA sequence of SEQ ID NO: 7; or (iii) having at least 90% or 95% sequence identity with the DNA sequence of the genome of bacteriophage ProCC P825 deposited under accession No. DSM 23783.

3. A nucleic acid molecule comprising a polynucleotide selected from the group consisting of:

(a) a polynucleotide encoding a polypeptide having the amino acid sequence of SEQ ID NO: 2;

(b) a polynucleotide encoding a fragment, analog or functional derivative of a polypeptide encoded by the polynucleotide of (a), wherein said fragment, analog or functional derivative has endolysin activity;

(c) a polynucleotide which is at least 75% identical to the polynucleotide of (a), and which encodes a polypeptide having endolysin activity;

(d) a polynucleotide encoding a polypeptide having an amino acid sequence that is at least 75% identical to the amino acid sequence of SEQ ID NO: 2 and having endolysin activity;

(e) a polynucleotide which hybridizes under stringent conditions to the polynucleotide of any one of (a) to (d);

(f) a polynucleotide comprising the nucleotide sequence of SEQ ID NO: 1;

(g) a polynucleotide which is at least 75% identical to the nucleotide sequence of SEQ ID NO: 1 and which encodes a polypeptide having endolysin activity;

(h) a polynucleotide comprising part of the nucleotide sequence of (f) and which encodes a fragment, analog or functional derivative of the polypeptide having the amino acid sequence of SEQ ID NO: 2, wherein said fragment, analog or functional derivative has endolysin activity; and (i) a polynucleotide that is the complement of the full length of a polynucleotide of any of (a) to (h).

4. A vector comprising the nucleic acid molecule of item 3.

5. A host cell transformed or transfected with the nucleic acid molecule of item 3, or the vector of item 4.

6. The host cell of item 5, containing a polypeptide expressed from the nucleic acid molecule of item 3, or from the vector of item 4.

7. A method of making a polypeptide encoded by the nucleic acid molecule of item 3, comprising culturing the host cell of item 5 under conditions such that the polypeptide encoded by the nucleic acid molecule of item 3 is expressed, and recovering the polypeptide encoded by said nucleic acid molecule.

8. A polypeptide encoded by the nucleic acid molecule of item 3, or obtainable by the method of item 7.

9. An endolysin protein obtainable from (i) the bacteriophage of item 1 or 2, or (ii) bacteriophage ProCC P825 deposited under accession No. DSM 23783, or a fragment, analog or functional derivative thereof having endolysin activity.

10. A chimeric lysin protein comprising:

(i) the polypeptide of item 8 or the endolysin protein of item 9 and a heterologous protein, wherein the chimeric lysin protein has lysin activity; or (ii) the polypeptide of item 8 or the endolysin protein of item 9, wherein the enzymatically active domain (EAD) of the polypeptide of item 8 or the endolysin protein of item 9 is substituted with an EAD of a heterologous lysin protein, wherein the chimeric lysin has lysin activity.

11. A composition, preferably a pharmaceutical composition or a disinfecting composition, comprising (i) the bacteriophage of item 1 or 2, (ii) the nucleic acid molecule of item 3, (iii) the vector of item 4, (iv) the host cell of item 5 or 6, (v) the polypeptide of item 8, (vi) the endolysin protein of item 9, or (vii) the chimeric lysin of item 10.

12. A solution, preferably a disinfecting solution, comprising (i) the bacteriophage of item 1 or 2, (ii) the nucleic acid molecule of item 3, (iii) the vector of item 4, (iv) the host cell of item 5 or 6, (v) the polypeptide of item 8, (vi) the endolysin protein of item 9, or (vii) the chimeric lysin of item 10.

13. A method for controlling *Listeria* contamination, preferably for sanitizing and/or disinfecting *Listeria* contamination, comprising applying the composition according to item 11 or the solution of item 12 to the site of *Listeria* contamination, with the proviso that the method is not a therapeutic method.

14. Use of (i) the bacteriophage of item 1 or 2, (ii) the nucleic acid molecule of item 3, (iii) the vector of item 4, (iv) the host cell of item 5 or 6, (v) the polypeptide of item 8, (vi) the endolysin protein of item 9, or (vii) the chimeric lysin of item 10 in a method for controlling *Listeria* contamination, preferably for sanitizing and/or disinfecting *Listeria* contamination, with the proviso that the method is not a therapeutic method.

15. The bacteriophage of item 1 or 2, the nucleic acid molecule of item 3, the vector of item 4, the host cell of item 5 or 6, the polypeptide of item 8, the endolysin protein of item 9, or the chimeric lysin of item 10 for use in the treatment and/or prevention of a *Listeria* infection.

16. A kit comprising (i) the bacteriophage of item 1 or 2, (ii) the nucleic acid molecule of item 3, (iii) the vector of item 4, (iv) the host cell of item 5 or 6, (v) the polypeptide of item 8, (vi) the endolysin protein of item 9, or (vii) the chimeric lysin of item 10.

17. An antibody or fragment thereof that binds specifically to the polypeptide of item 8, the endolysin protein of item 9, or the chimeric lysin protein of item 10.

18. A nucleic acid molecule comprising the DNA sequence of the genome of the bacteriophage of item 1 or 2.

19. A product comprising (i) the bacteriophage of item 1 or 2, (ii) the polypeptide of item 8, (iii) the endolysin protein of item 9, or (iv) the chimeric lysin of item 10.

20. The product of item 19, which is a food product, preferably a dairy product.

21. A bacteriophage having lytic activity against *Listeria* serovar 3 obtainable by (a) plating a sample containing bacteriophage and *Listeria* bacteria serovar 3 to obtain plaques, and (b) purifying the phage contained within the one or more plaques.

22. A bacteriophage, which has lytic activity against *Listeria* serovar 3.

BRIEF DESCRIPTION OF THE DRAWINGS

FIG. 8 shows a comparison of the MIC of endolysins Ply511, PlyP40, and PlyP825 against *Listeria monocytogenes* ProCC S1095 sv 1/2a, *Listeria monocytogenes* ProCC S1135 sv 3a, *Listeria monocytogenes* ProCC S776 sv 4b, and *Listeria innocua* ProCC S1147 sv 6a.

DETAILED DESCRIPTION OF A PREFERRED EMBODIMENT

Figure 1:
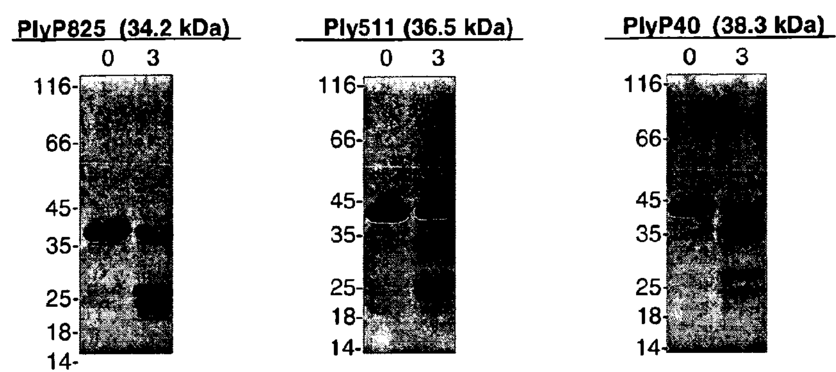
FIG. 1 shows trypsin digestion of endolysins PlyP825, Ply511 and PlyP40. Aliquots were analyzed at 0 and 3 min. The marker is shown in kDa. Analysis was performed on a 4-12% SDS-Gel (NuPage Novex, Invitrogen).

Bacteriophage-encoded endolysins are highly active enzymes, which hydrolyze bacterial cell walls. These phage-encoded cell wall lytic enzymes are synthesized late during virus replication and mediate the release of progeny virions. Endolysins can be used to lyse *Listeria* cells in various applications including *Listeria* contamination and infection. Endolysins can also be used to lyse *Listeria* cells simply to recover nucleic acids or cellular protein for detection or differentiation.

The novel *Listeria*-specific bacteriophage ProCC P825 ("P825") provided by the present invention has been deposited internationally on Jul. 14, 2010 at the DSMZ—

Deutsche Sammlung von Mikroorganismen and Zellkulturen GmbH, Braunschweig, Germany, under international deposit accession No. DSM No. 23783 in accordance with the Budapest treaty concerning deposit of cell cultures. The address of DSMZ is Inhoffenstr. 7B, 38124 Braunschweig, Germany.

The name and address of the depositor of the novel bacteriophage P825 is as follows: Hyglos Invest GmbH, Am Neuland 1, 82347 Bernried, Germany. Evidence is provided by a separate document enclosed with this application that the depositor Hyglos Invest GmbH, Bernried, Germany, has authorized the applicant to refer to the deposited biological material in the present application, and has given his unreserved and irrevocable consent to the deposited material being made available to the public (in accordance with, for example, Rule 33 EPC). In addition, said separate document provides evidence that the depositor Hyglos Invest GmbH, Bernried, Germany, has given his consent that the applicant makes use of the so-called "expert solution" (in accordance with, for example, Rule 32 EPC).

The novel *Listeria*-specific bacteriophages provided by the present invention are capable of lysing *Listeria* serovars 1/2, 3, 4, 5 and 6. Thus, bacteriophages according to the present invention are broad host range bacteriophages. Importantly, these novel phages are capable of lysing *Listeria* serovar 3, which is one of the clinically relevant *Listeria* serovars. Therefore, bacteriophages of the present invention are in particular those which are capable of lysing *Listeria* serovar 3. This activity is unique to the novel bacteriophages provided by the present invention. *Listeria*-specific bacteriophages described in the art do not exhibit this specific property. The novel bacteriophages provided by the present invention are strictly lytic and therefore invariably lethal to a *Listeria* bacterial cell after infection. The lytic activity comes from the endolysin encoded by the novel phages capable of lysing *Listeria* serovars 1/2, 3, 4, 5 and 6. Therefore, the endolysin encoded by the novel bacteriophages of the present invention can be used for controlling *Listeria* contamination and infection. The endolysins encoded by the novel bacteriophages comprise an EAD (enzymatically active domain), which contributes for the lytic activity of the endolysin, and a CBD (cell wall binding domain), which targets the lysin to its substrate.

In various embodiments, a novel *Listeria*-specific bacteriophage provided by the present invention is a non-modified bacteriophage capable of lysing *Listeria* serovars 1/2, 3, 4, 5 and 6, in particular a non-modified bacteriophage capable of lysing *Listeria* serovar 3. As used herein, a non-modified bacteriophage is a wild-type bacteriophage.

The novel *Listeria* bacteriophage P825 is capable of lysing *Listeria* serovars 1/2, 3, 4, 5 and 6. Importantly, phage P825 is capable of lysing *Listeria* serovar 3, which is one of the clinically relevant *Listeria* serovars. This activity is unique to the novel bacteriophage P825. Bacteriophages described in the art do not exhibit this specific property. The novel *Listeria* bacteriophage P825 is strictly lytic and therefore invariably lethal to a *Listeria* bacterial cell after infection. The lytic activity comes from the endolysin PlyP825 encoded by the phage P825. Therefore, PlyP825 can be used for controlling *Listeria* contamination and infection. PlyP825 comprises an EAD (enzymatically active domain), which contributes for the lytic activity of the endolysin, and a CBD (cell wall binding domain), which targets the lysin to its substrate. The nucleotide and amino acid sequence of the PlyP825 EAD are shown in SEQ ID NOs: 3 and 4, respectively. The nucleic acid sequence encoding the PlyP825 EAD comprises nucleotides 1 to 426 of SEQ ID NO: 1. The amino acid sequence of the PlyP825 EAD comprises amino acid residues 1 (M1) to 142 (E142) of SEQ ID NO: 2. In the present invention, the EAD of SEQ ID NO: 4 may also be called "the lytic domain" of the PlyP825 endolysin of SEQ ID NO: 2.

The nucleotide and amino acid sequence of the PlyP825 CBD are shown in SEQ ID NOs: 5 and 6, respectively. The nucleic acid sequence encoding the PlyP825 CBD comprises nucleotides 487 to 945 of SEQ ID NO: 1. The amino acid sequence of the PlyP825 CBD comprises amino acid residues 163 (G163) to 315 (N315) of SEQ ID NO: 2. In the present invention, the CBD of SEQ ID NO: 4 may also be called "the cell wall binding domain" of the PlyP825 endolysin of SEQ ID NO: 2.

The nucleotide sequence of the genome of phage P825 is depicted in SEQ ID NO: 7, and contains 66,849 nucleotides, including the stop codon.

Lytic Activity of Phages of the Present Invention

The phages provided by the present invention exhibit lytic activity against *Listeria* bacteria. As demonstrated by the inventors, phage P825 completely inhibited growth of *Listeria monocytogenes* strains. Phage P825 not only inhibited growth but actually reduced *Listeria* titers. As confirmed by enrichment studies, applying phage P825 completely eradicated *Listeria* bacteria. The lysis spectrum of phage P825 has been shown to be consistent with the host specificity provided by the tail spike protein of phage P825 responsible for receptor binding on the *Listeria* cell surface.

The present invention provides bacteriophages capable of lysing *Listeria* serovars 1/2, 3, 4, 5, and 6. A preferred phage is phage P825. The present invention also provides phages that are capable of lysing *Listeria* serovars 1/2, 3, 4, 5, 6 and 7. A preferred phage is phage P825. In various embodiments, a phage according to the present invention is capable of specifically lysing *Listeria* serovar 3. A preferred phage is phage P825.

As described above, the phages provided by the present invention exhibit lytic activity against *Listeria* bacteria, i.e., they have the activity of lysing *Listeria* bacteria, in particular *Listeria* serovars 1/2, 3, 4, 5, 6 and 7, in particular *Listeria* serovar 3. In the context of the present invention, the terms "exhibiting lytic activity against *Listeria* bacteria", "having lytic activity against *Listeria* bacteria", "having the activity of lysing *Listeria* bacteria" and "being capable of lysing *Listeria* bacteria" may be used interchangeably. The present invention provides a bacteriophage capable of lysing *Listeria* bacteria, preferably *Listeria monocytogenes*, wherein the bacteriophage has a genome (i) comprising the DNA sequence of SEQ ID NO: 7; (ii) having at least 90% or 95% sequence identity with the DNA sequence of SEQ ID NO: 7; or (iii) having at least 90% or 95% sequence identity with the DNA sequence of the genome of bacteriophage ProCC P825 deposited under accession No. DSM 23783. In various embodiments, the phage provided by the present invention is capable of lysing any one of the *Listeria* species described herein. In various embodiments, the phage according to the present invention has a genome having at least 96%, 97%, 98%, or 99% sequence identity with the DNA sequence of the genome of bacteriophage ProCC P825 deposited under accession No. DSM 23783. In various embodiments, the phage according to the present invention has a genome having at least 96%, 97%, 98%, or 99% sequence identity with the DNA sequence of SEQ ID NO: 7. Preferably, the phage according to the present invention is bacteriophage ProCC P825 deposited under accession No. DSM 23783.

The present invention provides a nucleic acid molecule comprising the DNA sequence of the genome of a bacteriophage according to the present invention. In various embodiments, the nucleic acid molecule comprises the DNA sequence of SEQ ID NO: 7. In various embodiments, the nucleic acid molecule has at least 90%, 95%, 96%, 97%, 98%, or 99% sequence identity with the DNA sequence of SEQ ID NO: 7. In various embodiments, the nucleic acid molecule has at least 90%, 95%, 96%, 97%, 98%, or 99% sequence identity with the DNA sequence of the genome of bacteriophage ProCC P825 deposited under accession No. DSM 23783. The present invention provides any polypeptide encoded by the nucleic acid molecule of SEQ ID NO: 7 or variants thereof as described herein above.

Lytic Activity of Proteins of the Invention

A major problem of phage endolysins is the proteolytic instability. Until now, two *Listeria* endolysins are known that are not restricted to lyse distinct *Listeria* serovars like Ply500 and Ply118 (Loessner et al., 2002), but are able to lyse several *Listeria* serovars: Ply511 of *Listeria* phage A511 and PlyP40 of *Listeria* phage P40. However, a bacteriophage according to the present invention is capable of lysing all of serovars 1/2, 3, 4, 5, and 6. This property is unique to bacteriophages of the present invention. Thus, bacteriophages according to the present invention are broad host range bacteriophages. Importantly, bacteriophages of the present invention are capable of lysing *Listeria* serovar 3, which is one of the clinically relevant serovars. This activity is not shared by any known *Listeria*-specific bacteriophages.

In order to compare the proteolytic sensitivity of the three endolysins of phages A511, P40, and P825, they were Trypsin-digested in equimolar amounts. Aliquots were retained and analyzed after 0 and 3 min incubation at room temperature (FIG. 1). As shown in FIG. 1, PlyP825 shows less proteolytic degradation sites than Ply511 and PlyP40.

PlyP825 was analyzed for its activity against different *Listeria* strains with serovars 1/2, 3, 4, 5 and 6. Exponential *Listeria* cells were poured in LB-Top Agar in plates. Onto the solidified agar 2 μg of PlyP825 was spotted. After incubation over night at 30° C. all 22 strains tested were lysed by the endolysin PlyP825 (Table 2). Thus, PlyP825 is a broad range *Listeria* endolysin.

Figure 2:
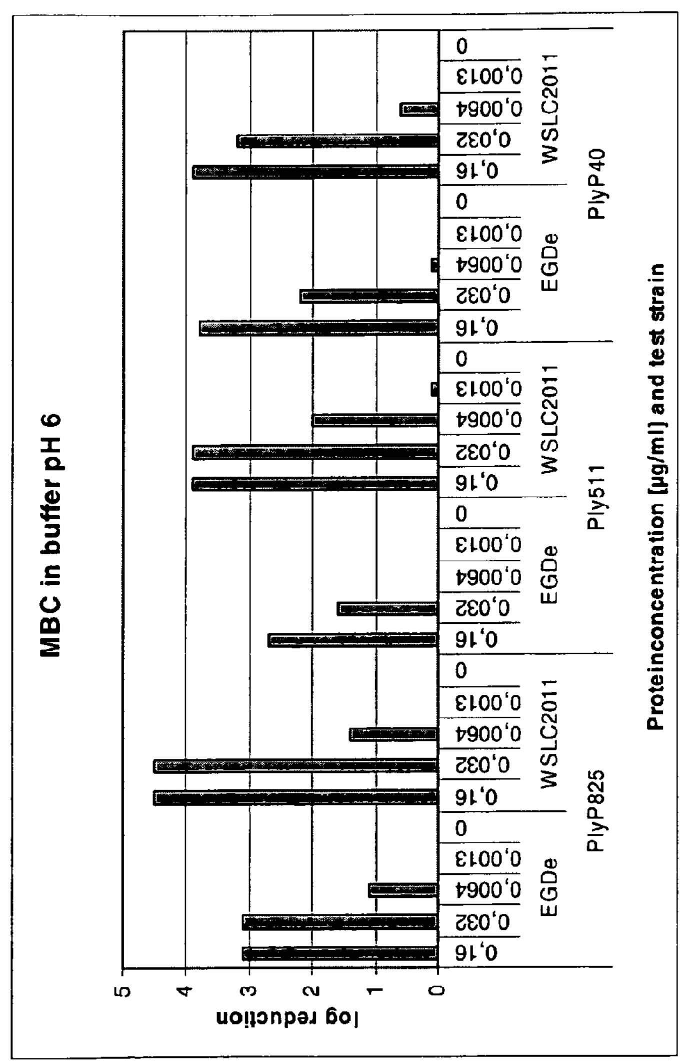
FIG. 2 shows MBC (minimum bactericidal concentration) testing of endolysins PlyP825, Ply511 and PlyP40 in buffer pH 6 against *Listeria monocytogenes* EGDe sv 1/2a and *Listeria innocua* WSLC2011 sv 6a. Buffer: 20 mM sodium phosphate, 50 mM sodium chloride, 0.05% Tween pH 6.

The minimum bactericidal concentrations (MBC) of endolysins PlyP825, Ply511 and PlyP40 in buffer and in milk were determined and compared. For determining the MBC in buffer pH 6 the endolysin enzymes were incubated with $10^5$ cells/ml of strains *Listeria monocytogenes* EGDe sv 1/2a and *Listeria* innocua WSLC2011 sv 6a in buffer (20 mM Sodium-phosphate, 50 mM sodium chloride, 0.05% Tween 20 pH 6) at 30° C. After 1 h the samples were plated and cell numbers counted. FIG. 2 shows the results: PlyP825 reduces effectively pathogenic and non-pathogenic *Listeria* cells in buffer: 0.032 μg/ml endolysin were sufficient to reduce 4.5 (WSLC2011) or 3.1 (EGDe) orders of magnitude of *Listeria* cells. This is about 0.5 to 1.5 log more than Ply511 and 0.9-1.3 log more than PlyP40 were able to reduce with the same protein concentration.

Figure 3:
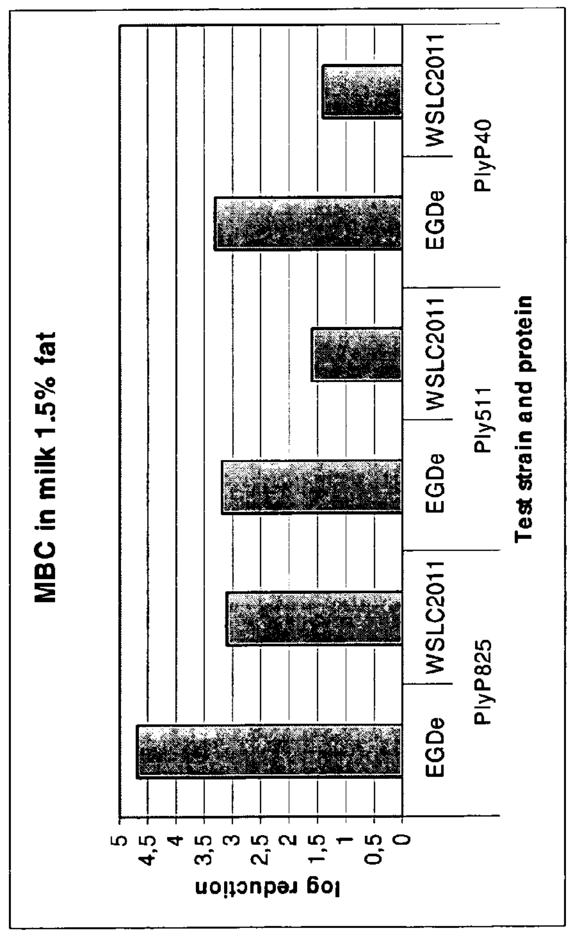
FIG. 3 shows MBC testing of endolysins PlyP825, Ply511 and PlyP40 in milk 1.5% fat against *Listeria monocytogenes* EGDe sv 1/2a and *Listeria* innocua WSLC2011 sv 6a. Testing was performed with 20 μg/ml endolysin.

For determining the MBC in milk the enzymes were incubated with $10^5$ cells/ml of strains *Listeria monocytogenes* EGDe sv 1/2a and *Listeria* innocua WSLC2011 sv 6a in milk with 1.5% fat at 30° C. After 3 h the samples were plated and cell numbers counted. FIG. 3 shows the results: PlyP825 shows the highest *Listeria* cell reduction in milk. Independent from the test strain PlyP825 reduces 1.4-1.7 orders of magnitude more cells than the other two broad *Listeria* endolysins Ply511 and PlyP40 in milk with 1.5% fat.

Figure 4:
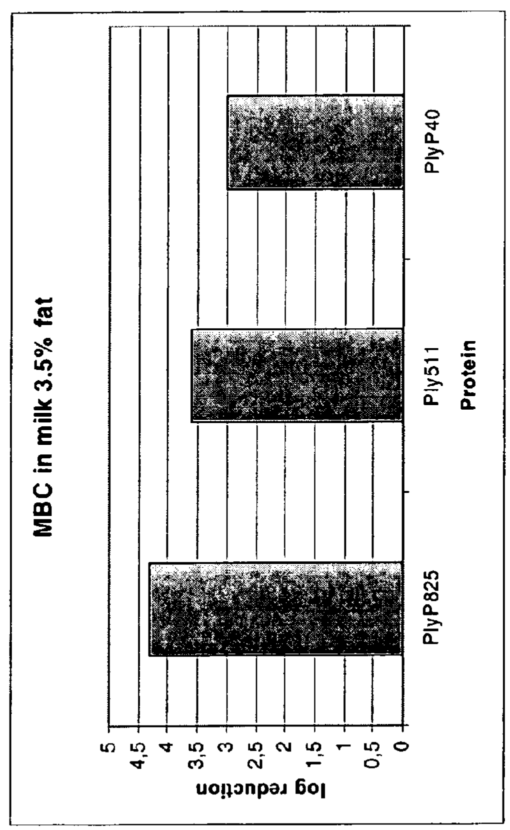
FIG. 4 shows MBC testing of endolysins PlyP825, Ply511 and PlyP40 in milk 3.5% fat against *Listeria monocytogenes* EGDe sv 1/2a. Testing was performed with 20 μg/ml endolysin.

Besides the enzymes were incubated with $10^5$ cells/ml of strains *Listeria monocytogenes* EGDe sv 1/2a in milk with 3.5% fat at 30° C. After 3 h the samples were plated and cell numbers counted. FIG. 4 shows the results: Also in milk with 3.5% fat PlyP825 reduces the highest cell number.

PlyP825 Nucleic Acid and Amino Acid Sequences and Variants Thereof

The present invention provides a nucleic acid molecule comprising a polynucleotide encoding a polypeptide having the amino acid sequence of SEQ ID NO: 2. The present invention also provides a nucleic acid molecule, which comprises a polynucleotide that is at least 75% or at least 80% identical to a polynucleotide encoding a polypeptide having the amino acid sequence of SEQ ID NO: 2, and that encodes a polypeptide having endolysin activity, preferably the activity of the endolysin of SEQ ID NO: 2. The present invention further provides a nucleic acid molecule, which comprises a polynucleotide that is at least 85% or at least 90% identical to a polynucleotide encoding a polypeptide having the amino acid sequence of SEQ ID NO: 2, and that encodes a polypeptide having endolysin activity, preferably the activity of the endolysin of SEQ ID NO: 2. In various embodiments, the said nucleic acid molecule comprises a polynucleotide that is at least 91% or at least 92% identical to a polynucleotide encoding a polypeptide having the amino acid sequence of SEQ ID NO: 2, and that encodes a polypeptide having endolysin activity, preferably the activity of the endolysin of SEQ ID NO: 2. Preferably, the said nucleic acid molecule comprises a polynucleotide that is at least 93% or at least 94% identical to a polynucleotide encoding a polypeptide having the amino acid sequence of SEQ ID NO: 2, and that encodes a polypeptide having endolysin activity, preferably the activity of the endolysin of SEQ ID NO: 2. More preferably, the said nucleic acid molecule comprises a polynucleotide that is at least 95% or at least 96% identical to a polynucleotide encoding a polypeptide having the amino acid sequence of SEQ ID NO: 2, and that encodes a polypeptide having endolysin activity, preferably the activity of the endolysin of SEQ ID NO: 2. Still more preferably, the said nucleic acid molecule comprises a polynucleotide that is at least 97%, at least 98%, or even at least 99% identical to a polynucleotide encoding a polypeptide having the amino acid sequence of SEQ ID NO: 2, and that encodes a polypeptide having endolysin activity, preferably the activity of the endolysin of SEQ ID NO: 2.

Furthermore, the present invention provides a nucleic acid molecule comprising a polynucleotide, which encodes a polypeptide having an amino acid sequence that is at least 75% or at least 80% identical to the amino acid sequence of SEQ ID NO: 2, and which has endolysin activity, preferably the activity of the endolysin of SEQ ID NO: 2. The present invention also provides a nucleic acid molecule comprising a polynucleotide, which encodes a polypeptide having an amino acid sequence that is at least 85% or at least 90% identical to the amino acid sequence of SEQ ID NO: 2, and which has endolysin activity, preferably the activity of the endolysin of SEQ ID NO: 2. In various embodiments, the said nucleic acid molecule comprises a polynucleotide, which encodes a polypeptide having an amino acid sequence that is at least 91% or at least 92% identical to the amino acid sequence of SEQ ID NO: 2, and which has endolysin activity, preferably the activity of the endolysin of SEQ ID NO: 2. Preferably, the said nucleic acid molecule comprises a polynucleotide, which encodes a polypeptide having an amino acid sequence that is at least 93% or at least 94% identical to the amino acid sequence of SEQ ID NO: 2, and which has endolysin activity, preferably the activity of the endolysin of SEQ ID NO: 2. More preferably, the said nucleic acid molecule comprises a polynucleotide, which encodes a polypeptide having an amino acid sequence that is at least 95% or at least 96% identical to the amino acid sequence of SEQ ID NO: 2, and which has endolysin activity, preferably the activity of the endolysin of SEQ ID NO: 2. Still more preferably, the said nucleic acid molecule comprises a polynucleotide, which encodes a polypeptide having an amino acid sequence that is at least 97%, at least 98%, or even 99% identical to the amino acid sequence of SEQ ID NO: 2, and which has endolysin activity, preferably the activity of the endolysin of SEQ ID NO: 2.

Furthermore, the present invention provides a nucleic acid molecule comprising a polynucleotide, which encodes a fragment, analog or functional derivative of a polypeptide encoded by a polynucleotide encoding a polypeptide having the amino acid sequence of SEQ ID NO: 2, wherein said fragment, analog or functional derivative has endolysin activity, preferably the activity of the endolysin of SEQ ID NO: 2. Preferably, the said nucleic acid molecule comprises a polynucleotide, which encodes a fragment, analog or functional derivative of a polypeptide encoded by the polynucleotide of SEQ ID NO: 1, wherein said fragment, analog or functional derivative has endolysin activity, preferably the activity of the endolysin of SEQ ID NO: 2.

The present invention provides a nucleic acid molecule comprising a polynucleotide, which hybridizes under stringent conditions to any one of the polynucleotides described in the three preceding paragraphs. The present invention also provides a nucleic acid molecule comprising a polynucleotide that is the complement of the full-length of any one of the polynucleotides described in the three preceding paragraphs.

The present invention provides a nucleic acid molecule comprising a polynucleotide having the nucleotide sequence of SEQ ID NO: 1. The present invention also provides a nucleic acid molecule, which comprises a polynucleotide that is at least 75% or at least 80% identical to the nucleotide sequence of SEQ ID NO: 1, and that encodes a polypeptide having endolysin activity, preferably the activity of the endolysin of SEQ ID NO: 2. The present invention further provides a nucleic acid molecule, which comprises a polynucleotide that is at least 85% or at least 90% identical to the nucleotide sequence of SEQ ID NO: 1, and that encodes a polypeptide having endolysin activity, preferably the activity of the endolysin of SEQ ID NO: 2. In various embodiments, the said nucleic acid molecule comprises a polynucleotide that is at least 91% or at least 92% identical to the nucleotide sequence of SEQ ID NO: 1, and that encodes a polypeptide having endolysin activity, preferably the activity of the endolysin of SEQ ID NO: 2. Preferably, the said nucleic acid molecule comprises a polynucleotide that is at least 93% or at least 94% identical to the nucleotide sequence of SEQ ID NO: 1, and that encodes a polypeptide having endolysin activity, preferably the activity of the endolysin of SEQ ID NO: 2. More preferably, the said nucleic acid molecule comprises a polynucleotide that is at least 95% or at least 96% identical to the nucleotide sequence of SEQ ID NO: 1, and that encodes a polypeptide having endolysin activity, preferably the activity of the endolysin of SEQ ID NO: 2. Still more preferably, the said nucleic acid molecule comprises a polynucleotide that is at least 97%, at least 98%, or even at least 99% identical to the nucleotide sequence of SEQ ID NO: 1, and that encodes a polypeptide having endolysin activity, preferably the activity of the endolysin of SEQ ID NO: 2.

Furthermore, the present invention provides a nucleic acid molecule comprising a polynucleotide that is a part of the nucleotide sequence of SEQ ID NO: 1, and that encodes a fragment, analog or functional derivative of the polypeptide having the amino acid sequence of SEQ ID NO: 2, wherein said fragment, analog or functional derivative has endolysin activity, preferably the activity of the endolysin of SEQ ID NO: 2.

The present invention provides a nucleic acid molecule comprising a polynucleotide, which hybridizes under stringent conditions to any one of the polynucleotides described in the two preceding paragraphs. Preferably, the present invention provides a nucleic acid molecule comprising a polynucleotide, which hybridizes under stringent conditions to the polynucleotide of SEQ ID NO: 1. The present invention also provides a nucleic acid molecule comprising a polynucleotide that is the complement of the full-length of any one of the polynucleotides described in the two preceding paragraphs. Preferably the present invention provides a nucleic acid molecule comprising a polynucleotide that is the complement of the full-length of the polynucleotide of SEQ ID NO: 1.

PlyP825 EAD Nucleic Acid and Amino Acid Sequences and Variants Thereof

The present invention provides a nucleic acid molecule comprising a polynucleotide encoding a polypeptide having the amino acid sequence of SEQ ID NO: 4. The present invention also provides a nucleic acid molecule, which comprises a polynucleotide that is at least 75% or at least 80% identical to a polynucleotide encoding a polypeptide having the amino acid sequence of SEQ ID NO: 4, and that encodes a polypeptide having the lytic activity of the EAD of SEQ ID NO: 4. The present invention further provides a nucleic acid molecule, which comprises a polynucleotide that is at least 85% or at least 90% identical to a polynucleotide encoding a polypeptide having the amino acid sequence of SEQ ID NO: 4, and that encodes a polypeptide having the lytic activity of the EAD of SEQ ID NO: 4. In various embodiments, the said nucleic acid molecule comprises a polynucleotide that is at least 91% or at least 92% identical to a polynucleotide encoding a polypeptide having the amino acid sequence of SEQ ID NO: 4, and that encodes a polypeptide having the lytic activity of the EAD of SEQ ID NO: 4. Preferably, the said nucleic acid molecule comprises a polynucleotide that is at least 93% or at least 94% identical to a polynucleotide encoding a polypeptide having the amino acid sequence of SEQ ID NO: 4, and that encodes a polypeptide having the lytic activity of the EAD of SEQ ID NO: 4. More preferably, the said nucleic acid molecule comprises a polynucleotide that is at least 95% or at least 96% identical to a polynucleotide encoding a polypeptide having the amino acid sequence of SEQ ID NO: 4, and that encodes a polypeptide having the lytic activity of the EAD of SEQ ID NO: 4. Still more preferably, the said nucleic acid molecule comprises a polynucleotide that is at least 97%, at least 98%, or even at least 99% identical to a polynucleotide encoding a polypeptide having the amino acid sequence of SEQ ID NO: 4, and that encodes a polypeptide having the lytic activity of the EAD of SEQ ID NO: 4.

Furthermore, the present invention provides a nucleic acid molecule comprising a polynucleotide, which encodes a polypeptide having an amino acid sequence that is at least 75% or at least 80% identical to the amino acid sequence of SEQ ID NO: 4, and which has the lytic activity of the EAD of SEQ ID NO: 4. The present invention also provides a nucleic acid molecule comprising a polynucleotide, which encodes a polypeptide having an amino acid sequence that is at least 85% or at least 90% identical to the amino acid sequence of SEQ ID NO: 4, and which has the lytic activity of the EAD of SEQ ID NO: 4. In various embodiments, the said nucleic acid molecule comprises a polynucleotide, which encodes a polypeptide having an amino acid sequence that is at least 91% or at least 92% identical to the amino acid sequence of SEQ ID NO: 4, and which has the lytic activity of the EAD of SEQ ID NO: 4. Preferably, the said nucleic acid molecule comprises a polynucleotide, which encodes a polypeptide having an amino acid sequence that is at least 93% or at least 94% identical to the amino acid sequence of SEQ ID NO: 4, and which has the lytic activity of the EAD of SEQ ID NO: 4. More preferably, the said nucleic acid molecule comprises a polynucleotide, which encodes a polypeptide having an amino acid sequence that is at least 95% or at least 96% identical to the amino acid sequence of SEQ ID NO: 4, and which has the lytic activity of the EAD of SEQ ID NO: 4. Still more preferably, the said nucleic acid molecule comprises a polynucleotide, which encodes a polypeptide having an amino acid sequence that is at least 97%, at least 98%, or even 99% identical to the amino acid sequence of SEQ ID NO: 4, and which has the lytic activity of the EAD of SEQ ID NO: 4.

Furthermore, the present invention provides a nucleic acid molecule comprising a polynucleotide, which encodes a fragment, analog or functional derivative of a polypeptide encoded by a polynucleotide encoding a polypeptide having the amino acid sequence of SEQ ID NO: 4, wherein said fragment, analog or functional derivative has the lytic activity of the EAD of SEQ ID NO: 4. Preferably, the said nucleic acid molecule comprises a polynucleotide, which encodes a fragment, analog or functional derivative of a polypeptide encoded by the polynucleotide of SEQ ID NO: 3, wherein said fragment, analog or functional derivative has the lytic activity of the EAD of SEQ ID NO: 4.

The present invention provides a nucleic acid molecule comprising a polynucleotide, which hybridizes under stringent conditions to any one of the polynucleotides described in the three preceding paragraphs. The present invention also provides a nucleic acid molecule comprising a polynucleotide that is the complement of the full-length of any one of the polynucleotides described in the three preceding paragraphs.

The present invention provides a nucleic acid molecule comprising a polynucleotide having the nucleotide sequence of SEQ ID NO: 3. The present invention also provides a nucleic acid molecule, which comprises a polynucleotide that is at least 75% or at least 80% identical to the nucleotide sequence of SEQ ID NO: 3, and that encodes a polypeptide having the lytic activity of the EAD of SEQ ID NO: 4. The present invention further provides a nucleic acid molecule, which comprises a polynucleotide that is at least 85% or at least 90% identical to the nucleotide sequence of SEQ ID NO: 3, and that encodes a polypeptide having the lytic activity of the EAD of SEQ ID NO: 4. In various embodiments, the said nucleic acid molecule comprises a polynucleotide that is at least 91% or at least 92% identical to the nucleotide sequence of SEQ ID NO: 3, and that encodes a polypeptide having the lytic activity of the EAD of SEQ ID NO: 4. Preferably, the said nucleic acid molecule comprises a polynucleotide that is at least 93% or at least 94% identical to the nucleotide sequence of SEQ ID NO: 3, and that encodes a polypeptide having the lytic activity of the EAD of SEQ ID NO: 4. More preferably, the said nucleic acid molecule comprises a polynucleotide that is at least 95% or at least 96% identical to the nucleotide sequence of SEQ ID NO: 3, and that encodes a polypeptide having the lytic activity of the EAD of SEQ ID NO: 4. Still more preferably, the said nucleic acid molecule comprises a polynucleotide that is at least 97%, at least 98%, or even at least 99% identical to the nucleotide sequence of SEQ ID NO: 3, and that encodes a polypeptide having the lytic activity of the EAD of SEQ ID NO: 4.

Furthermore, the present invention provides a nucleic acid molecule comprising a polynucleotide that is a part of the nucleotide sequence of SEQ ID NO: 3, and that encodes a fragment, analog or functional derivative of the polypeptide having the amino acid sequence of SEQ ID NO: 4, wherein said fragment, analog or functional derivative has the lytic activity of the EAD of SEQ ID NO: 4.

The present invention provides a nucleic acid molecule comprising a polynucleotide, which hybridizes under stringent conditions to any one of the polynucleotides described in the two preceding paragraphs. Preferably, the present invention provides a nucleic acid molecule comprising a polynucleotide, which hybridizes under stringent conditions to the polynucleotide of SEQ ID NO: 3. The present invention also provides a nucleic acid molecule comprising a polynucleotide that is the complement of the full-length of any one of the polynucleotides described in the two preceding paragraphs. Preferably the present invention provides a nucleic acid molecule comprising a polynucleotide that is the complement of the full-length of the polynucleotide of SEQ ID NO: 3.

PlyP825 CBD Nucleic Acid and Amino Acid Sequences and Variants Thereof

The present invention provides a nucleic acid molecule comprising a polynucleotide encoding a polypeptide having the amino acid sequence of SEQ ID NO: 6. The present invention also provides a nucleic acid molecule, which comprises a polynucleotide that is at least 75% or at least 80% identical to a polynucleotide encoding a polypeptide having the amino acid sequence of SEQ ID NO: 6, and that encodes a polypeptide having the cell wall binding activity of the CBD of SEQ ID NO: 6. The present invention further provides a nucleic acid molecule, which comprises a polynucleotide that is at least 85% or at least 90% identical to a polynucleotide encoding a polypeptide having the amino acid sequence of SEQ ID NO: 6, and that encodes a polypeptide having the cell wall binding activity of the CBD of SEQ ID NO: 6. In various embodiments, the said nucleic acid molecule comprises a polynucleotide that is at least 91% or at least 92% identical to a polynucleotide encoding a polypeptide having the amino acid sequence of SEQ ID NO: 6, and that encodes a polypeptide having the cell wall binding activity of the CBD of SEQ ID NO: 6. Preferably, the said nucleic acid molecule comprises a polynucleotide that is at least 93% or at least 94% identical to a polynucleotide encoding a polypeptide having the amino acid sequence of SEQ ID NO: 6, and that encodes a polypeptide having the cell wall binding activity of the CBD of SEQ ID NO: 6. More preferably, the said nucleic acid molecule comprises a polynucleotide that is at least 95% or at least 96% identical to a polynucleotide encoding a polypeptide having the amino acid sequence of SEQ ID NO: 6, and that encodes a polypeptide having the cell wall binding activity of the CBD of SEQ ID NO: 6. Still more preferably, the said nucleic acid molecule comprises a polynucleotide that is at least 97%, at least 98%, or even at least 99% identical to a polynucleotide encoding a polypeptide having the amino acid sequence of SEQ ID NO: 6, and that encodes a polypeptide having the cell wall binding activity of the CBD of SEQ ID NO: 6.

Furthermore, the present invention provides a nucleic acid molecule comprising a polynucleotide, which encodes a polypeptide having an amino acid sequence that is at least 75% or at least 80% identical to the amino acid sequence of SEQ ID NO: 6, and which has the cell wall binding activity of the CBD of SEQ ID NO: 6. The present invention also provides a nucleic acid molecule comprising a polynucleotide, which encodes a polypeptide having an amino acid sequence that is at least 85% or at least 90% identical to the amino acid sequence of SEQ ID NO: 6, and which has the cell wall binding activity of the CBD of SEQ ID NO: 6. In various embodiments, the said nucleic acid molecule comprises a polynucleotide, which encodes a polypeptide having an amino acid sequence that is at least 91% or at least 92% identical to the amino acid sequence of SEQ ID NO: 6, and which has the cell wall binding activity of the CBD of SEQ ID NO: 6. Preferably, the said nucleic acid molecule comprises a polynucleotide, which encodes a polypeptide having an amino acid sequence that is at least 93% or at least 94% identical to the amino acid sequence of SEQ ID NO: 6, and which has the cell wall binding activity of the CBD of SEQ ID NO: 6. More preferably, the said nucleic acid molecule comprises a polynucleotide, which encodes a polypeptide having an amino acid sequence that is at least 95% or at least 96% identical to the amino acid sequence of SEQ ID NO: 6, and which has the cell wall binding activity of the CBD of SEQ ID NO: 6. Still more preferably, the said nucleic acid molecule comprises a polynucleotide, which encodes a polypeptide having an amino acid sequence that is at least 97%, at least 98%, or even 99% identical to the amino acid sequence of SEQ ID NO: 6, and which has the cell wall binding activity of the CBD of SEQ ID NO: 6.

Furthermore, the present invention provides a nucleic acid molecule comprising a polynucleotide, which encodes a fragment, analog or functional derivative of a polypeptide encoded by a polynucleotide encoding a polypeptide having the amino acid sequence of SEQ ID NO: 6, wherein said fragment, analog or functional derivative has the cell wall binding activity of the CBD of SEQ ID NO: 6. Preferably, the said nucleic acid molecule comprises a polynucleotide, which encodes a fragment, analog or functional derivative of a polypeptide encoded by the polynucleotide of SEQ ID NO: 5, wherein said fragment, analog or functional derivative has the cell wall binding activity of the CBD of SEQ ID NO: 6.

The present invention provides a nucleic acid molecule comprising a polynucleotide, which hybridizes under stringent conditions to any one of the polynucleotides described in the three preceding paragraphs. The present invention also provides a nucleic acid molecule comprising a polynucleotide that is the complement of the full-length of any one of the polynucleotides described in the three preceding paragraphs.

The present invention provides a nucleic acid molecule comprising a polynucleotide having the nucleotide sequence of SEQ ID NO: 5. The present invention also provides a nucleic acid molecule, which comprises a polynucleotide that is at least 75% or at least 80% identical to the nucleotide sequence of SEQ ID NO: 5, and that encodes a polypeptide having the cell wall binding activity of the CBD of SEQ ID NO: 6. The present invention further provides a nucleic acid molecule, which comprises a polynucleotide that is at least 85% or at least 90% identical to the nucleotide sequence of SEQ ID NO: 5, and that encodes a polypeptide having the cell wall binding activity of the CBD of SEQ ID NO: 6. In various embodiments, the said nucleic acid molecule comprises a polynucleotide that is at least 91% or at least 92% identical to the nucleotide sequence of SEQ ID NO: 5, and that encodes a polypeptide having the cell wall binding activity of the CBD of SEQ ID NO: 6. Preferably, the said nucleic acid molecule comprises a polynucleotide that is at least 93% or at least 94% identical to the nucleotide sequence of SEQ ID NO: 5, and that encodes a polypeptide having the cell wall binding activity of the CBD of SEQ ID NO: 6. More preferably, the said nucleic acid molecule comprises a polynucleotide that is at least 95% or at least 96% identical to the nucleotide sequence of SEQ ID NO: 5, and that encodes a polypeptide having the cell wall binding activity of the CBD of SEQ ID NO: 6. Still more preferably, the said nucleic acid molecule comprises a polynucleotide that is at least 97%, at least 98%, or even at least 99% identical to the nucleotide sequence of SEQ ID NO: 5, and that encodes a polypeptide having the cell wall binding activity of the CBD of SEQ ID NO: 6.

Furthermore, the present invention provides a nucleic acid molecule comprising a polynucleotide that is a part of the nucleotide sequence of SEQ ID NO: 5, and that encodes a fragment, analog or functional derivative of the polypeptide having the amino acid sequence of SEQ ID NO: 6, wherein said fragment, analog or functional derivative has the cell wall binding activity of the CBD of SEQ ID NO: 6.

The present invention provides a nucleic acid molecule comprising a polynucleotide, which hybridizes under stringent conditions to any one of the polynucleotides described in the two preceding paragraphs. Preferably, the present invention provides a nucleic acid molecule comprising a polynucleotide, which hybridizes under stringent conditions to the polynucleotide of SEQ ID NO: 5. The present invention also provides a nucleic acid molecule comprising a polynucleotide that is the complement of the full-length of any one of the polynucleotides described in the two preceding paragraphs. Preferably the present invention provides a nucleic acid molecule comprising a polynucleotide that is the complement of the full-length of the polynucleotide of SEQ ID NO: 5.

For a variant polypeptide of the present invention having an amino acid sequence at least, for example, 95% "identical" to the reference amino acid sequence of a reference polypeptide defined by a certain SEQ ID NO, is intended that the amino acid sequence of the variant polypeptide is identical to the reference amino acid sequence, except that the polypeptide sequence may include up to five amino acid alterations per each 100 amino acids of the reference amino acid of the reference polypeptide shown in the respective SEQ ID NO. In other words, to obtain a variant polypeptide having an amino acid sequence at least 95% identical to the reference amino acid sequence of a certain reference SEQ ID NO, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the N-terminal or C-terminal positions of the reference amino acid sequence or anywhere between those terminal positions, interspersed either individually among residues in the reference sequence or in one or more contiguous groups within the reference sequence. As a practical matter, whether any particular polypeptide is at least 90%, 95%, 96%, 97%, 98% or 99% identical to the amino acid sequence of a reference SEQ ID NO can be determined conventionally using appropriate computer programs (i.e., sequence alignment programs) known in the art.

As used herein, a nucleic acid molecule of the present invention is DNA or RNA.

Vectors and Host Cells

The present invention provides recombinant vectors containing nucleic acid molecules of the present invention. In various embodiments, provided is a single recombinant vector containing a single nucleic acid molecule of the present invention. In various other embodiments, provided is a single recombinant vector containing several nucleic acid molecules of the present invention. In still other embodiments, provided are several recombinant vectors each containing a single nucleic acid molecule of the present invention. In still further embodiments, provided are several recombinant vectors each containing several nucleic acid molecule of the present invention.

In various embodiments, the nucleic acid molecule or nucleic acid molecules contained in a single or several vectors according to the present invention are operatively linked to an expression control sequence allowing expression of the polynucleotide or polynucleotides in prokaryotic or eukaryotic host cells. Preferably, the expression control sequence is a promoter or a promoter sequence. Suitable promoters are known to the skilled artisan. In various embodiments, the vector is a plasmid. Other suitable vectors will be readily apparent to the skilled artisan. A recombinant vector according to the present invention may also be called expression vector or expression construct.

The expression constructs according to the present invention may further contain sites for transcription initiation, termination and, in the transcribed region, a ribosome binding site for translation. The coding portion of the EAD and/or CBD of the transcripts expressed by the constructs according to the present invention will preferably include a translation initiating codon at the beginning and a termination codon (UAA, UGA or UAG) appropriately positioned at the end of the polypeptide to be translated.

In various embodiments, the expression vectors according to the present invention will include at least one selectable marker. Suitable selection markers are known to the skilled artisan.

The present invention provides a method of making a recombinant vector comprising inserting a nucleic acid molecule of the present invention into a vector.

The present invention also provides a method of making a recombinant host cell comprising introducing a nucleic acid molecule or a recombinant vector according to the present invention into a host cell.

The present invention also provides a host cell genetically engineered with a nucleic acid molecule or a recombinant vector according to the present invention. In various embodiments, "genetically engineered" means that the host cell is transformed or transfected with a nucleic acid molecule or a recombinant vector according to the present invention. In various embodiments, the genetically engineered host cell according to the present invention contains a polypeptide expressed from a nucleic acid molecule or from a recombinant vector in accordance with the present invention. Representative examples of appropriate host cells include, but are not limited to, bacterial cells such as *E. coli* cells, fungal cells such as yeast cells, insect cells such as *Drosophila* S2 and *Spodoptera* Sf9 cells, animal cells such as CHO, COS, and HEK293 cells, and plant cells. Appropriate culture mediums and conditions for host cells of the present invention are known in the art.

Proteins/Polypeptides

Recombinant proteins of the present invention can be isolated and purified from a host cell of the present invention containing or expressing the proteins/polypeptides by techniques known in the art including, but not limited to, lysis, chromatography, filtration, and centrifugation. In various embodiments, the isolated and/or purified protein according to the present invention is labeled. Preferably, the label is selected from the group consisting of an enzyme label, a radioisotope, a fluorescent label, and biotin.

A protein of the present invention having lytic activity, preferably the PlyP825 endolysin, can be isolated from the host cell prior to administration in methods of controlling *Listeria* contamination and infection according to the present invention, or the host cell containing the recombinant protein can be directly applied or administered without prior isolation of the protein having lytic activity. For example, a host bacterium, which produces the PlyP825 endolysin of the present invention can be applied in methods of controlling *Listeria* contamination and infection according to the present invention where the endolysin would be secreted, for example, into food or foodstuff, onto a surface or in the gut of a subject. The PlyP825 endolysin of the present invention can then attack *Listeria* cells present in such an environment.

The present invention also provides a method of making a polypeptide of the present invention encoded by a nucleic acid molecule of the present invention, wherein the method comprises (i) culturing a genetically engineered host cell of the present invention under conditions such that the polypeptide encoded by a nucleic acid molecule of the present invention is expressed, and (ii) recovering the polypeptide encoded by the nucleic acid molecule. The polypeptide may be expressed in a modified form, such as a fusion protein, and may include not only secretion signals, but also additional heterologous functional regions. For example, a region of additional amino acids, particularly charged amino acids, may be added to the N-terminus of the polypeptide to improve stability and persistence in the host cell, during purification, or during subsequent handling and storage of the polypeptide. Also, peptide moieties may be added to the polypeptide to facilitate purification. Such regions may be removed prior to final preparation of the polypeptide. The addition of peptide moieties to polypeptides of the present invention for, inter alia, inducing secretion, improving stability and/or facilitating purification are familiar to the ones of ordinary skill and belong to routine techniques in the art. A preferred fusion protein comprises a heterologous region from an immunoglobulin that is useful to stabilize and purify proteins.

As one of skill in the art will appreciate, polypeptides of the present invention can be combined with parts of the constant domain of immunoglobulins (IgG), resulting in chimeric polypeptides. These fusion proteins may facilitate purification and may show an increased half-life in vivo.

For many proteins it is known in the art that one or more amino acids may be deleted from the N-terminus or C-terminus without substantial loss of biological function or activity. Here, biological function/activity includes any function and activity of the proteins of the present invention described herein including, but not limited to, any lytic function/activity and cell wall binding function/activity described herein.

In the present invention, since the protein of SEQ ID NO: 2 is a member of the endolysin polypeptide family, deletions of C-terminal amino acids up to the Arg (R) residue at position 143 in SEQ ID NO: 2 retains the lytic activity of the endolysin protein, i.e. the lytic activity to *Listeria* bacterial cells. Accordingly, the present invention provides endolysin polypeptides having one or more residues deleted from the C-terminus of the amino acid sequence of the endolysin protein of SEQ ID NO: 2, up to the Arg residue at position 143 (R143) in the amino acid sequence of SEQ ID NO: 2, and polynucleotides encoding such polypeptides.

The present invention provides polypeptides encoded by the nucleic acid molecules of the present invention. The present invention also provides polypeptides obtainable by methods of making the polypeptides according to the present invention. Therefore, the present invention encompasses and provides each polypeptide that is encoded by any nucleic acid molecule of the present invention. Furthermore, the present invention encompasses and provides each polypeptide that is obtainable by any method of making the polypeptide according to the present invention.

Antibodies

The present invention also provides an antibody or fragment thereof that binds specifically to a polypeptide of the present invention. Preferably, the antibody specifically binds to the full-length polypeptide having the amino acid sequence of SEQ ID NO: 2, 4 or 6. In various embodiments, the antibody specifically binds to the lytic domain of the endolysin polypeptide having the amino acid sequence of SEQ ID NO: 2, wherein the lytic domain comprises the amino acid sequence of residues 1 (M1) to 142 (E142) of SEQ ID NO: 2. In various embodiments, the antibody specifically binds to the cell wall binding domain of the endolysin polypeptide having the amino acid sequence of SEQ ID NO: 2, wherein the cell wall binding domain comprises the amino acid sequence of residues 163 (G163) to 315 (N315) of SEQ ID NO: 2.

In various embodiments, the antibody of the present invention is selected from the group consisting of a monoclonal antibody, a polyclonal antibody, a chimeric antibody, a Fab fragment, a $F(ab')_2$ fragment, and a scFv fragment. In various embodiments, the antibody according to the present invention is labeled. Preferably, the label is selected from the group consisting of an enzyme label, a radioisotope, a fluorescent label, and biotin. The polypeptides of the present invention can be used to raise polyclonal and monoclonal antibodies provided by the present invention. The antibodies of the present invention may be prepared by any of a variety of methods available in the art and known to the skilled artisan.

The antibody fragments provided by the present invention, whether attached to other sequences or not, can also include insertions, deletions, substitutions, or other selected modifications of particular regions or specific amino acids residues, provided the activity of the antibody fragment is not significantly altered or impaired compared to the non-modified antibody or antibody fragment. These modifications can provide for some additional property, such as to remove/add amino acids capable of disulfide bonding. In any case, antibody fragments according to the present invention must possess a bioactive property, such as specific binding to its cognate antigen.

Functional or active regions of the antibodies or antibody fragments of the present invention may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment.

Combinations of Proteins of the Invention with Known *Listeria*-Specific Phages

The present invention provides the combination of a protein of the present invention, preferably an endolysin protein, with one or more other *Listeria*-specific bacteriophages described in the art. Such combinations can be used for controlling *Listeria* contamination and/or infection according to the present invention. In various embodiments concerning the combination of a protein of the present invention with one or more *Listeria* bacteriophages known in the art the protein of the present invention is the lytic domain of an endolysin protein according to the present invention. Preferably, the lytic domain of an endolysin protein according to the present invention is an EAD according to the present invention. In various other embodiments concerning the combination of a protein of the present invention with one or more *Listeria* bacteriophages known in the art the protein of the present invention is the cell wall binding domain of an endolysin protein according to the present invention. Preferably, the cell wall binding domain of an endolysin protein according to the present invention is a CBD to the present invention.

Combinations of Proteins of the Invention with Known Endolysins

Also provided by the present invention is the combination of a protein of the present invention, preferably an endolysin protein, with one or more endolysins from other *Listeria*-specific bacteriophages described in the art. Such combinations can be used for controlling *Listeria* contamination and/or infection according to the present invention. In various embodiments concerning the combination of a protein of the present invention with one or more endolysins from *Listeria* bacteriophages known in the art the protein of the present invention is the lytic domain of an endolysin protein according to the present invention. Preferably, the lytic domain of an endolysin protein according to the present invention is an EAD according to the present invention. In various other embodiments concerning the combination of a protein of the present invention with one or more endolysins from *Listeria* bacteriophages known in the art the protein of the present invention is the cell wall binding domain of an endolysin protein according to the present invention. Preferably, the cell wall binding domain of an endolysin protein according to the present invention is a CBD to the present invention.

Combinations of Proteins of the Invention with Known Lytic Domains

The present invention provides the combination of a protein of the present invention, preferably an endolysin protein, with one or more lytic domains of endolysins from other *Listeria*-specific bacteriophages described in the art. Such combinations can be used for controlling *Listeria* contamination and/or infection according to the present invention. Furthermore, based on sequence homology the skilled person is also able to determine the lytic domain of the endolysins encoded by known phages. In various embodiments concerning the combination of a protein of the present invention with one or more lytic domains of endolysins from *Listeria* bacteriophages known in the art the protein of the present invention is the lytic domain of an endolysin protein according to the present invention. Preferably, the lytic domain of an endolysin protein according to the present invention is an EAD according to the present invention. In various other embodiments concerning the combination of a protein of the present invention with one or more lytic domains of endolysins from *Listeria* bacteriophages known in the art the protein of the present invention is the cell wall binding domain of an endolysin protein according to the present invention. Preferably, the cell wall binding domain of an endolysin protein according to the present invention is a CBD to the present invention.

Also provided by the present invention is the combination of a protein of the present invention, preferably an endolysin protein, with one or more lytic domains of autolysins described in the art. Autolysins are bacteriolytic enzymes that digest the cell-wall peptidoglycan of the bacteria that produce them. Autolysins are involved in cell wall reconstruction during bacterial cell division. Thus, the present invention provides a protein of the present invention, preferably an endolysin protein, in combination with one or more lytic domains of autolysins. Such combinations can be used for controlling *Listeria* contamination and/or infection according to the present invention.

Also provided by the present invention is the combination of a protein of the present invention, preferably an endolysin protein, with one or more lytic domains of bacteriocins described in the art. Bacteriocins are molecules also produced and secreted by microorganisms. They are antibacterial substances of a proteinaceous nature that are produced by different bacterial species. A subclass of bacteriocins consists of enzymes (proteinaceous toxins) which are produced by bacteria to inhibit the growth of similar or closely related concurrence bacterial strain(s) in their habitat. Many bacteria produce antimicrobial bacteriocin peptides. Thus, the present invention provides a protein of the present invention, preferably an endolysin protein, in combination with one or more lytic domains of bacteriocins. Such combinations can be used for controlling *Listeria* contamination and/or infection according to the present invention. Based on sequence homology the skilled person is able to determine the lytic domain of bacteriocins known in the art.

Also provided by the present invention is the combination of a protein of the present invention, preferably an endolysin protein, with one or more antimicrobial peptides. Antimicrobial peptides are ubiquitous, gene-encoded natural antibiotics that have gained recent attention in the search for new antimicrobials to combat infectious disease. Antimicrobial peptides generally have a length between 12 and 50 amino acids. The amphipathicity of the antimicrobial peptides allows to partition into the membrane lipid bilayer. The ability to associate with membranes is a definitive feature of antimicrobial peptides. Thus, the present invention provides a protein of the present invention, preferably an endolysin protein, in combination with one or more antimicrobial peptides. Such combinations can be used for controlling *Listeria* contamination and/or infection according to the present invention.

Combinations of Proteins of the Invention with Known Cell Wall Binding Domains

The present invention provides the combination of a protein of the present invention, preferably an endolysin protein, with one or more cell wall binding domains of endolysins from other *Listeria* bacteriophages described in the art. Such combinations can be used for controlling *Listeria* contamination and/or infection according to the present invention. As for the lytic domain encoded by the endolysins from known phages, based on sequence homology the skilled person is also able to determine the cell wall binding domain of the endolysins encoded by known phages. In various embodiments concerning the combination of a protein of the present invention with one or more cell wall binding domains of endolysins from *Listeria* bacteriophages known in the art the protein of the present invention is the lytic domain of an endolysin protein according to the present invention. Preferably, the lytic domain of an endolysin protein according to the present invention is an EAD according to the present invention. In various other embodiments concerning the combination of a protein of the present invention with one or more cell wall binding domains of endolysins from *Listeria* bacteriophages known in the art the protein of the present invention is the cell wall binding domain of an endolysin protein according to the present invention. Preferably, the cell wall binding domain of an endolysin protein according to the present invention is a CBD to the present invention.

Also provided by the present invention is the combination of a protein of the present invention, preferably an endolysin protein, with one or more cell wall binding domains of autolysins known in the art. Thus, the present invention provides a protein of the present invention, preferably an endolysin protein, in combination with one or more cell wall binding domains of autolysins. Such combinations can be used for controlling *Listeria* contamination and/or infection according to the present invention. Based on sequence homology the skilled person is able to determine the cell wall binding domain of autolysins known in the art.

Also provided by the present invention is the combination of a protein of the present invention, preferably an endolysin protein, with one or more cell wall binding domains of bacteriocins described in the art. Thus, the present invention provides a protein of the present invention, preferably an endolysin protein, in combination with one or more cell wall binding domains of bacteriocins. Such combinations can be used for controlling *Listeria* contamination and/or infection according to the present invention. Based on sequence homology the skilled Chimeric Proteins The present invention further provides a chimeric protein comprising a protein according to the present invention, preferably an endolysin protein of the present invention, and one or more heterologous proteins. Preferably, the chimeric protein of the present invention has endolysin activity. More preferably, the chimeric protein has the endolysin activity of the polypeptide of SEQ ID NO: 2. In various embodiments, the heterologous protein is a heterologous endolysin protein. In various embodiments, the chimeric protein according to the present invention comprises the lytic domain of an endolysin of the present invention and one or more heterologous proteins, wherein the lytic domain has the lytic activity of the EAD of SEQ ID NO: 4. Preferably, the lytic domain is the lytic domain of the endolysin of SEQ ID NO: 2 or the EAD of SEQ ID NO: 4. In various other embodiments, the chimeric protein according to the present invention comprises the cell wall binding domain of an endolysin of the present invention and one or more heterologous proteins, wherein the cell wall binding domain has the cell wall binding activity of the EAD of SEQ ID NO: 6. Preferably, the cell wall binding domain is the cell wall binding domain of the endolysin of SEQ ID NO: 2 or the CBD of SEQ ID NO: 6.

The present invention also provides a chimeric protein comprising an endolysin protein according to the present invention, wherein a catalytic domain of the endolysin protein is substituted with a catalytic domain of a heterologous endolysin protein, wherein the chimeric protein has endolysin activity. Preferably, such a chimeric protein has the endolysin activity of the polypeptide of SEQ ID NO: 2. In various embodiments, the catalytic domain of the endolysin protein of the present invention is the lytic domain, i.e., the EAD, and the catalytic domain of the heterologous endolysin protein is also its lytic domain. Accordingly, in various embodiments, the present invention provides a chimeric protein comprising an endolysin protein according to the present invention, wherein the lytic domain (i.e., the EAD) is substituted with the lytic domain of a heterologous endolysin protein, wherein the chimeric protein has endolysin activity. Preferably, the chimeric protein has the endolysin activity of the polypeptide of SEQ ID NO: 2. In various embodiments, the present invention provides a chimeric protein comprising an endolysin protein according to the present invention, wherein the cell wall binding domain (i.e., the CBD) is substituted with the cell wall binding domain of a heterologous endolysin protein, wherein the chimeric protein has endolysin activity. Preferably, such a chimeric protein has the endolysin activity of the polypeptide of SEQ ID NO: 2.

The present invention further provides a chimeric protein comprising an endolysin protein of the present invention and one or more lytic domains (i.e., EADs) and/or one or more cell wall binding domains (i.e., CBDs) of other known endolysins from *Listeria* bacteriophages known in the art.

The present invention also provides a chimeric protein comprising a lytic domain of the present invention and one or more lytic domains (i.e., EADs) and/or one or more cell wall binding domains (i.e., CBDs) of other known endolysins from *Listeria* bacteriophages known in the art.

The present invention also provides a chimeric protein comprising a cell wall binding domain of the present invention and one or more lytic domains (i.e., EADs) and/or one or more cell wall binding domains (i.e., CBDs) of other known endolysins from *Listeria* bacteriophages known in the art.

In various embodiments, the chimeric proteins according to the present invention comprise more than one endolysin protein of the present invention. That is, the chimeric proteins according to the present invention may comprise tandem repeats of an endolysin protein of the present invention. Furthermore, in various embodiments the chimeric proteins according to the present invention comprise more than one lytic domain of the present invention. That is, the chimeric proteins according to the present invention may comprise one or more tandem repeats of a lytic domain of the present invention. Still further, in various embodiments the chimeric proteins according to the present invention comprise more than one cell wall binding domain of the present invention. That is, the chimeric proteins according to the present invention may comprise one or more tandem repeats of a cell wall binding domain of the present invention.

The present invention also provides chimeric proteins comprising the combination of a protein of the present invention with one or more endolysins from known *Listeria*-specific bacteriophages as described above.

The present invention also provides chimeric proteins comprising the combination of a protein of the present invention with one or more lytic domains from known endolysins as described above.

The present invention also provides chimeric proteins comprising the combination of a protein of the present invention with one or more lytic domains from known autolysins as described above.

The present invention also provides chimeric proteins comprising the combination of a protein of the present invention with one or more lytic domains from known bacteriocins as described above.

The present invention also provides chimeric proteins comprising the combination of a protein of the present invention with one or more antimicrobial peptides as described above.

The present invention also provides chimeric proteins comprising the combination of a protein of the present invention with one or more cell wall binding domains from known endolysins as described above.

The present invention also provides chimeric proteins comprising the combination of a protein of the present invention with one or more cell wall binding domains from known autolysins as described above.

The present invention also provides chimeric proteins comprising the combination of a protein of the present invention with one or more cell wall binding domains from known bacteriocins as described above.

Combinations of Phages of the Invention with Known Phages

The present invention provides the combination of a phage of the present invention with one or more bacteriophages, preferably known *Listeria*-specific phages, described in the art. Such combinations can be used for controlling *Listeria* contamination and/or infection according to the present invention. A preferred phage used in phage combinations according to the present invention is phage P825.

Compositions and Solutions

The present invention provides compositions comprising phage combinations and/or protein combinations of the invention as described herein above. Specifically, such a combination is the combination of a protein of the present invention with one or more known *Listeria* bacteriophages. Furthermore, such a combination is particularly the combination of a protein of the present invention with one or more endolysins from known *Listeria* bacteriophages. Such a combination is also particularly the combination of a protein of the present invention with one or more lytic or cell wall binding domains of endolysins from known *Listeria* bacteriophages. Still further, such a combination is the combination of a phage of the present invention, preferably phage P825, with one or more known *Listeria* bacteriophages.

The present invention also provides compositions comprising chimeric proteins according to the present invention. In general, the present invention provides a composition comprising a protein or polypeptide according to the present invention. The present invention also provides a composition comprising a nucleic acid molecule or a vector according to the present invention. The present invention further provides a composition comprising a host cell according to the present invention. The present invention further provides a composition comprising a protein or polypeptide according to the present invention. The present invention further provides a composition comprising a chimeric lysin according to the present invention. Still further, the present invention provides a composition comprising a phage of the present invention, preferably phage P825.

In various embodiments, a composition of the present invention further comprises listeriolysin, a surface disinfectant, an antibiotic, a surfactant, a lytic enzyme, or a bacteriophage specific for bacterial contaminants other than *Listeria* bacteria.

In various embodiments, a composition according to the present invention is a pharmaceutical composition.

In various embodiments, a composition according to the present invention is a disinfecting composition.

In various embodiments, a composition according to the present invention is a diagnostic composition. A phage of the present invention, preferably phage P825, is suitable for detecting the presence of *Listeria* bacteria according to the present invention. Therefore, a diagnostic composition according to the present invention preferably comprises a phage of the present invention, more preferably phage P825.

In various embodiments, a composition of the present invention is an antibiotic for use in therapeutic and non-therapeutic applications according to the present invention.

The present invention provides solutions, preferably disinfecting solutions, comprising phage combinations and protein combinations of the invention as described herein above. Specifically, such a combination is the combination of a protein of the present invention with one or more known *Listeria* bacteriophages. Furthermore, such a combination is particularly the combination of a protein of the present invention with one or more endolysins from known *Listeria* bacteriophages. Such a combination is also particularly the combination of a protein of the present invention with one or more lytic or cell wall binding domains of endolysins from known *Listeria* bacteriophages. Still further, such a combination is the combination of a phage of the present invention, preferably phage P825, with one or more known *Listeria* bacteriophages.

The present invention also provides solutions, preferably disinfecting solutions, comprising chimeric proteins according to the present invention. In general, the present invention provides a solution, preferably a disinfecting solution, comprising a phage or protein or polypeptide according to the present invention. The present invention also provides a solution, preferably a disinfecting solution, comprising a nucleic acid molecule or a vector according to the present invention. The present invention further provides a solution, preferably a disinfecting solution, comprising a host cell according to the present invention.

Products

The present invention provides products comprising chimeric proteins according to the present invention. In general, the present invention provides a product comprising a protein or polypeptide according to the present invention, including any fragments, analogs or functional derivatives thereof having endolysin activity. The present invention further provides a product comprising a chimeric lysin according to the present invention. Still further, the present invention provides a product comprising a phage of the present invention, preferably phage P825.

The present invention also provides products comprising phage combinations and/or protein combinations of the invention as described herein above. Specifically, such a combination is the combination of a protein of the present invention with one or more known *Listeria* bacteriophages. Furthermore, such a combination is particularly the combination of a protein of the present invention with one or more endolysins from known *Listeria* bacteriophages. Such a combination is also particularly the combination of a protein of the present invention with one or more lytic or cell wall binding domains of endolysins from known *Listeria* bacteriophages. Still further, such a combination is the combination of a phage of the present invention, preferably phage P825, with one or more known *Listeria* bacteriophages.

In various embodiments, a product of the present invention further comprises listeriolysin, a surface disinfectant, an antibiotic, a surfactant, a lytic enzyme, or a bacteriophage specific for bacterial contaminants other than *Listeria* bacteria.

In various embodiments, a product according to the present invention is a food product. Preferably, the food product is any of a dairy product, a fruit product and a vegetable product.

Methods for Controlling *Listeria* Contamination

The present invention provides a method for controlling *Listeria* contamination, preferably for sanitizing and/or disinfecting *Listeria* contamination, comprising applying a nucleic acid molecule of the present invention, a vector of the present invention, a host cell of the present invention, a protein or polypeptide of the present invention, or a chimeric lysin of the present invention to the present invention to the site of *Listeria* contamination, with the proviso that the method is not a therapeutic method.

The present invention provides a method for controlling *Listeria* contamination, preferably for sanitizing and/or disinfecting *Listeria* contamination, comprising applying a phage or a composition or solution according to the present invention to the site of *Listeria* contamination, with the proviso that the method is not a therapeutic method.

The present invention provides a composition or solution according to the present invention for use in therapy and/or prophylaxis.

The present invention provides a phage according to the present invention for use in diagnosis. Preferably, the bacteriophage for use in diagnosis is phage P825.

In various embodiments, controlling *Listeria* contamination according to the present invention is sanitizing and/or disinfecting *Listeria* contamination.

In various embodiments, controlling *Listeria* contamination according to the present invention is non-therapeutically treating *Listeria* contamination. Preferably, treating *Listeria* contamination is eradicating or removing undesired colonization of *Listeria* bacteria.

In the present invention, "*Listeria* contamination" means "undesired *Listeria* contamination". In the present invention, undesired *Listeria* contamination includes, but is not limited to, contamination of pathogenic *Listeria* bacteria. Here, pathogenic means exhibiting pathogenicity to human beings and/or animals. *Listeria monocytogenes* is pathogenic to both human and animals. Therefore, in the present invention controlling *Listeria* contamination preferably is controlling *Listeria monocytogenes* contamination.

In various embodiments, controlling *Listeria* contamination is cleaning from *Listeria* contamination.

In various embodiments, controlling *Listeria* contamination according to the present invention is *Listeria* decontamination. As used herein, *Listeria* decontamination means that after applying a phage or a composition or solution according to the present invention to the site of *Listeria* contamination the number of *Listeria* bacteria is reduced compared to the number of *Listeria* bacteria prior to applying a phage or a composition or solution according to the present invention to the site of *Listeria* contamination. The same holds for applying a nucleic acid molecule of the present invention, a vector of the present invention, a host cell of the present invention, a protein or polypeptide of the present invention, or a chimeric lysin of the present invention in *Listeria* decontamination.

The present invention provides a combined treatment for controlling *Listeria* contamination, which comprises applying a nucleic acid molecule of the present invention, a vector of the present invention, a host cell of the present invention, a protein or polypeptide of the present invention, or a chimeric lysin of the present invention and a further/additional anti-*Listeria* agent to the site of *Listeria* contamination, with the proviso that the method is not a therapeutic method. The present invention also provides a combined treatment for controlling *Listeria* contamination, which comprises applying a phage or composition or solution according to the present invention and a further/additional anti-*Listeria* agent to the site of *Listeria* contamination, with the proviso that the method is not a therapeutic method. Here, the further/additional anti-*Listeria* agent preferably is a disinfectant, an antimicrobial agent effective against *Listeria* bacteria, an enzyme, or a surfactant. The group of such antimicrobial agents effective against *Listeria* bacteria includes, but is not limited to, vancomycin, danofloxacin, and neomycin. Furthermore, in case of an enzyme as further/ additional anti-*Listeria* agent to be used in the present invention, the group of suitable enzymes includes enzymes aiding in breaking up biofilms. Such enzymes are known in the art and include, but are not limited to, polysaccharide depolymerases and proteases. The surfactant is particularly useful to solubilize and remove dirt so that the *Listeria* bacteria are accessible to the lytic proteins of the present invention.

The further/additional anti-*Listeria* agent may be applied to the site of *Listeria* contamination before or after applying a phage or a composition or solution according to the present invention to the site of *Listeria* contamination. This applies in analogy to the use of a nucleic acid molecule of the present invention, a vector of the present invention, a host cell of the present invention, a protein or polypeptide of the present invention, or a chimeric lysin of the present invention in a combined treatment comprising a further/additional anti-*Listeria* agent as used herein.

The present invention further provides a combined treatment for controlling *Listeria* contamination, which comprises a thermal treatment of the site of *Listeria* contamination, and subsequently applying a nucleic acid molecule of the present invention, a vector of the present invention, a host cell of the present invention, a protein or polypeptide of the present invention, or a chimeric lysin of the present invention to the site of *Listeria* contamination, with the proviso that the method is not a therapeutic method. The present invention further provides a combined treatment for controlling *Listeria* contamination, which comprises a thermal treatment of the site of *Listeria* contamination, and subsequently applying a phage or a composition or solution according to the present invention to the site of *Listeria* contamination, with the proviso that the method is not a therapeutic method. Specifically, thermal treatment of the site of *Listeria* contamination is heat treatment of the site of *Listeria* contamination, more preferably heat treatment at a temperature of at least 70° C., or 71° C. Still more preferably, thermal treatment is heat treatment at a temperature of at least 72° C., or 73° C. Even more preferably, thermal treatment is heat treatment at a temperature of at least 74° C., or 75° C.

The present invention provides a combined treatment for controlling *Listeria* contamination, which comprises applying a nucleic acid molecule of the present invention, a vector of the present invention, a host cell of the present invention, a protein or polypeptide of the present invention, or a chimeric lysin of the present invention and an irradiation treatment of the site of *Listeria* contamination, with the proviso that the method is not a therapeutic method. The present invention also provides a combined treatment for controlling *Listeria* contamination, which comprises applying a phage or a composition or solution according to the present invention and an irradiation treatment of the site of *Listeria* contamination, with the proviso that the method is not a therapeutic method. As used herein, irradiation treatment means subjecting the site of *Listeria* contamination to ionizing radiation, also called ionizing energy. The radiation used to treat the site of *Listeria* contamination may be applied before or after a phage or a composition or solution according to the present invention is applied to the site of *Listeria* contamination. This applies in analogy to the use of a nucleic acid molecule of the present invention, a vector of the present invention, a host cell of the present invention, a protein or polypeptide of the present invention, or a chimeric lysin of the present invention in a combined treatment comprising irradiation treatment as used herein.

The present invention provides a combined treatment for controlling *Listeria* contamination, which comprises applying a nucleic acid molecule of the present invention, a vector of the present invention, a host cell of the present invention, a protein or polypeptide of the present invention, or a chimeric lysin of the present invention and high intensity light emission treatment to the site of *Listeria* contamination, with the proviso that the method is not a therapeutic method. The present invention also provides a combined treatment for controlling *Listeria* contamination, which comprises applying a phage or a composition or solution according to the present invention and high intensity light emission treatment to the site of *Listeria* contamination, with the proviso that the method is not a therapeutic method. Specifically, high intensity light emission treatment may be performed by a pulsed power source, as described in MacGregor et al. 1998 ("Light inactivation of food-related pathogenic bacteria using a pulsed power source", *Letters in Applied Microbiology* 27(2):67-70). The high intensity light emission treatment may be applied to the site of *Listeria* contamination before or after a phage or a composition or solution according to the present invention is applied to the site of *Listeria* contamination. This applies in analogy to the use of a nucleic acid molecule of the present invention, a vector of the present invention, a host cell of the present invention, a protein or polypeptide of the present invention, or a chimeric lysin of the present invention in a combined treatment comprising high intensity light emission treatment as used herein.

A nucleic acid molecule of the present invention, a vector of the present invention, a host cell of the present invention, a protein or polypeptide of the present invention, or a chimeric lysin of the present invention can be applied on or into food or food products. Similarly, phages, compositions and solutions of the present invention can be applied on or into food or food products. Therefore, in various embodiments controlling *Listeria* contamination, preferably sanitizing and/or disinfecting *Listeria* contamination, is controlling *Listeria* contamination of food or a food product.

In various embodiments, controlling *Listeria* contamination, preferably sanitizing and/or disinfecting *Listeria* contamination, is controlling *Listeria* contamination of a solid surface. In various embodiments, such a solid surface is the surface of a food package, a food storage container or food processing equipment. The surface of food processing equipment includes the various physical sites within the food processing facilities/equipment.

The present invention provides food or a food product comprising a nucleic acid molecule of the present invention, a vector of the present invention, a host cell of the present invention, a protein or polypeptide of the present invention, or a chimeric lysin of the present invention. The present invention also provides food or a food product comprising a phage or a composition or solution according to the present invention.

The present invention further provides a food package or food storage container comprising a nucleic acid molecule of the present invention, a vector of the present invention, a host cell of the present invention, a protein or polypeptide of the present invention, or a chimeric lysin of the present invention. The present invention still further provides a food package or food storage container comprising a phage or a composition or solution according to the present invention. In various embodiments, the nucleic acid molecule, vector, host cell, protein or polypeptide, or chimeric lysin of the present invention is introduced into the food package or food storage container prior to sealing the food package or food storage container. In various embodiments, a phage or composition or solution according to the present invention is introduced into the food package or food storage container prior to sealing the food package or food storage container. In various embodiments, the food, food product, food package or food storage container further comprises a further/additional anti-microbial agent. Here, the further/additional antimicrobial agent preferably is an antimicrobial agent effective against *Listeria* bacteria or other pathogenic bacteria. In various embodiments, the food, food product, food package or food storage container of the present invention has undergone thermal treatment prior to introducing the nucleic acid molecule, vector, host cell, protein or polypeptide, or chimeric lysin of the present invention to the food, food product, food package or food storage container. In various embodiments, the food, food product, food package or food storage container of the present invention has undergone thermal treatment prior to introducing a phage or the composition or solution of the present invention to the food, food product, food package or food storage container. Specifically, thermal treatment of the food, food product, food package or food storage container of the present invention is heat treatment of the food, food product, food package or food storage container of the present invention, more preferably heat treatment at a temperature of at least 70° C., or 71° C. Still more preferably, thermal treatment is heat treatment at a temperature of at least 72° C., or 73° C. Even more preferably, thermal treatment is heat treatment at a temperature of at least 74° C., or 75° C.

In the present invention, applying a phage or a composition or solution according to the present invention to the site of *Listeria* contamination includes incubating the site of *Listeria* contamination with a phage or a composition or solution according to the present invention. This applies in analogy to the use of a nucleic acid molecule of the present invention, a vector of the present invention, a host cell of the present invention, a protein or polypeptide of the present invention, or a chimeric lysin of the present invention as used herein. In the present invention, applying a phage or a composition or solution according to the present invention to the site of *Listeria* contamination also includes administering a phage or a composition or solution according to the present invention to the site of *Listeria* contamination. This applies in analogy to the use of a nucleic acid molecule of the present invention, a vector of the present invention, a host cell of the present invention, a protein or polypeptide of the present invention, or a chimeric lysin of the present invention as used herein.

The nucleic acid molecule, vector, host cell, protein or polypeptide, chimeric lysin, phage, composition or solution according to the present invention may be applied to the food, food product, food package or food storage container of the present invention by a number of means, including, but not limited to, admixing the nucleic acid molecule, vector, host cell, protein or polypeptide, chimeric lysin, phage, composition or solution into the food or food product, or spraying the nucleic acid molecule, vector, host cell, protein or polypeptide, chimeric lysin, phage, composition or solution according to the present invention into the food package or food storage container. Likewise, in the present invention the nucleic acid molecule, vector, host cell, protein or polypeptide, endolysin protein, chimeric lysin, phage, composition or solution according to the present invention may be applied to food processing facilities/equipment by a number of means including, but not limited to, spraying the nucleic acid molecule, vector, host cell, protein or polypeptide, endolysin protein, chimeric lysin, phage, composition or solution onto the food processing facilities/equipment and/or directly applying the nucleic acid molecule, vector, host cell, protein or polypeptide, chimeric lysin, phage, composition or solution to the food processing facilities/equipment. Said applications significantly reduce the numbers of *Listeria* bacteria.

The concentration of a protein according to the present invention, preferably an endolysin protein, for administration on or into food, food products, foodstuff and/or into various physical sites within food processing plants can be determined by one of skill in the art. That is, a suitable concentration is, for example, a concentration that provides for effectively controlling *Listeria* contamination according to the present invention. In various embodiments, the concentration is contemplated to be in the range of about 0.1-100 μg/ml, including the range of about 1-10 μg/ml and 0.5-5 μg/ml. In various embodiments, the concentration is contemplated to be in the range of about 1-5 μg/ml, 5-10 μg/ml, or 10-20 μg/ml. In various other embodiments, the concentration is contemplated to be in the range of about 20-40 μg/ml, 40-60 μg/ml, 60-80 μg/ml, or 80-100 μg/ml. The endolysin provided by the present invention can be applied in a liquid or a powdered form to food, food products, foodstuff, and/or food processing equipment. The nucleic acid molecule, vector, host cell, protein or polypeptide, chimeric lysin, phage, composition or solution of the present invention is administered until a successful reduction of the *Listeria* contamination is achieved or until the amount of *Listeria* bacteria is substantially reduced.

The present invention also provides the use of a nucleic acid molecule of the present invention, a vector of the present invention, a host cell of the present invention, or a protein or polypeptide of the present invention in a non-therapeutic method for controlling *Listeria* contamination according to the present invention as described herein above.

Methods for Controlling *Listeria* Infection

The present invention provides a method for treating and/or preventing *Listeria* infection of a subject comprising administering a phage or a composition or solution of the present invention to the subject.

The present invention also provides a method for treating and/or preventing *Listeria* infection of a subject comprising administering a nucleic acid molecule of the present invention, a vector of the present invention, a host cell of the present invention, a protein or polypeptide of the present invention, or a chimeric lysin of the present invention to the subject.

The methods for treating and/or preventing *Listeria* infection according to the present invention include treating and/or preventing a disease or condition caused by a *Listeria* infection. In various embodiments, the disease or condition caused by a *Listeria* infection is listeriosis. Listeriosis is an infection resulting form the ingestion of food or foodstuff contaminated by *Listeria* bacteria. In various embodiments listeriosis is caused by a *Listeria* infection resulting form the ingestion of food or foodstuff contaminated by *Listeria*. Preferably, listeriosis according to the present invention is caused by a *L. monocytogenes* infection resulting form the ingestion of food or foodstuff contaminated by *L. monocytogenes*. In various other embodiments the disease or condition caused by a *Listeria* infection is brain abscess, hepatitis, peritonitis, arthritis, gastroenteritis, encephalitis, sepsis, local wound infection, and inflammation of conjunctiva and cornea. Preferably, the disease or condition caused by a *Listeria* infection is listeriosis.

In various embodiments of the therapeutic methods of treatment according to the present invention the subject is a subject suffering from a *Listeria* infection or a subject supposed to suffer from a *Listeria* infection. In various embodiments of the therapeutic methods of treatment according to the present invention the subject is a subject at risk for a *Listeria* infection.

In various embodiments of the therapeutic methods of treatment according to the present invention the *Listeria* infection is a *Listeria monocytogenes* infection.

In various embodiments of the therapeutic methods of treating and/or preventing a disease or condition caused by a *Listeria* infection according to the present invention the disease or condition caused by a *Listeria* infection is a disease or condition caused by a *Listeria monocytogenes* infection.

In the present invention, the subject is a mammal including animals and human beings. In various embodiments, the subject preferably is a human being, more preferably a patient in need of a method for treating and/or preventing *Listeria* infection according to the present invention.

In various embodiments, the subject is a pregnant woman. In various other embodiments, the subject is a newborn baby. In various other embodiments, the subject is an elderly person, preferably a person of at least 60 years of age, more preferably a person of at least 65 years of age, still more preferably a person of at least 70 years of age. Even more preferably, the elderly person is a person of at least 75 years of age. In still more preferred embodiments, the elderly person is a person of at least 80 years of age.

The present invention provides a kit comprising a nucleic acid molecule of the present invention, a vector of the present invention, a host cell of the present invention, a protein or polypeptide of the present invention, or a chimeric lysin of the present invention. The present invention also provides a kit comprising a phage or a composition or solution of the present invention. In various embodiments, the kit according to the present invention is a kit for use in a therapeutic or non-therapeutic method according to the present invention, or a kit for carrying out a therapeutic or non-therapeutic method according to the present invention. In various other embodiments, the kit according to the present invention is a kit for controlling *Listeria* contamination according to the present invention. In various embodiments, the kit is a diagnostic kit.

In various embodiments, the pharmaceutical composition according to the present invention comprises optionally a pharmaceutically acceptable carrier. The term "pharmaceutically acceptable carrier" includes, but is not limited to, a non-toxic solid, semisolid or liquid filler, diluent, encapsulating material or formulation auxiliary of any type. By "pharmaceutically acceptable" is meant a material that is not biologically or otherwise undesirable, i.e., the material may be administered to a subject without causing any undesirable biological effects or interacting in a deleterious manner with any of the other components of the medicament/pharmaceutical composition in which it is contained. The carrier would naturally be selected to minimize any degradation of the active ingredient and to minimize any adverse side effects in the subject, as would be well known to one of skill in the art. Pharmaceutical carriers are known to those skilled in the art. Suitable carriers and their formulations are described in Remington: The Science and Practice of Pharmacy ($19^{th}$ ed.) ed. A. R. Gennaro, Mack Publishing Company, Easton, Pa. 1995. Typically, an appropriate amount of a pharmaceutically acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. These may be targeted to a particular cell type via antibodies, receptors, or receptor ligands. It will be apparent to those persons skilled in the art that certain carriers may be more preferable depending upon, for instance, the route of administration and concentration of composition being administered.

In the therapeutic methods of treatment according to the present invention, the dosage or dosages to be administered to a subject will vary with the age, condition, sex and extent of the *Listeria* infection and/or disease or condition caused by a *Listeria* infection in the subject, route of administration, or whether other drugs are included in the regimen. The dosage or dosages to be administered to a subject can be determined by one of skill in the art. Furthermore, the dosage to be administered to a subject can be adjusted by the individual physician in the event of any counter indications.

Pharmaceutical compositions of the present invention may be administered by any suitable route of administration including, but not limited to, oral administration, rectal administration, parenteral administration, intravaginal administration, intraperitoneal administration, topical administration (as by powders, ointments, drops or transdermal patch), buccal administration, administration by inhalant or by nasal administration. As used herein, nasal administration, including topical intranasal administration, means delivery of a phage or a composition or solution of the present invention into the nose and nasal passages through one or both of the nares, and can comprise delivery by a spraying mechanism or droplet mechanism, or through aerosolization of a phage or the composition or solution. This applies in analogy to the use of a nucleic acid molecule of the present invention, a vector of the present invention, a host cell of the present invention, a protein or polypeptide of the present invention, or a chimeric lysin of the present invention as used herein. Administration of a phage or the composition or solution by inhalant can be through the nose or mouth via delivery by a spraying or droplet mechanism. Delivery can also be directly to any area of the respiratory system (e.g., lungs) via intubation. This applies in analogy to the use of a nucleic acid molecule of the present invention, a vector of the present invention, a host cell of the present invention, a protein or polypeptide of the present invention, or a chimeric lysin of the present invention as used herein.

The term "parenteral" as used herein refers to modes of administration, which include, but are not limited to, intravenous, intramuscular, intraperitoneal, subcutaneous and intra-articular injection and infusion.

In various embodiments, the dosage of administration for the phage P825 is contemplated to be in the range of about $10^3$ to about $10^{13}$ pfu/per kg bodyweight/per day, preferably in the range of about $10^{12}$ pfu/per kg bodyweight/per day.

In various embodiments, the dosage of administration for the PlyP825 endolysin is contemplated to be in the range of about 2-2000 ng/per g bodyweight/per day, preferably in the range of about 20-200 ng/per g bodyweight/per day.

Pharmaceutical compositions according to the present invention may include carriers, thickeners, diluents, buffers, preservatives, surface active agents and the like in addition to the active ingredient of choice.

Formulations for topical administration of a phage or a composition or solution according to the present invention may include ointments, lotions, creams, gels, drops, suppositories, sprays, liquids and powders. Also, formulations for topical administration of a nucleic acid molecule of the present invention, a vector of the present invention, a host cell of the present invention, a protein or polypeptide of the present invention, or a chimeric lysin of the present invention may include ointments, lotions, creams, gels, drops, suppositories, sprays, liquids and powders.

The addition of conventional pharmaceutical carriers, aqueous, powder or oily bases, thickeners and the like may be necessary or desirable in formulations for topical administration of compositions according to the present invention.

In the present invention, food, foodstuff, and food products include, but are not limited to, dairy products, meat products, fish products, unpasteurized food products, fruits, vegetables and salads. As used herein, the term "dairy product" is intended to include any food product made using milk or milk products, including, but not limited to, milk, yoghurt, ice cream, cheese, butter, and cream. In various embodiments, the milk is raw milk or milk that has been pasteurized. As used herein, the term "meat product" is intended to include any food product, which contains animal tissue, including, but not limited to, beef, pork, and poultry. The term "ready to eat meat product" is intended to include any meat product, which does not require cooking prior to consumption, including, but not limited to, pates, hot dogs, bologna, salami, and cold cuts. As used herein, the term "fish product" is intended to include any food product, which contains tissue from an aquatic animal, including, but not limited to, lobster, crab, fresh water and saltwater fish and other seafoods. As used herein, the term "unpasteurized food product" is intended to include any food product, which is prepared using unpasteurized primary ingredients and which does not undergo a final (listeriocidal) heat treatment. As used herein, the term "salad" is intended to include any food product, which contains mixtures of vegetables or fruits, and particularly such mixtures as are presented for consumers to choose from in a display commonly referred to as a "salad bar".

Method for Detecting *Listeria* Bacteria

The present invention provides a method for detecting the presence of *Listeria* bacteria according to the present invention, preferably *Listeria monocytogenes*, comprising (i) providing a sample suspected to contain *Listeria* bacteria, preferably *L. monocytogenes*; (ii) incubating the sample of (i) with a phage or a composition according to the present invention, preferably a diagnostic composition; and (iii) detecting in the sample of (ii) the presence of lysis of *Listeria* bacteria, preferably *L. monocytogenes*, or lysis activity of phage P825 against the *Listeria* bacteria, preferably *L. monocytogenes*, contained in the sample, wherein the presence of lysis of *Listeria* bacteria, preferably *L. monocytogenes*, or lysis activity of a phage of the invention, preferably. P825, against *Listeria* bacteria, preferably *L. monocytogenes*, is indicative of the presence of *Listeria* bacteria, preferably *L. monocytogenes*. In various embodiments, the sample of (i) is obtained from a food product, a food processing equipment, a food storage container, or a patient suspected of suffering from a bacterial contamination comprising *Listeria* bacteria, preferably *L. monocytogenes*.

Further Characteristics of PlyP825

Figure 5:
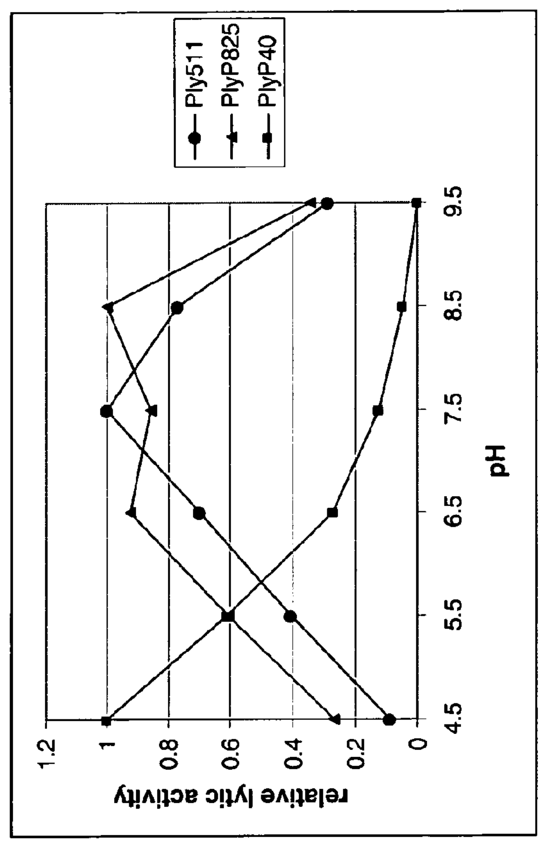
FIG. 5 shows a comparison of the relative lytic activity of endolysins Ply511, PlyP40, and PlyP825 as a function of the pH.

The pH optimum for the lytic activity of endolysin PlyP825 was determined (Example 5 and FIG. 5). PlyP825 exhibit highest lytic activity at neutral to slightly alkaline (basic) pH. Thus, endolysin PlyP825 has a pH optimum at neutral to slightly alkaline (basic) pH. In various embodiments, the endolysin provided by the present invention is characterized as having a pH optimum at about pH 8.5 with respect to its lytic activity. In various other embodiments, the endolysin provided by the present invention is characterized as exhibiting improved lytic activity at a pH of about 5.5, about 6.5 or about 7.5.

Figure 6:
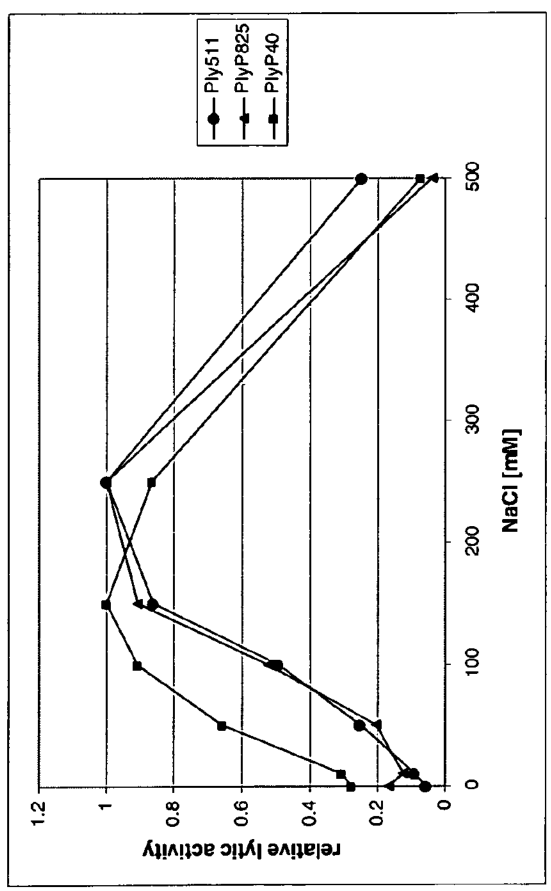
FIG. 6 shows a comparison of the relative lytic activity of endolysins Ply511, PlyP40, and PlyP825 as a function of the salt concentration.

The salt optimum (NaCl) for the lytic activity of endolysin PlyP825 was determined (Example 6 and FIG. 6). PlyP825 exhibits highest lytic activities in the concentration range of about 150-250 mM NaCl. Thus, endolysin PlyP825 has a salt (NaCl) optimum of about 150-250 mM NaCl. In various embodiments, the endolysin provided by the present invention is characterized as having a salt (NaCl) optimum at a concentration in the range of about 150-250 mM NaCl. In various other embodiments, the endolysin provided by the present invention is characterized as having a salt (NaCl) optimum at a concentration of any one of about 150 mM, about 200 mM or 250 mM NaCl.

Figure 7:
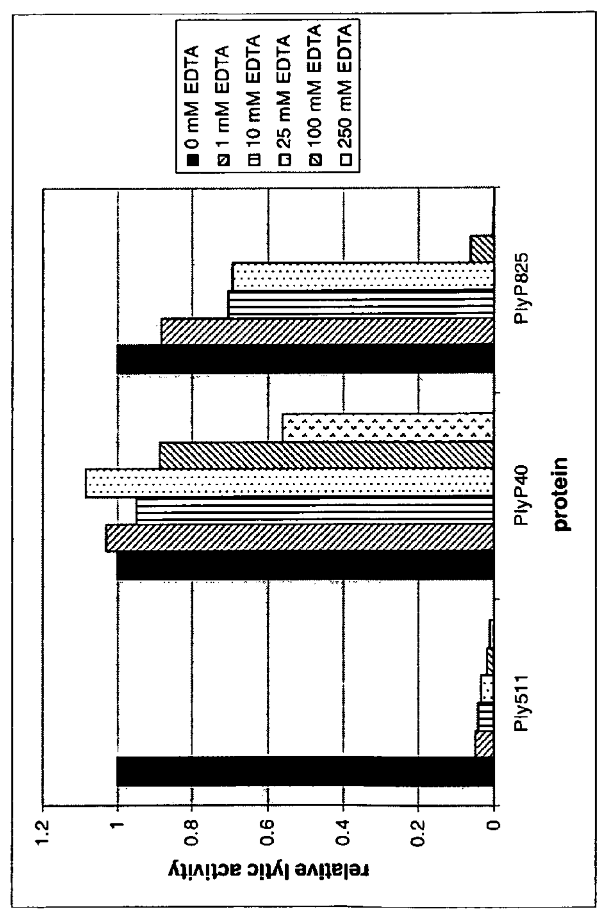
FIG. 7 shows a comparison of the relative lytic activity of endolysins Ply511, PlyP40, and PlyP825 as a function of the EDTA concentration.

The lytic activity of endolysin PlyP825 in the presence of different concentrations of EDTA was determined (Example 7 and FIG. 7). While Ply511 was inactivated already at a concentration of 1 mM EDTA, the relative lytic activity of PlyP825 remained at a level of about 70% up to a concentration of about 25 mM EDTA.

Figure 8:
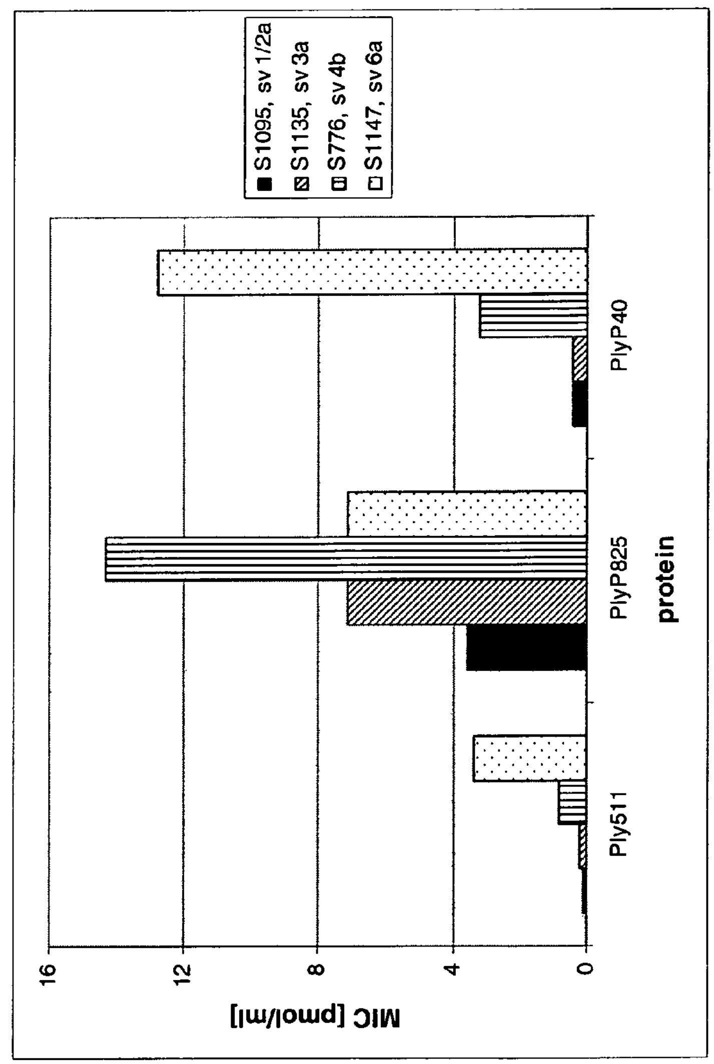

The minimum inhibitory concentration (MIC) of endolysin PlyP825 against *Listeria monocytogenes* ProCC S1095 sv 1/2a, *Listeria monocytogenes* ProCC S1135 sv 3a, *Listeria monocytogenes* ProCC S776 sv 4b, and *Listeria* innocua ProCC S1147 sv 6a was determined (Example 8 and FIG. 8). The minimum inhibitory concentration (MIC) is defined as the lowest concentration of an antimicrobial agent at which the visible growth of a microorganism is suppressed (Andrews et al. 2001). The MIC values varied depending on the *Listeria* strain tested. For inhibiting *Listeria monocytogenes* ProCC S1095 sv 1/2a and *Listeria monocytogenes* ProCC S1135 sv 3a less PlyP825 protein was required than for inhibiting *Listeria monocytogenes* ProCC S776 sv 4b. The MIC values for PlyP825 are, depending on the *Listeria* strain tested, about 2.3-times lower, or up to 17.75-times higher than the MIC values for PlyP40.

*Listeria* Serovar 3 Specific Bacteriophage

The present invention provides bacteriophage capable of lysing *Listeria* serovar 3 obtainable by (a) plating a sample containing bacteriophage and *Listeria* bacteria serovar 3 using agar plates to obtain plaques, and (b) purifying the phage contained within the one or more plaques obtained.

In various embodiments, the step of plating a phage-containing sample and *Listeria* bacteria serovar 3 comprises mixing a phage-containing sample and *Listeria* serovar 3 host cells in molten, "soft" agar. The resulting suspension is then poured on to an appropriate "nutrient" basal agar medium to form a thin "top layer" which hardens and immobilises the bacteria. In various embodiments, the step of plating a phage-containing sample and *Listeria* bacteria serovar 3 follows the double agar layer method as described by Adams (1959).

During incubation the uninfected *Listeria* bacteria multiply to form a confluent lawn of bacterial growth over the surface of the plate. Each infected bacterium bursts after a short time and liberates progeny phages that infect adjacent bacteria, which in turn are lysed. This "chain" reaction spreads in a circular motion until brought to a halt by a decline in bacterial metabolism. Plaques are zones of bacterial lysis caused by bacteriophage action and appear as circular zones of lysis on lawns of bacterial cells.

Phages may be purified by removing, picking off, a well isolated plaque using either a Pasteur pipette or more crudely, but just as effectively, a wire loop. Using a sterile Pasteur pipette, the area around the plaque is stabbed and pieces of soft area are "sucked" into the pipette. The agar should be gently broken into smaller pieces with the wire-loop, mixed briefly with a vortex-mixer and left for 5-10 minutes at ambient temperature. The phage suspension may then be filter-sterilised through a 0.45 mμ syringe-mounted, filtration unit to remove any bacteria including phage-resistant host bacteria.

In various embodiments, the sample is an environmental sample, preferably a sample from environmental water, more preferably a water sample from a rivulet. In various embodiments, the sample is a phage suspension.

In case of the phage-containing sample being a phage suspension, the step of plating a phage-containing sample and *Listeria* bacteria serovar 3 comprises mixing a small volume of a dilution of a phage suspension and *Listeria* serovar 3 host cells in molten, "soft" agar.

FURTHER DEFINITIONS

In the present invention, "Percentage (%) of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity", in the context of two or more nucleic acids or polypeptide sequences, refer to two or more sequences or sub-sequences that are the same or have a specified percentage of amino acid resides or nucleotides that are the same, when compared and aligned for maximum correspondence over a comparison window, or designated region as measured using one of the following sequence comparison algorithms or by manual alignment and visual inspection. Such sequences are then said to be "substantially identical". This definition also refers to the complement of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The terms nucleic acid molecule and nucleic acid sequence may be used herein interchangeably.

As discussed herein there are numerous variants of the proteins and polypeptides of the present invention. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Deletions are characterized by the removal of one or more amino acid residues from the protein sequence. Typically, no more than about from 2 to 6 residues are deleted at any one site within protein molecules according to the present invention. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known to the ones skilled in the art. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one amino acid residue has been removed and a different amino acid residue inserted in its place such that a conservative substitution is obtained. The meaning of a conservative substitution is well known to the person skilled in the art.

Certain post-translational modifications are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains, acetylation of the N-terminal amine and, in some instances, amidation of the C-terminal carboxyl. Such post-translational modifications are also contemplated by the present invention.

The term "*Listeria*" as used herein means the bacterial genus *Listeria*. In the present invention, the genus *Listeria* encompasses all known *Listeria* species. In particular, in the present invention the genus *Listeria* includes, but is not limited to, the following *Listeria* species: *L. monocytogenes, L. seeligeri, L. ivanovii, L. innocua, L. welshimeri, L. grayi* ssp. *grayi*, and *L. grayi* ssp. *murrayi*.

In the present invention, the preferred *Listeria* species is a *Listeria* species that is pathogenic to human beings and/or animals.

In various embodiments of the present invention, the preferred *Listeria* species is *Listeria monocytogenes*, which is pathogen to both human and animals. This applies in particular to the therapeutic and non-therapeutic methods of the present invention.

In the present invention, *Listeria* serovars 1/2, 3, and 4 include, but are not limited to, *Listeria monocytogenes* serovars 1/2, 3, and 4, respectively.

In various embodiments, the preferred *Listeria monocytogenes* serovar is serovar 1/2. In various other embodiments, the preferred *Listeria monocytogenes* serovar is serovar 3. In various further embodiments, the preferred *Listeria monocytogenes* serovar is serovar 4.

In the present invention *Listeria monocytogenes* includes serotypes 1/2a, 1/2b, 1/2c, 3a, 3b, 3c, 4a, 4ab, 4b, 4c, 4d, 4e, and 7. In various embodiments, the *Listeria* species is selected from the group consisting of *L. monocytogenes* serotype 1/2a, *L. monocytogenes* serotype 1/2b, *L. monocytogenes* serotype 1/2c, *L. monocytogenes* serotype 3a, *L. monocytogenes* serotype 3b, *L. monocytogenes* serotype 3c, *L. monocytogenes* serotype 4a, *L. monocytogenes* serotype 4ab, *L. monocytogenes* serotype 4b, *L. monocytogenes* serotype 4c, *L. monocytogenes* serotype 4d, *L. monocytogenes* serotype 4e, and *L. monocytogenes* serotype 7.

In more preferred embodiments of the present invention the *Listeria* species is selected from the group consisting of *L. monocytogenes* 1142 serovar 1/2a, *L. monocytogenes* 1042 serovar 4b, *L. monocytogenes* 1019 serovar 4c, *L. monocytogenes* 1001 serovar 1/2c, *L. monocytogenes* EGDe serovar 1/2a, *L. monocytogenes* SLCC 7150 serovar 1/2a, *L. monocytogenes* SLCC 7154 serovar 1/2c, *L. monocytogenes* SLCC 7290 serovar 1/2c, *L. monocytogenes* 0756062 serovar 1/2c, *L. monocytogenes* WSLC1485 serovar 1/3a, *L. monocytogenes* WSLC 11082 serovar 1/3c, *L. monocytogenes* WSLC 11083 serovar 1/3c, *L. monocytogenes* ScottA serovar 4b, *L. monocytogenes* WSLC 1048 serovar 4d, *L. monocytogenes* 8309032 serovar 4d, and *L. monocytogenes* 8309033 serovar 4e.

In various embodiments, the preferred *Listeria* species is *Listeria* ivanovii, which is pathogenic to animals. In preferred embodiments, the *Listeria* species is *Listeria* ivanovii serotype 5.

The literature discloses reports about diseases in human beings resulting from infection with *Listeria seeligeri* (Rocourt et al. 1987) and *L. ivanovii* (Cummins et al. 1994). In the present invention *Listeria seeligeri* includes serotypes I/2a, I/2b, I/2c, 4b, 4c, 4d, and 6b. In various embodiments, the *Listeria* species is selected from the group consisting of *L. seeligeri* serotype I/2a, serotype I/2b, serotype I/2c, serotype 4b, serotype 4c, serotype 4d, and serotype 6b.

In the present invention *Listeria* innocua includes serotypes 3, 6a, 6b, 4ab, and U/S. In various embodiments, the *Listeria* species is selected from the group consisting of *L. innocua* serotype 3, *L. innocua* serotype 6a, *L. innocua* serotype 6b, *L. innocua* serotype 4ab, and *L. innocua* serotype U/S. Preferably, *L. innocua* is *L. innocua* 2011 serotype 6a.

In the present invention *Listeria welshimeri* includes serotypes 1/2a, 4c, 6a, 6b, and U/S. In various embodiments, the *Listeria* species is selected from the group consisting of *L. welshimeri* serotype 1/2a, *L. welshimeri* serotype 4c, *L. welshimeri* serotype 6a, *L. welshimeri* serotype 6b, and *L. welshimeri* serotype U/S.

In the present invention *Listeria grayi* includes serotype *Grayi*. In various embodiments, the *Listeria* species is *L. grayi* serotype *Grayi*.

In the present invention, the terms "serotype" and "serovar" may be used interchangeably.

In the present invention, the terms "controlling *Listeria* contamination" and "controlling undesired *Listeria* colonization" may be used interchangeably.

The term "endolysin", as used herein, denotes enzymes that are naturally encoded by bacteriophages and are produced by them at the end of their life cycle in the host to lyse the host cell and thereby release the progeny phages. As described in the background section, endolysins are comprised of at least one enzymatically active domain (EAD) and a non-enzymatically active cell binding domain (CBD). The EADs can exhibit different enzymatic activities as described herein, such as, e.g., N-acetyl-muramoyl-L-alanin amidase, (endo)-peptidase, transglycosylase, glycosyl hydrolase, (N-acetyl)-muramidase, or N-acetyl-glucosaminidase. The terms "endolysin(s)" and "lysin(s)" may be used herein interchangeably.

The term "domain" or "protein domain", as used herein, denotes a portion of an amino acid sequence that either has a specific functional and/or structural property. On the basis of amino acid sequence homologies, domains can frequently be predicted by employing appropriate computer programs that compare the amino acid sequences in freely available databases with known domains, e.g., Conserved Domain Database (CDD) at the NCBI (Marchler-Bauer et al., 2005, Nucleic Acids Res. 33, D192-6), Pfam (Finn et al., 2006, Nucleic Acids Research 34, D247-D251), or SMART (Schultz et al., 1998, Proc. Natl. Acad. Sci. USA 95, 5857-5864, Letunic et al., 2006, Nucleic Acids Res 34, D257-D260).

Whenever reference is made to the activity of the polypeptide of SEQ ID NO: 2 (PlyP825), the endolysin activity of PlyP825 is meant. Specifically, the endolysin activity of the polypeptide of SEQ ID NO: 2 (PlyP825) is the lytic activity of the polypeptide of SEQ ID NO: 2 (PlyP825) against *Listeria* bacterial cells described herein, preferably against pathogenic *Listeria* bacterial cells, more preferably *Listeria monocytogenes*. In general, the enzymatic activity of the endolysin of SEQ ID NO: 2 is analogous to the enzymatic activity of known endolysins exhibiting lytic activity against *Listeria* bacterial cells. More specifically, the lytic activity of the endolysin PlyP825 is hydrolytic activity, still more specifically hydrolytic activity against peptidoglycan in the cell wall of *Listeria* bacterial cells. Therefore, the lytic activity of the endolysin PlyP825 may also be described as peptidoglycan hydrolase activity.

As described herein, the EAD of SEQ ID NO: 4 has lytic activity against *Listeria* bacterial cells. In particular, the lytic activity of the EAD of SEQ ID NO: 4 is defined as lytic activity against *Listeria* bacterial cells. More specifically, the enzymatic activity of the EAD of SEQ ID NO: 4 is analogous to the enzymatic activity of known EADs exhibiting lytic activity against *Listeria* bacterial cells. Given the fact that the polypeptide of SEQ ID NO: 4 represents the EAD of the endolysin of SEQ ID NO: 2, and given that EADs from *Listeria* bacteriophages are known and described in the art, the nature of the lytic activity of the EAD of SEQ ID NO: 4 of the present invention is clear to the skilled person. In various embodiments of the present invention, the lytic activity of the EAD of SEQ ID NO: 4 against *Listeria* bacterial cells is peptidoglycan hydrolase activity, i.e. hydrolytic activity against peptidoglycan in the cell wall of *Listeria* bacterial cells. The peptidoglycan hydrolase activity of the EAD of SEQ ID NO: 4 may also be called peptidoglycan-digesting activity or muralytic activity. In various embodiments, the lytic activity of the EAD of SEQ ID NO: 4 is muramidase activity or N-Acteyl-glucosaminidase activity. In various embodiments, the lytic activity of the EAD of SEQ ID NO: 4 is amidase activity or endopeptidase activity. Preferably, the lytic activity of the EAD of SEQ ID NO: 4 is peptidoglycan amidase activity. More preferably, the lytic activity of the EAD of SEQ ID NO: 4 is L-muramoyl-L-alanine amidase activity, D-alanyl-glycyl endopeptidase activity, or D-6-meso-DAP-peptidase or meso-DAP-D-Ala peptidase activity. In various embodiments, the lytic activity of the EAD of SEQ ID NO: 4 is peptidoglycan transglycosylase activity. More preferably, the lytic activity of the EAD of SEQ ID NO: 4 is murein transglycosylase activity. In various embodiments, the lytic activity of the EAD of SEQ ID NO: 4 is peptidase activity, preferably carboxypeptidase activity. In various embodiments, the lytic activity of the EAD of SEQ ID NO: 4 is glycosyl hydrolase activity. In various embodiments, the lytic activity of the EAD of SEQ ID NO: 4 is N-acetylmuramoyl-L-alanine amidase activity. In various embodiments, the lytic activity of the EAD of SEQ ID NO: 4 is cysteine histidine-dependent amidohydrolase/peptidase activity.

As described herein, the CBD of SEQ ID NO: 6 has cell wall binding activity. This cell wall binding activity provides for targeting the lysin to its substrate, namely the peptidoglycan of *Listeria* bacterial cells. Therefore, in particular the cell wall binding activity of the CBD of SEQ ID NO: 6 is *Listeria* cell wall binding activity. In general, the enzymatic activity of the CBD of SEQ ID NO: 6 is analogous to the enzymatic activity of known CBDs that likewise provide for targeting lysin to its substrate in the cell wall of *Listeria* bacterial cells. Given the fact that the polypeptide of SEQ ID NO: 6 represents the CBD of the endolysin of SEQ ID NO: 2, and given that CBDs from *Listeria* bacteriophages are known and described in the art, the nature of the cell wall binding activity of the EAD of SEQ ID NO: 6 of the present invention is clear to the skilled person. Accordingly, it is also clear to the skilled person that CBDs according to the present invention have no or no significant hydrolytic activity like the EADs, i.e. CBDs according to the present invention have no or no significant hydrolytic activity against *Listeria* bacterial cell walls. Here, no or no significant hydrolytic activity is intended to describe the situation whereby the hydrolytic activity of a CBD of the present invention is not sufficient to prevent the application of such a CBD to bind to the cell wall of a *Listeria* bacterial cell. A CBD according to the present invention is supposed to be a protein, which has no or no significant hydrolytic activity itself.

In various embodiments, the cell wall binding activity of the CBD of SEQ ID NO: 6 is binding to peptidoglycan of the cell wall of *Listeria* bacterial cells. Preferably, the cell wall binding activity of the CBD of SEQ ID NO: 6 is binding to a carbohydrate or cholin moiety in the cell wall of *Listeria* bacterial cells. More preferably, the cell wall binding activity of the CBD of SEQ ID NO: 6 is binding to a carbohydrate of the peptidoglycan or teichoic acid or lipoteichoic acid in the cell wall of *Listeria* bacterial cells.

The terms “protein” and “polypeptide” are used in the present invention interchangeably. As used herein, the term endolysin denotes an enzyme. Accordingly, whenever reference is made herein to a protein or polypeptide of the present invention, this also includes endolysins of the present invention. The terms “endolysin(s)” and “endolysin protein(s)” or “endolysin polypeptide(s)” may be used herein interchangeably.

Furthermore, basically the terms “protein” and “polypeptide” as used herein also encompass any “chimeric lysin” provided by the present invention. However, for clarity reasons concerning the scope of the present invention sometimes reference is made herein to “proteins and polypeptides of the present invention” on the one hand, and “chimeric lysins of the present invention” on the other hand. The terms “chimeric lysin(s)” and “chimeric endolysin” may be used herein interchangeably. Furthermore, the terms “chimeric (endo)lysin(s)” and “chimeric (endo)lysin protein(s)” or “chimeric (endo)lysin polypeptide(s)” may be used herein interchangeably.

Furthermore, the term “sv” represent the well known abbreviation of the term “serovar”.

When particular embodiments of the invention are described herein, the corresponding paragraphs/text passages of the description invariably make reference to means and/or methods described elsewhere in the description. In this context, terms like “according to the present invention”, “of the present invention” and “provided by the present invention” are used. That is, when a particular embodiment of the invention is described in a certain paragraph or text passage, reference is made to means and/or methods “according to the present invention” or “of the present invention”, which are described elsewhere in the description. For a particular embodiment described, such references are intended to incorporate for the particular embodiment all means and/or methods, which are described elsewhere in the description and which are provided by the present invention and therefore form part of the scope of the invention. For example, if the description of a particular embodiment refers to “the endolysin according to the present invention” or “the endolysin of the present invention”, or “the endolysin provided by the present invention”, it is intended that all endolysins, which are described elsewhere in the description, and which are provided by the present invention and therefore form part of the scope of the invention, are applicable to the particular embodiment. This particularly applies, for example, to fragments and variants of polypeptides according to the present invention, which are defined in the present invention and which are applicable to the various embodiments described throughout the application text.

The above principle applies to all embodiments making use of terms like “according to the present invention”, “of the present invention” and “provided by the present invention”. It goes without saying that not each embodiment described herein can specifically mention the means and/or methods of the invention, which are already defined elsewhere in the description, and which are applicable to the various embodiments described throughout the application text. Otherwise, each patent application would comprise several hundreds of description pages.

Furthermore, terms like “in various embodiments” and “in various other/further embodiments” mean “in various embodiments of the present invention” and “in various other/further embodiments of the present invention”

The invention is exemplified by the examples, which are not considered to limit the scope of the present invention.

Example 1

Lytic Activity of Phage ProCC P825

The phage P825 provided by the present invention exhibits lytic activity against *Listeria* serovars 1/2, 3, 4, 5 and 6. As demonstrated by the inventors, phage P825 completely inhibited growth of *Listeria monocytogenes* strains.

250 μl overnight culture of different *Listeria* strains were added to 3 ml TB-top-agar (TB-medium, 0.75% (v/v) agar, 2 mM $CaCl_2$, 10 mM $MgSO_4$), and poured into TB-agar plates. 5 μl of phage P825 ($10^9$ pfu/ml) were spotted onto the top-agar plates and dried for about 30 minutes. The plates were incubated overnight at room temperature. Evaluation of lysis spots demonstrated that phage P825 was lytic for all *Listeria* strains tested. Evaluation of lysis spots was performed as follows:

More than 75% of strains tested from one serovar show a lysis spot: “+”

Less than 25% of strains tested from one serovar show a lysis spot: “−”

Not determined: nn.

TABLE 1

Comparison of lytic activity of *Listeria* phages on *Listeria* serovars ("+", "−" and "nn" in accordance with the above definition)

| *Listeria* phage | Serovar 1/2 | Serovar 3 | Serovar 4 | Serovar 5 | Serovar 6 |
|---|---|---|---|---|---|
| P825 | + | + | + | + | + |
| A511 | + | − | + | + | + |
| P100 | + | − | + | + | + |
| A118 | + | − | − | nn | nn |
| A500 | − | − | + | nn | + |
| P40 | − | − | + | + | + |
| PhiLM4 | − | − | + | nn | + |

Phage P825 has been shown to be lytic against *Listeria* serovars 1/2, 3, 4, 5 and 6. The host range is broader than that of known phages A511, P100, A118, A500, P40, and PhiLM4, as shown in the above Table 1. Importantly, novel phage P825 is capable of lysing *Listeria* serovar 3, which is one of the clinically relevant *Listeria* serovars. This activity is unique to novel phage P825. Known *Listeria*-specific bacteriophages A511, P100, A118, A500, P40, and PhiLM4 do not share this property.

Furthermore, phage P825 not only inhibited growth but actually reduced *Listeria* titers. As confirmed by enrichment studies, applying phage P825 completely eradicated *Listeria* bacteria. The lysis spectrum of phage P825 has been shown to be consistent with the binding specificity provided by the tailspike protein of phage P825.

Example 2

Proteolytic Stability of PlyP825 Compared to Ply511 and PlyP40

In order to compare the proteolytic sensitivity of the three endolysins they were Trypsin-digested in equimolar amounts. Aliquots were retained and analyzed after 0 and 3 min incubation at room temperature (FIG. 1). As shown in FIG. 1, PlyP825 possesses less proteolytic degradation sites compared to Ply511 and PlyP40.

Example 3

Lytic Activity of PlyP825 Against a Broad Range of *Listeria* Serovars

PlyP825 was analyzed for its activity against different *Listeria* strains with serovars 1/2, 3, 4, 5 and 6. Overnight cultures of *Listeria* cells were poured 1:6 in LB-Top Agar in plates. Onto the solidified agar 2 μg of PlyP825 was spotted. After incubation over night at 30° C. all 22 strains tested were lysed by the endolysin PlyP825 (Table 2). Thus, PlyP825 is a broad range *Listeria* endolysin.

TABLE 2

22 *Listeria* strains tested for lysis by PlyP825. ProCC S: Culture Collection Number of Hyglos Invest GmbH, Bernried, Germany. "+" indicates lysis of this strain by PlyP825.

| ProCC S | Strain | Serovar | PlyP825 |
|---|---|---|---|
| 1095 | *Listeria monocytogenes* EGDe | 1/2a | + |
| 995 | *Listeria monocytogenes* SLCC 7150 | 1/2a | + |
| 1153 | *Listeria seeligeri* WSLC 40140 | 1/2b | + |
| 1002 | *Listeria monocytogenes* SLCC 7154 | 1/2c | + |
| 1003 | *Listeria monocytogenes* SLCC 7290 | 1/2c | + |
| 2867 | *Listeria monocytogenes* 0756062 | 1/2c | + |
| 1135 | *Listeria monocytogenes* WSLC1485 | 3a | + |
| 1154 | *Listeria seeligeri* WSLC 40127 | 3b | + |
| 2991 | *Listeria seeligeri* WSLC 41113 | 3b | + |
| 2974 | *Listeria monocytogenes* WSLC 11082 | 3c | + |
| 2975 | *Listeria monocytogenes* WSLC 11083 | 3c | + |
| 776 | *Listeria monocytogenes* ScottA | 4b | + |
| 1144 | *Listeria monocytogenes* WSLC 1048 | 4d | + |
| 2919 | *Listeria monocytogenes* 8309032 | 4d | + |
| 2920 | *Listeria monocytogenes* 8309033 | 4e | + |
| 857 | *Listeria ivanovii* WSLC 3009 | 5 | + |
| 1014 | *Listeria ivanovii* SLCC 4706 | 5 | + |
| 1164 | *Listeria ivanovii* ssp. *londoniensis* WSLC 30167 | 5 | + |
| 1150 | *Listeria ivanovii* ssp *ivanovii* WSLC 30165 | 5" | + |
| 1147 | *Listeria innocua* WSLC2011 | 6a | + |
| 773 | *Listeria innocua* WSLC 2012 | 6b | + |
| 1754 | *Listeria seeligeri* WSLC 41116 | 6b | + |

Example 4

Minimum Bactericidal Concentration of PlyP825 in Buffer and Milk

The minimum bactericidal concentrations (MBCs) of the endolysins PlyP825, Ply511 and PlyP40 in buffer and in milk were determined and compared.

For determining the MBC in buffer pH 6 the endolysin enzymes were incubated with $10^5$ cells/ml of strains *Listeria monocytogenes* EGDe sv 1/2a and *Listeria* innocua WSLC2011 sv 6a in buffer (20 mM sodium phosphate, 50 mM sodium chloride, 0.05% Tween pH 6) at 30° C. After 1 h the samples were plated and cell numbers counted. FIG. 2 shows the results: PlyP825 reduces effectively pathogenic and non-pathogenic *Listeria* cells in buffer: 0.032 μg/ml endolysin were sufficient to reduce 4.5 (WSLC2011) or 3.1 (EGDe) orders of magnitude of *Listeria* cells. This is about 0.5 to 1.5 log more than Ply511 and 0.9-1.3 log more than PlyP40 were able to reduce with the same protein concentration.

For determining the MBC in milk the enzymes were incubated with $10^5$ cells/ml of strains *Listeria monocytogenes* EGDe sv 1/2a and *Listeria* innocua WSLC2011 sv 6a in milk with 1.5% fat at 30° C. After 3 h the samples were plated and cell numbers counted. FIG. 3 shows the results: PlyP825 shows the highest *Listeria* cell reduction in milk. Independent from the test strain PlyP825 reduces 1.4-1.7 orders of magnitude more cells than the other two broad *Listeria* endolysins Ply511 and PlyP40 in milk with 1.5% fat. Besides the enzymes were incubated with $10^5$ cells/ml of strains *Listeria monocytogenes* EGDe sv 1/2a in milk with 3.5% fat at 30° C. After 3 h the samples were plated and cell numbers counted. FIG. 4 shows the results. Also in milk with 3.5% fat PlyP825 reduces the highest cell number.

Example 5 pH Optimum of PlyP825

The pH optimum for the lytic activity of endolysin PlyP825 was determined and compared with that of endolysins Ply511 and PlyP40. The results are shown in FIG. 5. The lytic activity as a function of the pH was determined applying photometric lysis tests. In particular, heat-inactivated cells of *Listeria monocytogenes* ProCC S1095 sv 1/2a were suspended in buffer (50 mM sodium citrate, 50 mM $NaH_2PO_4$, 50 mM borate and 100 mM NaCl), which was adjusted to pH values of 4.5, 5.5, 6.5, 7.5, 8.5 and 9.5, respectively. As shown in FIG. 5, PlyP825 and Ply511 exhibit highest lytic activity at neutral to slightly alkaline (basic) pH. Thus, endolysins PlyP825 and Ply511 have a pH optimum at neutral to slightly alkaline (basic) pH. The result shown for Ply511 confirms the pH optimum described in the literature (Pieper et al. 2005). PlyP40 exhibits highest lytic activity at acidic pH. Thus, endolysin PlyP40 has a pH optimum at acidic pH.

Example 6

Salt (NaCl) Optimum of PlyP825

The salt optimum (NaCl) for the lytic activity of endolysin PlyP825 was determined and compared with that of endolysins Ply511 and PlyP40. The results are shown in FIG. 6. The lytic activity of endolysins Ply511, PlyP40 and PlyP825 against *Listeria monocytogenes* ProCC S1095 sv 1/2a was determined at pH6 for concentrations of 0 mM, 10 mM, 50 mM, 100 mM, 150 mM, 250 mM, and 500 mM NaCl. As shown in FIG. 6, endolysins Ply511 and PlyP825 exhibit highest lytic activities in the concentration range of about 150-250 mM NaCl. Thus, endolysins Ply511 and PlyP825 have a salt (NaCl) optimum of about 150-250 mM NaCl. Furthermore, as shown in FIG. 6 endolysin PlyP40 exhibits highest lytic activity at a concentration of about 150 mM NaCl. Thus, endolysin PlyP40 has a salt (NaCl) optimum of about 150 mM NaCl.

Example 7

Relative Lytic Activity of PlyP825 in the Presence of EDTA

The lytic activity of endolysin PlyP825 in the presence of different concentrations of EDTA was determined and compared with that of endolysins Ply511 and PlyP40. The results are shown in FIG. 7. The lytic activity as a function of the EDTA concentration was determined applying photometric lysis tests using *Listeria monocytogenes* ProCC S1095 sv 1/2a as reference strain. The incubation period was one hour at pH 6 and different concentrations of EDTA. As shown in FIG. 7, Ply511 was inactivated already at a concentration of 1 mM EDTA, and at a concentration of 250 mM EDTA the residual activity was about 1%. Furthermore, as shown in FIG. 7, the relative lytic activity of PlyP40 remained almost unchanged up to a concentration of 100 mM EDTA, and the relative lytic activity of PlyP825 remained at a level of about 70% up to a concentration of about 25 mM EDTA. At a concentration of 250 mM EDTA the residual lytic activity of PlyP825 was about 2.5%.

Example 8

MIC of PlyP825 Against *Listeria*

The minimum inhibitory concentration (MIC) of endolysin PlyP825 against *Listeria monocytogenes* ProCC S1095 sv 1/2a, *Listeria monocytogenes* ProCC S1135 sv 3a, *Listeria monocytogenes* ProCC S776 sv 4b, and *Listeria innocua* ProCC S1147 sv 6a was determined and compared with that of endolysins Ply511 and PlyP40. The results are shown in FIG. 8. The minimum inhibitory concentration (MIC) is defined as the lowest concentration of an antimicrobial agent at which the visible growth of a microorganism is suppressed (Andrews et al. 2001). For determining the MIC cells of *Listeria monocytogenes* ProCC S1095 sv 1/2a, *Listeria monocytogenes* ProCC S1135 sv 3a, *Listeria monocytogenes* ProCC S776 sv 4b, and *Listeria innocua* ProCC S1147 sv 6a, respectively, were incubated in TB medium at pH 6. The growth of the *Listeria* strains tested was observed by determining optical density (OD). As shown in FIG. 8, the MIC values varied depending on the *Listeria* strain tested. For inhibiting *Listeria monocytogenes* ProCC S1095 sv 1/2a and *Listeria monocytogenes* ProCC S1135 sv 3a in general less protein was required than for inhibiting *Listeria monocytogenes* ProCC S776 sv 4b and *Listeria innocua* ProCC S1147 sv 6a. Ply511 shows the lowest MIC values 0.10 to 3.34 pmol/ml. The concentrations for PlyP40 were higher than the concentrations for Ply511, namely by a factor of about 1.75 to about 3.5. The MIC values for PlyP825 are, depending on the *Listeria* strain tested, about 2.3-times lower, or up to 17.75-times higher than the MIC values for PlyP40.

REFERENCES

McLauchlin J. (1987). *Listeria monocytogenes*, recent advances in the taxonomy and epidemiology of listeriosis in humans. Journal of Applied Bacteriology 63(1):1-11.

Oevermann A., Botteron C., Seuberlich T. et al. (2008). Neuropathological survey of fallen stock: active surveillance reveals high prevalence of encephalitic listeriosis in small ruminants. Veterinary Microbiology 130 (3-4):320-329.

Gillespie I. A., McLauchlin J., Grant K. A. et al. (2006). Changing pattern of human listeriosis, England and Wales, 2001-2004, Emerging Infectious Diseases 12(9): 1361-1366.

Goulet V., Hedberg C., Le Monnier A., and de Valk H. (2008). Increasing incidence of listeriosis in France and other European countries, Emerging Infectious Diseases 14(5):734-740.

Gillespie I. A., McLauchlin J., Little C. L. et al. (2009). Disease presentation in relation to infection foci for non-pregnancy associated human listeriosis in England and Wales, 2001 to 2007. J. Clinic. Microbiology 47(10): 3301-3307.

Doumith M., Cazalet C., Simoes N., et al. (2004). New aspects regarding evolution and virulence of *Listeria monocytogenes* revealed by comparative genomics and DNA arrays, Infection and Immunity 72(2):1072-1083.

Oevermann A., Zurbriggen A., and Vandevelde M. (2010). Rhombencephalitis caused by *Listeria monocytogenes* in humans and ruminants: A zoonosis on the rise?. Interdisciplinary Perspectives on Infectious Diseases, Volume 2010, Article ID 632513, 22 pages.

Hagens S, and Loessner M. J. (2007). Application of bacteriophages for detection and control of foodborne pathogens, Appl. Microbiol. Biotechnol. 76(3):513-519.

Loessner M. J., Kramer K., Ebel F. and Scherer S. (2002). C-terminal domains of *Listeria monocytogenes* bacteriophage murein hydrolases determine specific recognition and high-affinity binding to bacterial cell wall carbohydrates. Mol. Microbiol. 44:335-349.

Zink R. and Loessner M. J. (1992). Classification of Virulent and Temperate Bacteriophages of *Listeria* spp. on the Basis of Morphology and Protein Analysis. Appl. Environm. Microbiol. 58(1):296-302.
Rocourt J., Schrettenbrunner A., Hof H., and Espace E. P. (1987). *Listeria seeligeri*, a new species of the genus *Listeria*. Pathol. Biol. 35:1075-1080.
Cummins A. J., Fielding A. K., McLauchhlin J. (1994). *Listeria* ivanovii infection in a patient with AIDS. J. Infect. 28: 89-91.
Adams M. (1959). Bacteriophages. New York: Interscience Publishers, 137-159.

The invention claimed is:

1. A food product comprising a bacteriophage having a genome i) comprising the DNA sequence of SEQ ID NO: 7;

ii) having at least 90% or 95% sequence identity with the DNA sequence of SEQ ID NO: 7; or iii) having at least 90% or 95% sequence identity with the DNA sequence of the genome of bacteriophage ProCC P825 deposited under Accession No. DSM 23783;

wherein the food product is selected from the group consisting of a dairy product, a fruit product, a vegetable product, a meat product, and a fish product.

2. The food product of claim 1, which is a dairy product.

3. The food product of claim 1, which is a fruit product.

4. The food product of claim 1, which is a vegetable product.

5. The food product of claim 1, which is a meat product.

6. The food product of claim 1, which is a fish product.

7. The dairy product of claim 2, which is a pasteurized dairy product.

8. The dairy product of claim 2, selected from the group consisting of yoghurt, ice cream, cheese and butter.

9. The meat product of claim 5, selected from the group consisting of pate, hot dog, bologna, salami and cold cuts.

10. The food product of claim 1, wherein the food product has undergone thermal treatment prior to introducing the bacteriophage.

11. The food product of claim 10, wherein the thermal treatment is at a temperature of at least 70° C.

12. The food product of claim 2, wherein the bacteriophage has a genome comprising the DNA sequence of SEQ ID NO: 7.

13. The food product of claim 1, wherein the bacteriophage has a genome having at least 90% or 95% sequence identity with the DNA sequence of SEQ ID NO: 7.

14. The food product of claim 1, wherein the bacteriophage has a genome having at least 90% or 95% sequence identity with the DNA sequence of the genome of bacteriophage ProCC P825 deposited under Accession No. DSM 23783.

* * * * *